US007375093B2

(12) United States Patent
Tice et al.

(10) Patent No.: US 7,375,093 B2
(45) Date of Patent: May 20, 2008

(54) KETONE LIGANDS FOR MODULATING THE EXPRESSION OF EXOGENOUS GENES VIA AN ECDYSONE RECEPTOR COMPLEX

(75) Inventors: Colin M. Tice, Elkins Park, PA (US); Enrique L. Michelotti, Fort Washington, PA (US); Robert E. Hormann, Melrose Park, PA (US)

(73) Assignee: Intrexon Corporation, Blacksburg, VA (US)

( * ) Notice: Subject to any disclaimer, the term of this patent is extended or adjusted under 35 U.S.C. 154(b) by 255 days.

(21) Appl. No.: 10/614,116

(22) Filed: Jul. 3, 2003

(65) Prior Publication Data

US 2004/0049037 A1    Mar. 11, 2004

Related U.S. Application Data

(60) Provisional application No. 60/393,960, filed on Jul. 5, 2002.

(51) Int. Cl.
*A01N 43/04*     (2006.01)
*A01N 33/18*     (2006.01)
*C12N 5/00*      (2006.01)
*C12N 15/00*     (2006.01)

(52) U.S. Cl. ............... 514/44; 435/325; 435/320.1; 514/676

(58) Field of Classification Search .............. None
See application file for complete search history.

(56) References Cited

U.S. PATENT DOCUMENTS

| 3,676,453 | A |   | 7/1972  | Pines et al |
|-----------|---|---|---------|-------------|
| 3,716,573 | A |   | 2/1973  | Pives |
| 4,971,993 | A |   | 11/1990 | Kurauchi et al. |
| 5,304,572 | A | * | 4/1994  | Michelotti et al. ......... 514/514 |
| 5,324,483 | A |   | 6/1994  | Cody et al. |
| 5,523,308 | A |   | 6/1996  | Costanzo et al. |
| 2003/0153464 | A1 | * | 8/2003 | Nakamura et al. ......... 504/257 |

FOREIGN PATENT DOCUMENTS

| EP | 0 405 537 B1     | 9/2004 |
|----|------------------|--------|
| WO | WO 01/60783 A1   | 8/2001 |
| WO | WO 02/051820 A1  | 7/2002 |
| WO | WO 02/053543 A1  | 7/2002 |
| WO | WO 02/059077 A1  | 8/2002 |

OTHER PUBLICATIONS

Martinez et al., Mol Gen Genet, 1999, 261: 546-552.*
Dhadialla et al., Annu Rev Entomol, 1998, 43: 545-569.*
Saez et al., Proc Natl Acad Sci USA, 2000, 97: 14512-14517.*
Guan et al., Journal of Combinatorial Chemistry, 2000, 2: 297-300.*
Ryding et al., J Endocrinol, 2001, 171: 1-14.*
Martinez et al., The Plant Journal, 1999, 19: 97-106.*
Aumann, R., and Heinen, H., "(C-Amino)ketenimine, 2-Imidazolin-5-one and α-Aminosäureamide aus (Aminocarben)chromkomplexen und Isocyaniden," *Chem. Ber.* 122:1139-1145, VHC Verlagsgesellschaft mbH (1989).
Awad, W.I., et al., "Studies on 2-Phenyl-4-Arlyidene-5-Oxazolones," *Tetrahedron* 20:891-896, Pergamon Press Ltd. (1964).
Choong, I.C., et al., "Identification of Potent and Selective Small-Molecule Inhibitors of Caspase-3 through the Use of Extended Tethering and Structure-Based Drug Design," *J. Med. Chem.* 45:5005-5022, American Chemical Society (Nov. 2002).
El'kinson R.S. and Eremeev, A.V., "Reactions of Azirines with Sulfur Nucleophiles. 4. Treatment of 2H-Azirine With Mercaptosubstituted Acids. Reactions of Aziridinyl Alkyl Sulfides With Carboxylic Acids and Acyl Chloride Derivatives," *Chem. Heterocycl. Compd.* 22:161-166, Plenum Publishing Corporation (1986).
Goujon, J-Y., and Shipman, M., "Concise route to α-acylamino-β-keto amides: application to the synthesis of a simplified azinomycin A analogue," *Tetrahedron Lett.* 43:9573-9576, Elsevier Science Ltd. (Dec. 2002).
Huebner, C.F., and Scholz, C.R., "The Synthesis of Cholramphenicol Analogs," *J. Am. Chem. Soc* 73:2089-2094, American Chemical Society (1951).
Lachicotte, R.J., et al., "C-Acylation of Hippurate and Related Esters Utilizing Multiple Anion Intermediate and Ethyl 4-Aminobenzoate," *Synth. Commun.* 20:63-69, Marcel Dekker, Inc. (1990).
Liu, J., et al., "Improved syntheses of α-BOC-aminoketones from α-BOC-amino-Weinreb amides using a pre-deprotonation protocol," *Tetrahedron Lett.* 43:8223-8226, Elsevier Science Ltd. (Nov. 2002).
MacPherson, E.J. and Smith J.G., "Alkali metal adducts of benzophenone azine. I. The sodium and potassium adducts," *Can. J. Chem.* 48:1904-1914, NRC Research Press (1969).
Mizuno, H., et al., "Stereochemical Studies. V11: Thermal Rearrangement of α-Hydroxyimines to α-Aminoketones using optically Active Open Chain Compounds," *Chem. Pharm. Bull.* 71:227-246, Pharmaceutical Society of Japan (1971).
Ooi, T., et al., "Asymmetric Induction in the Neber Rearrangement of Simple Ketoxime Sulfonates under Phase-Transfer Conditions: Experimental Evidence for the Participation of an Anionic Pathway," *J. Am. Chem. Soc.* 124:7640-7641, American Chemical Society (Jun. 2002).
Pines, H.S., et al., "3-Aryl-2-methylserines. I. A New Synthesis," *J.Org. Chem.* 33:1758-1761, American Chemical Society (1968).
Pines, S.H., and Sletzinger, M., "3-Aryl-2-Methylserines III. Synthesis via Alanine Azlactone," *Tetrahedron Lett.* 9:727-728, Pergamon Press (1969).

(Continued)

*Primary Examiner*—Joseph Woitach
*Assistant Examiner*—Ileana Popa
(74) *Attorney, Agent, or Firm*—Sterne, Kessler, Goldstein & Fox P.L.L.C.

(57) ABSTRACT

This invention relates to a method to modulate exogenous gene expression in which an ecdysone receptor complex comprising: a DNA binding domain; a ligand binding domain; a transactivation domain; and a ligand is contacted with a DNA construct comprising: the exogenous gene and a response element; wherein the exogenous gene is under the control of the response element and binding of the DNA binding domain to the response element in the presence of the ligand results in activation or suppression of the gene. The ligands comprise a class of ketones.

12 Claims, 1 Drawing Sheet

OTHER PUBLICATIONS

Pines, S.H., et al., "3-Aryl-2-methylserines. II. Inversions at Carbon 3," *J. Org. Chem.* 33:1762-1767, American Chemical Society (1968).

Siedel, W and Nahm, H, "Über die Hydrierung von α-Benzoyl-*N*-acyl-serin-benzylestern," *Chem. Ber.* 88:900-911, VHC Verlagsgesellschaft mbH (1955).

Subramanyam, C., and Chang, S.P., "Solid-Phase synthesis of peptidyl α-keto heterocycles," *Tetrahedron Lett.* 43:6313-6315, Elsevier Science Ltd. (Sep. 2002).

Tamaru, Y., et al., "Sulfinate As Cocatalyst 3: Palladium Catalyzed Dimerization of Butadiene with Acylamino Ketones," *Tetrahedron Lett.* 21:3791-3794, Pergamon Press Ltd. (1980).

Van Der Meer, S., et al., "Chloramphenicol Analogues I DL-2-Dichloroacetamido-1-(4-pyridyl)-1,3-propanediol," *Recl. Trav. Chim. Pays-Bas 72*:236-246, Société chimique neerlandaise (1953).

STNEasy Database, Accession No. 1989:422724, English language abstract for Aumann, R., and Heinen, H., "(C-Amino)ketenimine, 2-Imidazolin-5-one and α-Aminosäureamide aus (Aminocarben)chromkomplexen und Isocyaniden,"*Chem. Ber. 122*:1139-1145, VHC Verlagsgesellschaft mbH (1989).

STN Easy Database, Accession No. 1956:40246, English language abstract for Sidel, W and Nahm, H, "Über die Hydrierug von α-Benzoyl-*N*-acyl-serin-benzylestern," *Chem. Ber.* 88:900-911, VHC Verlagsgesellschaft mbH (1955).

\* cited by examiner

SEQUENCE LISTING

<160> NUMBER OF SEQ ID NOS: 14

<210> SEQ ID NO 1
<211> LENGTH: 1073
<212> TYPE: DNA
<213> ORGANISM: Choristoneura fumiferana

<400> SEQUENCE: 1

```
cctgagtgcg tagtacccga gactcagtgc gccatgaagc ggaaagagaa gaaagcacag      60
aaggagaagg acaaactgcc tgtcagcacg acgacggtgg acgaccacat gccgcccatt     120
atgcagtgtg aacctccacc tcctgaagca gcaaggattc acgaagtggt tccaaggttt     180
ctctccgaca agctgttgga gacaaaccgg cagaaaaaca tccccagtt gacagccaac      240 cagcagttcc ttatcgccag gctcatctgg taccaggacg ggtacgagca gccttctgat     300
gaagatttga gaggattac gcagacgtgg cagcaagcgg acgatgaaaa cgaagagtct      360
gacactccct tccgccagat cacagagatg actatcctca cggtccaact tatcgtggag     420
ttcgcgaagg gattgccagg gttcgccaag atctcgcagc ctgatcaaat tacgctgctt     480
aaggcttgct caagtgaggt aatgatgctc cgagtcgcca gatacgatgc ggcctcagac     540
agtgttctgt tcgcgaacaa ccaagcgtac actcgcgaca actaccgcaa ggctggcatg     600
gcctacgtca tcgaggatct actgcacttc tgccggtgca tgtactctat ggcgttggac     660
aacatccatt acgcgctgct cacggctgtc gtcatctttt ctgaccggcc agggttggag     720
cagccgcaac tggtggaaga atccagcgg tactacctga atacgctccg catctatatc      780
ctgaaccagc tgagcgggtc ggcgcgttcg tccgtcatat acggcaagat cctctcaatc     840
ctctctgagc tacgcacgct cggcatgcaa aactccaaca tgtgcatctc cctcaagctc     900
aagaacagaa agctgccgcc tttcctcgag gagatctggg atgtggcagg acatgtcgca     960
cacccaaccg ccgcctatct cgagtccccc acgaatctct agccctgcg cgcacgcatc     1020 gccgatgccg cgtccggccg cgctgctctg agaattcgat atcaagcttc tag           1073
```

<210> SEQ ID NO 2
<211> LENGTH: 481
<212> TYPE: DNA
<213> ORGANISM: Saccharomyces cerevisiae

<400> SEQUENCE: 2

```
ctagccagct tgaagcaagc ctcctgaaag atgaagctac tgtcttctat cgaacaagca      60
tgcgatattt gccgacttaa aaagctcaag tgctccaaag aaaaaccgaa gtgcgccaag     120
tgtctgaaga acaactggga gtgtcgctac tctcccaaaa ccaaaaggtc tccgctgact     180
agggcacatc tgacagaagt ggaatcaagg ctagaaagac tggaacagct atttctactg     240 attttcctc gagaagacct tgacatgatt ttgaaaatgg attctttaca ggatataaaa      300
gcattgttaa caggattatt tgtacaagat aatgtgaata aagatgccgt cacagataga     360
ttggcttcag tggagactga tatgcctcta acattgagac agcatagaat aagtgcgaca     420
tcatcatcgg aagagagtag taacaaaggt caaagacagt tgactgtatc gccggaattc     480
``` c                                                                                    481

<210> SEQ ID NO 3
<211> LENGTH: 538
<212> TYPE: DNA
<213> ORGANISM: Mus musculus

<400> SEQUENCE: 3
tcgagggccc ctgcaggtca attctaccgg gtaggggagg cgcttttccc aaggcagtct      60
ggagcatgcg ctttagcagc cccgctggca cttggcgcta cacaagtggc ctctggcctc     120
gcacacattc cacatccacc ggtagcgcca accggctccg ttctttggtg gccccttcgc     180
gccaccttct actcctcccc tagtcaggaa gttcccccc gccccgcagc tcgcgtcgtg      240
caggacgtga caaatggaag tagcacgtct cactagtctc gtgcagatgg acagcaccgc     300
tgagcaatgg aagcgggtag gcctttgggg cagcggccaa tagcagcttt gctccttcgc     360
tttctgggct cagaggctgg gaaggggtgg gtccgggggc gggctcaggg gcgggctcag     420
ggcggggcg gcgcgaagg tcctcccgag gcccggcatt ctcgcacgct tcaaaagcgc       480
acgtctgccg cgctgttctc ctcttcctca tctccgggcc tttcgacctg cagccaat      538

<210> SEQ ID NO 4
<211> LENGTH: 720
<212> TYPE: DNA
<213> ORGANISM: Artificial
<220> FEATURE:
<223> OTHER INFORMATION: HsRXRbeta-EF-LmUSP-EF

<400> SEQUENCE: 4
gaattcgaga tgcctgtgga caggatcctg gaggcagagc ttgctgtgga acagaagagt      60
gaccagggcg ttgagggtcc tggggggaacc ggggggtagcg gcagcagccc aaatgaccct    120
gtgactaaca tctgtcaggc agctgacaaa cagctattca cgcttgttga gtgggcgaag     180
aggatcccac acttttcctc cttgcctctg gatgatcagg tcatattgct gcgggcaggc     240
tggaatgaac tcctcattgc ctccttttca caccgatcca ttgatgttcg agatggcatc     300
ctccttgcca caggtcttca cgtgcaccgc aactcagccc attcagcagg agtaggagcc     360
atctttgatc gggtgctgac agagctagtg tccaaaatgc gtgacatgag gatggacaag     420
acagagcttg gctgcctgag ggcaatcatt ctgtttaatc cagaggtgag gggtttgaaa     480
tccgcccagg aagttgaact ctacgtgaaa aaagtatatg ccgctttgga agaatatact     540
agaacaacac atcccgatga accaggaaga tttgcaaaac ttttgcttcg tctgcttct     600
ttacgttcca taggccttaa gtgttttgag catttgtttt tctttcgcct tattggagat      660
gttccaattg atacgttcct gatggagatg cttgaatcac cttctgattc ataatctaga     720

<210> SEQ ID NO 5
<211> LENGTH: 276
<212> TYPE: DNA
<213> ORGANISM: Herpes simplex virus 7

<400> SEQUENCE: 5
ctagcgccgc caccatgggc cctaaaaaga agcgtaaagt cgcccccccg accgatgtca      60
gcctggggga cgagctccac ttagacgcg aggacgtggc gatggcgcat gccgacgcgc     120
tagacgattt cgatctggac atgttggggg acggggattc ccgggggccg ggatttaccc     180
cccacgactc cgcccctac ggcgctctg atatggccga cttcgagttt gagcagatgt      240
ttaccgatgc ccttggaatt gacgagtacg gtgggg                              276

```
<210> SEQ ID NO 6
<211> LENGTH: 1167
<212> TYPE: DNA
<213> ORGANISM: Homo sapiens

<400> SEQUENCE: 6
tgaggctccg gtgcccgtca gtgggcagag cgcacatcgc ccacagtccc cgagaagttg      60
gggggagggg tcggcaattg aaccggtgcc tagagaaggt ggcgcggggt aaactgggaa     120
agtgatgtcg tgtactggct ccgcctttt cccgagggtg ggggagaacc gtatataagt     180
gcagtagtcg ccgtgaacgt tcttttcgc aacgggtttg ccgccagaac acaggtaagt     240
gccgtgtgtg gttcccgcgg gcctggcctc tttacgggtt atggcccttg cgtgccttga     300
attacttcca cctggctcca gtacgtgatt cttgatcccg agctggagcc aggggcgggc     360
cttgcgcttt aggagcccct tcgcctcgtg cttgagttga ggcctggcct gggcgctggg     420
gccgccgcgt gcgaatctgg tggcaccttc gcgcctgtct cgctgctttc gataagtctc     480
tagccattta aaattttga tgacctgctg cgacgctttt tttctggcaa gatagtcttg     540
taaatgcggg ccaggatctg cacactggta tttcggtttt tgggcccgcg gccggcgacg     600
gggcccgtgc gtcccagcgc acatgttcgg cgaggcgggg cctgcgagcg cggccaccga     660
gaatcggacg ggggtagtct caagctgcc ggcctgctct ggtgcctggc ctcgcgccgc     720
cgtgtatcgc cccgccctgg gcggcaaggc tgcccggtc ggcaccagtt gcgtgagcgg     780
aaagatggcc gcttcccggc cctgctccag ggggctcaaa atggaggacg cggcgctcgg     840
gagagcgggc gggtgagtca cccacacaaa ggaaaagggc ctttccgtcc tcagccgtcg     900
cttcatgtga ctccacggag taccgggcgc cgtccaggca cctcgattag ttctggagct     960
tttggagtac gtcgtcttta ggttgggggg aggggtttta tgcgatggag tttccccaca    1020
ctgagtgggt ggagactgaa gttaggccag cttggcactt gatgtaattc tcgttggaat    1080
ttgccctttt tgagtttgga tcttggttca ttctcaagcc tcagacagtg gttcaaagtt    1140 ttttttcttcc atttcaggtg tcgtgaa                                       1167

<210> SEQ ID NO 7
<211> LENGTH: 94
<212> TYPE: DNA
<213> ORGANISM: Artificial
<220> FEATURE:
<223> OTHER INFORMATION: GAL4 response element

<400> SEQUENCE: 7
tcggagtact gtcctccgag cggagtactg tcctccgagc ggagtactgt cctccgagcg      60
gagtactgtc ctccgagcgg agtactgtcc tccg                                  94

<210> SEQ ID NO 8
<211> LENGTH: 6
<212> TYPE: DNA
<213> ORGANISM: Artificial sequence
<220> FEATURE:
<223> OTHER INFORMATION: synthetic promoter

<400> SEQUENCE: 8 tatata                                                                  6

<210> SEQ ID NO 9
<211> LENGTH: 1653
<212> TYPE: DNA
```

<213> ORGANISM: Artificial
<220> FEATURE:
<223> OTHER INFORMATION: Luciferase

<400> SEQUENCE: 9

| | | | | | |
|---|---|---|---|---|---|
| atggaagacg | ccaaaaacat | aaagaaaggc | ccggcgccat | tctatcctct | agaggatgga | 60 |
| accgctggag | agcaactgca | taaggctatg | aagagatacg | ccctggttcc | tggaacaatt | 120 |
| gcttttacag | atgcacatat | cgaggtgaac | atcacgtacg | cggaatactt | cgaaatgtcc | 180 |
| gttcggttgg | cagaagctat | gaaacgatat | gggctgaata | caaatcacag | aatcgtcgta | 240 |
| tgcagtgaaa | actctcttca | attctttatg | ccggtgttgg | gcgcgttatt | tatcggagtt | 300 |
| gcagttgcgc | ccgcgaacga | catttataat | gaacgtgaat | tgctcaacag | tatgaacatt | 360 |
| tcgcagccta | ccgtagtgtt | tgtttccaaa | aaggggttgc | aaaaaatttt | gaacgtgcaa | 420 |
| aaaaaattac | caataatcca | gaaaattatt | atcatggatt | ctaaaacgga | ttaccaggga | 480 |
| tttcagtcga | tgtacacgtt | cgtcacatct | catctacctc | ccggttttaa | tgaatacgat | 540 |
| tttgtaccag | agtcctttga | tcgtgacaaa | acaattgcac | tgataatgaa | ttcctctgga | 600 |
| tctactgggt | tacctaaggg | tgtggcccct | ccgcatagaa | ctgcctgcgt | cagattctcg | 660 |
| catgccagag | atcctatttt | tggcaatcaa | atcattccgg | atactgcgat | tttaagtgtt | 720 |
| gttccattcc | atcacggttt | tggaatgttt | actacactcg | gatatttgat | atgtggattt | 780 |
| cgagtcgtct | taatgtatag | atttgaagaa | gagctgtttt | tacgatccct | tcaggattac | 840 |
| aaaattcaaa | gtgcgttgct | agtaccaacc | ctattttcat | tcttcgccaa | aagcactctg | 900 |
| attgacaaat | acgatttatc | taatttacac | gaaattgctt | ctgggggcgc | acctctttcg | 960 |
| aaagaagtcg | gggaagcggt | tgcaaaacgc | ttccatcttc | cagggatacg | acaaggatat | 1020 |
| gggctcactg | agactacatc | agctattctg | attacacccg | agggggatga | taaaccgggc | 1080 |
| gcggtcggta | aagttgttcc | attttttgaa | gcgaaggttg | tggatctgga | taccgggaaa | 1140 |
| acgctgggcg | ttaatcagag | aggcgaatta | tgtgtcagag | gacctatgat | tatgtccggt | 1200 |
| tatgtaaaca | atccggaagc | gaccaacgcc | ttgattgaca | aggatggatg | gctacattct | 1260 |
| ggagacatag | cttactggga | cgaagacgaa | cacttcttca | tagttgaccg | cttgaagtct | 1320 |
| ttaattaaat | acaaaggata | tcaggtggcc | cccgctgaat | tggaatcgat | attgttacaa | 1380 |
| caccccaaca | tcttcgacgc | gggcgtggca | ggtcttcccg | acgatgacgc | cggtgaactt | 1440 |
| cccgccgccg | ttgttgtttt | ggagcacgga | aagacgatga | cggaaaaaga | gatcgtggat | 1500 |
| tacgtcgcca | gtcaagtaac | aaccgcgaaa | aagttgcgcg | gaggagttgt | gtttgtggac | 1560 |
| gaagtaccga | aaggtcttac | cggaaaactc | gacgcaagaa | aaatcagaga | gatcctcata | 1620 |
| aaggccaaga | agggcggaaa | gtccaaattg | taa | | | 1653 |

<210> SEQ ID NO 10
<211> LENGTH: 786
<212> TYPE: DNA
<213> ORGANISM: Mus musculus

<400> SEQUENCE: 10

| | | | | | |
|---|---|---|---|---|---|
| aagcgggaag | ctgtgcagga | ggagcggcag | cggggcaagg | accggaatga | gaacgaggtg | 60 |
| gagtccacca | gcagtgccaa | cgaggacatg | cctgtagaga | agattctgga | agccgagctt | 120 |
| gctgtcgagc | ccaagactga | gacatacgtg | gaggcaaaca | tggggctgaa | ccccagctca | 180 |
| ccaaatgacc | ctgttaccaa | catctgtcaa | gcagcagaca | agcagctctt | cactcttgtg | 240 |
| gagtgggcca | agaggatccc | acacttttct | gagctgcccc | tagacgacca | ggtcatcctg | 300 |

```
ctacgggcag gctggaacga gctgctgatc gcctccttct cccaccgctc catagctgtg    360
aaagatggga ttctcctggc caccggcctg cacgtacacc ggaacagcgc tcacagtgct    420
ggggtgggcg ccatctttga cagggtgcta acagagctgg tgtctaagat gcgtgacatg    480
cagatggaca agacggagct gggctgcctg cgagccattg tcctgttcaa ccctgactct    540 aagggctct caaaccctgc tgaggtggag gcgttgaggg agaaggtgta tgcgtcacta     600
gaagcgtact gcaaacacaa gtaccctgag cagccgggca ggtttgccaa gctgctgctc    660
cgcctgcctg cactgcgttc catcgggctc aagtgcctgg agcacctgtt cttcttcaag    720
ctcatcgggg acacgcccat cgacaccttc ctcatggaga tgctggaggc accacatcaa    780
gccacc                                                               786

<210> SEQ ID NO 11
<211> LENGTH: 1263
<212> TYPE: DNA
<213> ORGANISM: Aedes aegypti

<400> SEQUENCE: 11
cggccggagt gcgtcgtgcc ggagaaccag tgcgccatca agcggaagga gaagaaagcc     60
cagaaggaga aggacaaggt gcaaacgaac gccaccgtca gtacaacgaa cagcacctac    120
cggtcggaga tactgccgat cctgatgaaa tgtgatccac cgccgcacca gcgatacct    180 ctactaccgg aaaagctcct gcaggagaat aggctaagaa acatacctct actgacggcg    240
aaccaaatgg ccgtcattta caaactcatc tggtaccagg acgggtacga gcaaccctcg    300
gaggaagatc tcaaacggat aatgatcggt tcacccaacg aggaggaaga tcaacatgac    360
gtgcacttcc ggcacataac ggaaatcaca atcctaacag tacaactaat cgtggagttc    420
gccaagggac tgccagcatt taccaagatt ccacaggagg accagatcac gctgctgaag    480
gcctgctcaa gcgaggttat gatgttgcga atggcccgcc gctacgacgc tgccaccgat    540
tcgatcctgt tcgcgaacaa ccggtcctac acgagggact cctaccggat ggccggcatg    600
gcggacacga tagaggacct gctgcacttc tgccggcaga tgttctccct cacggtagac    660
aacgtcgagt acgcactcct cacggcgata gtcatcttct cggatcggcc cggactggag    720
caagccgaac tggtcgagca catccagagc tactacatcg acacgctgcg gatctacatc    780
ctgaataggc acgcgggcga tccgaagtgc agtgtgatat tcgccaaact gctgtcgatc    840
ctgacggagc tccgaacgct gggcaaccag aactcggaga tgtgcttctc gctcaagctg    900
aagaaccgca aactgccacg gttcctggag gagatctggg acgtccagga cataccgccc    960
tcgatgcagg cccagatgca cagccatggc acccagtcct cgtcctcatc gtcctccagt   1020
agtagtagta gtagtaacgg tagtagtaac ggtaacagta gtagtaatag taatagttca   1080
cagcacgggc cacatccgca tccgcacggg cagcaattaa cgccaaatca gcagcagcat   1140
cagcagcagc acagtcagtt acagcaagtt cacgccaacg gcagcggaag tggtggcggc   1200
agtaacaata atagcagtag tgggggcgta gtcccgggcc tcggcatgct cgaccaggta   1260
tag                                                                 1263

<210> SEQ ID NO 12
<211> LENGTH: 1022
<212> TYPE: DNA
<213> ORGANISM: Cytomegalovirus

<400> SEQUENCE: 12
```

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat      300
agtaacgcca tagggactt tccattgacg tcaatgggtg gagtatttac ggtaaactgc      360
ccacttggca gtacatcaag tgtatcatat gccaagtccg ccccctattg acgtcaatga     420
cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca gtctccacc ccattgacgt      600 caatgggagt ttgttttggc accaaaatca acgggacttt ccaaaatgtc gtaacaactg     660
cgatcgcccg ccccgttgac gcaaatgggc ggtaggcgtg tacggtggga ggtctatata    720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
ag                                                                    1022

<210> SEQ ID NO 13
<211> LENGTH: 719
<212> TYPE: DNA
<213> ORGANISM: Mus musculus

<400> SEQUENCE: 13
ttcgagatgc ctgtggacag gatcctggag gcagagcttg ctgtggaaca gaagagtgac      60
cagggcgttg agggtcctgg gggaaccggg ggtagcggca gcagcccaaa tgaccctgtg     120
actaacatct gtcaggcagc tgacaaacag ctattcacgc ttgttgagtg ggcgaagagg     180
atcccacact tttcctcctt gcctctggat gatcaggtca tattgctgcg ggcaggctgg     240
aatgaactcc tcattgcctc cttttcacac cgatccattg atgttcgaga tggcatcctc     300
cttgccacag gtcttcacgt gcaccgcaac tcagcccatt cagcaggagt aggagccatc     360
tttgatcggg tgctgacaga gctagtgtcc aaaatgcgtg acatgaggat ggacaagaca     420
gagcttggct gcctgagggc aatcattctg tttaatccag atgccaaggg cctctccaac     480
cctagtgagg tggaggtcct gcgggagaaa gtgtatgcat cactggagac ctactgcaaa     540
cagaagtacc ctgagcagca gggacggttt gccaagctgc tgctacgtct tcctgccctc     600
cggtccattg gccttaagtg tctagagcat ctgtttttct tcaagctcat tggtgacacc     660
cccatcgaca ccttcctcat ggagatgctt gaggctcccc atcaactggc ctgaaagct      719

<210> SEQ ID NO 14
<211> LENGTH: 368
<212> TYPE: DNA
<213> ORGANISM: Simian virus 40

<400> SEQUENCE: 14
tatgtatcat acacatacga tttaggtgac actatagaac tcgactgtgg aatgtgtgtc      60
agttagggtg tggaaagtcc ccaggctccc cagcaggcag aagtatgcaa agcatgcatc     120
```

```
tcaattagtc agcaaccagg tgtggaaagt ccccaggctc cccagcaggc agaagtatgc    180
aaagcatgca tctcaattag tcagcaacca tagtcccgcc cctaactccg cccatcccgc    240
ccctaactcc gcccagttcc gcccattctc cgccccatgg ctgactaatt tttttattt    300 atgcagaggc cgaggccgcc tcggcctctg agctattcca gaagtagtga agaggctttt    360
ttggagga                                                            368
```

KETONE LIGANDS FOR MODULATING THE EXPRESSION OF EXOGENOUS GENES VIA AN ECDYSONE RECEPTOR COMPLEX

This application claims priority to U.S. provisional application Ser. No. 60/393,960, filed Jul. 5, 2002.

FIELD OF THE INVENTION

This invention relates to the field of biotechnology or genetic engineering. Specifically, this invention relates to the field of gene expression. More specifically, this invention relates to novel nuclear receptors comprising a substitution mutation and their use in a nuclear receptor-based inducible gene expression system and methods of modulating the expression of a gene within a host cell using this inducible gene expression system.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurm et al., 1986, Proc. Natl. Acad. Sci. USA 83:5414-5418; Arnheiter et al., 1990 Cell 62:51-61; Filmus et al., 1992 Nucleic Acids Research 20:27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, *Science* 262:1019-24; Belshaw et al., 1996 *Proc Natl Acad Sci U S A* 93:4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998. Annu. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530,028). Both analogs have exceptional safety profiles to other organisms.

The insect ecdysone receptor (EcR) heterodimerizes with Ultraspiracle (USP), the insect homologue of the mammalian RXR, and binds ecdysteroids and ecdysone receptor response elements and activate transcription of ecdysone responsive genes. The EcR/USP/ligand complexes play important roles during insect development and reproduction. The EcR is a member of the steroid hormone receptor superfamily and has five modular domains, A/B (transactivation), C (DNA binding, heterodimerization)), D (Hinge, heterodimerization), E (ligand binding, heterodimerization and transactivation and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

The first version of EcR-based gene switch used *Drosophila melanogaster* EcR (DmEcR) and *Mus musculus* RXR (MmRXR) and showed that these receptors in the presence of steroid, ponasteroneA, transactivate reporter genes in mammalian cell lines and transgenic mice (Christopherson K. S., Mark M. R., Baja J. V., Godowski P. J. 1992, Proc. Natl. Acad. Sci. U.S.A. 89: 6314-6318; No D., Yao T. P., Evans R. M., 1996, Proc. Natl. Acad. Sci. U.S.A. 93: 3346-3351). Later, Suhr et al. 1998, Proc. Natl. Acad. Sci. 95:7999-8004 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880,333). Therefore, a need exists in the art for improved EcR-based systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. For certain applications such as gene therapy, it may be desirable to have an inducible gene expression system that responds well to synthetic non-steroid ligands and at the same is insensitive to the natural steroids. Thus, improved systems that are simple, compact, and dependent on ligands that are relatively inexpensive, readily available, and of low toxicity to the host would prove useful for regulating biological systems.

Recently, it has been shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gene expression modulation system compared to the two systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell resulting in reduced side effects.

With the improvement in ecdysone receptor-based gene regulation systems there is an increase in their use in various applications resulting in increased demand for ligands with higher activity than those currently exist. U.S. Pat. No. 6,258,603 B 1 (and patents cited therein) disclosed dibenzoylhydrazine ligands, however, in order to provide a variety of approaches to the control of gene expression utilizing the known receptors, there remains a continuing need to develop new classes of ligands which are neither steroidal nor diacylhydrazines. We have discovered a class of ligands which have not previously been shown to have the ability to modulate the expression of transgenes.

SUMMARY OF THE INVENTION

Figure 1:
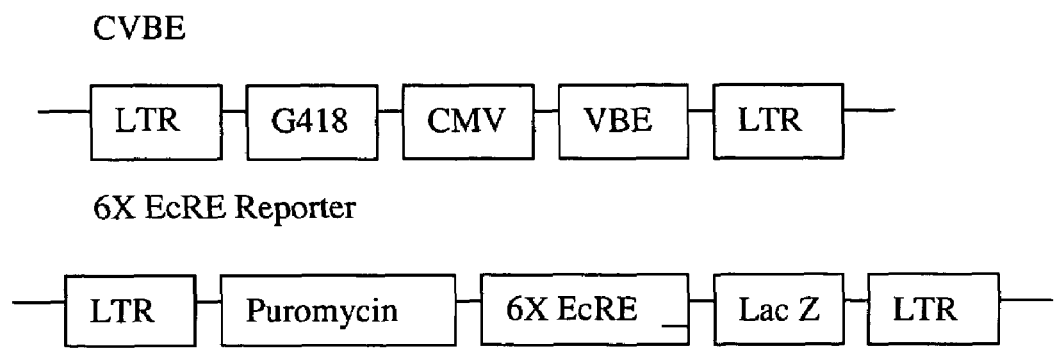
FIG. 1: is a schematic diagram of a switch and reporter construct used to measure transactivation of *Bombyx mori* EcR by the compounds of the present invention.

The present invention pertains to compounds of the general formula I-III:

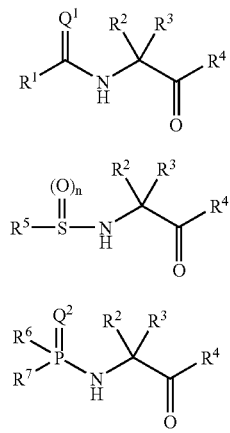

The present invention also relates to methods to transactivate ecdysone receptor-based inducible gene expression systems using a ligand of formula I, II or III and methods for modulating the expression of a gene in a host cell by introducing into the host cell a gene expression modulation system and activating that system using a ligand of formula I, II or III.

DETAILED DESCRIPTION OF THE PREFERRED EMBODIMENT

The present invention pertains to compounds of general formula I-III:

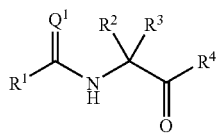

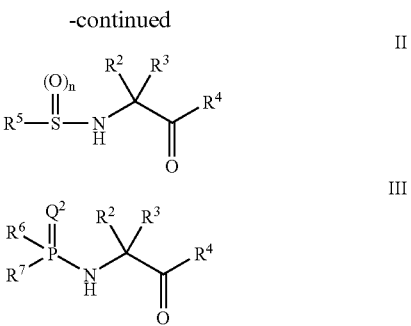

wherein $Q^1$ and $Q^2$ are independently selected from the group consisting of O and S;

n=1 or 2;

$R^1$ is:

a) $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_2-C_6)$haloalkenyl, $(C_2-C_6)$alkynyl, $(C_2-C_6)$haloalkynyl, $(C_1-C_6)$alkoxy, $(C_3-C_6)$cycloalkoxy, $(C_1-C_6)$haloalkoxy, $(C_3-C_6)$halocycloalkoxy, $(C_2-C_6)$alkenyloxy, $(C_2-C_6)$alkynyloxy, $(C_1-C_6)$alkylthio, $(C_3-C_6)$cycloalkylthio, $(C_1-C_6)$haloalkylthio, $(C_3-C_6)$halocycloalkylthio, $(C_1-C_6)$alkylamino, $(C_3-C_6)$cycloalkylamino, $(C_1-C_6)$haloalkylamino, $(C_3-C_6)$halocycloalkylamino, di$(C_1-C_6)$alkylamino, di$(C_3-C_6)$cycloalkylamino, di$(C_1-C_6)$haloalkylamino, di$(C_3-C_6)$halocycloalkylamino, $(C_1-C_6)$alkoxy$(C_1-C_6)$alkyl, $(C_1-C_6)$althylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl$(C_1-C_6)$alkyl, or cyano$(C_1-C_6)$alkyl; or b) unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, where the substituents are independently selected from one to four of the following:

i cyano, nitro, halo, aminocarbonyl, aminothiocarbonyl, carboxy, formyl, hydroxy, amino, carbamoyl, $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_3-C_6)$cycloalkenyl, $(C_3-C_6)$alkadienyl, $(C_2-C_6)$alkynyl, $(C_1-C_6)$alkoxy, $(C_3-C_6)$cycloalkoxy, $(C_1-C_6)$haloalkoxy, $(C_3-C_6)$cyclohaloalkoxy, $(C_2-C_6)$alkenyloxy, $(C_2-C_6)$alkynyloxy, $(C_1-C_6)$alkylthio, $(C_3-C_6)$cycloalkylthio, $(C_1-C_6)$haloalkylthio, $(C_3-C_6)$halocycloalkythio, $(C_2-C_6)$alkenylthio, $(C_2-C_6)$alkynylthio, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_2-C_6)$alkenylsulfinyl, $(C_3-C_6)$cycloalkenylsulfinyl, $(C_2-C_6)$alkynylsulfinyl, $(C_1-C_6)$alkylsulfonyl, $(C_3-C_6)$cycloalkysulfonyl, $(C_1-C_6)$haloalkylsulfonyl, $(C_3-C_6)$halocycloalkylsulfonyl, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_1-C_6)$alkylamino, $(C_3-C_6)$cycloalkylamino, di$(C_1-C_6)$alkylamino, di$(C_3-C_6)$(cycloalkyl)amino, $(C_1-C_6)$alkoxy$(C_1-C_6)$alkyl, $(C_3-C_6)$cycloalkoxyalkyl, $(C_1-C_6)$alkoxy$(C_3-C_6)$cycloalkyl, $(C_1-C_6)$alkylthio$(C_1-C_6)$alkyl, $(C_1-C_6)$alkylsulfinyl$(C_1-C_6)$alkyl, $(C_1-C_6)$ alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$) alkylcarbonyl, ($C_3$-$C_6$)cycloalkylcarbonyl, ($C_1$-$C_6$) alkoxycarbonyl, ($C_1$-$C_6$)alkylaminocarbonyl, ($C_3$-$C_6$)cycloalkylaminocarbonyl, di($C_1$-$C_6$) alkylaminocarbonyl, di($C_3$-$C_6$)(cycloalkyl) aminocarbonyl, cyano($C_1$-$C_6$)alkyl, or tri($C_1$-$C_6$) alkylsilyl; or ii unsubstituted or substituted phenyl, phenyl($C_1$-$C_6$) alkyl, heterocyclyl, phenoxy, heterocyclyloxy, benzoyl, heterocyclylcarbonyl, phenylthio, heterocyclylthio, phenylsulfonyl, or heterocyclylsulfonyl wherein one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, ($C_1$-$C_3$)alkylsulfonyl, ($C_1$-$C_3$)alkylamino, di($C_1$-$C_3$) alkylamino, ($C_1$-$C_2$)alkoxy($C_1$-$C_2$)alkyl, ($C_1$-$C_2$) alkylthio($C_1$-$C_2$)alkyl, ($C_1$-$C_2$)alkylsulfonyl($C_1$-$C_2$) alkyl, ($C_1$-$C_2$)alkylamino($C_1$-$C_2$)alkyl, di($C_1$-$C_2$) alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, di($C_1$-$C_3$)alkylaminocarbonyl or cyano($C_1$-$C_3$)alkyl;

wherein in said substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein:

the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$) alkoxy, ($C_1$-$C_3$)haloalkoxy, ($C_1$-$C_3$)alkythio, ($C_1$-$C_3$) haloalkylthio, ($C_1$-$C_3$)alkylsulfonyl, ($C_1$-$C_3$) alkylamino, di($C_1$-$C_3$)alkylamino, ($C_1$-$C_2$)alkoxy($C_1$-$C_2$) alkyl, ($C_1$-$C_2$)alkylthio($C_1$-$C_2$)alkyl, ($C_1$-$C_2$) alkylsulfonyl($C_1$-$C_2$)alkyl, ($C_1$-$C_2$)alkylamino($C_1$-$C_2$) alkyl, di($C_1$-$C_2$)alkylamino($C_1$-$C_2$)alkyl, ($C_1$-$C_3$) alkylcarbonyl, ($C_1$-$C_3$)alkoxycarbonyl, ($C_1$-$C_3$) alkylaminocarbonyl, di($C_1$-$C_3$)alkylaminocarbonyl, cyano($C_1$-$C_3$)alkyl, oxo, and methoxyimino;

provided that when $R^1$ is phenyl, the phenyl is substituted at at least two adjacent positions; wherein the substituents are fused to form a ring;

$R^2$ and $R^3$ are independently selected from:

a) cyano, aminocarbonyl, carboxy, ($C_1$-$C_6$)alkyl, ($C_3$-$C_6$) cycloalkyl, halo($C_1$-$C_6$)alkyl, ($C_3$-$C_6$)halocycloalkyl, ($C_2$-$C_6$)alkenyl, ($C_3$-$C_6$)cycloalkenyl, ($C_2$-$C_6$)haloalkenyl, ($C_2$-$C_6$)alkynyl, ($C_1$-$C_6$)alkylsulfonyl, ($C_1$-$C_6$) alkoxy($C_1$-$C_6$)alkyl, ($C_1$-$C_6$)althylthio($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl, ($C_1$-$C_6$)alkylcarbonyl($C_1$-$C_6$)alkyl, ($C_1$-$C_6$)alkylaminocarbonyl, ($C_1$-$C_6$)alkylaminocarbonyl, ($C_1$-$C_6$)alkylaminocarbonyl($C_1$-$C_6$)alkyl, di($C_1$-$C_6$)alkylaminocarbonyl($C_1$-$C_6$)alkyl, ($C_1$-$C_6$) alkylcarbonylamino($C_1$-$C_6$)alkyl, ($C_1$-$C_6$) alkoxycarbonyl, ($C_1$-$C_6$)alkoxycarbonyl($C_1$-$C_6$)alkyl, cyano($C_1$-$C_6$)alkyl, hydroxy($C_1$-$C_6$)alkyl, or carboxy ($C_1$-$C_6$)alkyl; or b) unsubstituted or substituted phenyl, phenyl($C_1$-$C_6$) alkyl, benzoyl, naphthyl, pyridyl, pyrazinyl, pyridazinyl, pyrimidinyl, furanyl, thiophenyl, benzothiophenyl, benzofuranyl, isoxazolyl, imidazolyl or other heterocyclyl, heterocyclylcarbonyl, wherein one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$) alkoxy, ($C_1$-$C_3$)haloalkoxy, ($C_1$-$C_3$)alkythio, ($C_1$-$C_3$) haloalkylthio, ($C_1$-$C_3$)alkylsulfonyl, ($C_1$-$C_3$) alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$) alkylsulfonyl($C_1$-$C_2$)alkyl, ($C_1$-$C_2$)alkylamino($C_1$-$C_2$) alkyl, di($C_1$-$C_2$)alkylamino($C_1$-$C_2$)alkyl, ($C_1$-$C_3$) alkylcarbonyl, ($C_1$-$C_3$)alkoxycarbonyl, ($C_1$-$C_3$) alkylaminocarbonyl, di($C_1$-$C_3$)alkylaminocarbonyl, and cyano($C_1$-$C_3$)alkyl;

wherein $R^2$ and $R^3$ may be joined together with the carbon to which they are attached to form an unsubstituted or substituted, partially unsaturated or saturated 3-, 4-, 5-, 6-, 7- or 8-membered carbocyclic or heterocyclic ring wherein the heterocyclic ring contains from one to three heteroatoms selected from O, N, or S; and one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$) alkoxy, ($C_1$-$C_3$)haloalkoxy, ($C_1$-$C_3$)alkythio, ($C_1$-$C_3$) haloalkylthio, ($C_1$-$C_3$)alkylsulfonyl, ($C_1$-$C_3$)alkylamino, di($C_1$-$C_3$)alkylamino, ($C_1$-$C_2$)alkoxy($C_1$-$C_2$) alkyl, ($C_1$-$C_2$)alkylthio($C_1$-$C_2$)alkyl, ($C_1$-$C_2$) alkylsulfonyl($C_1$-$C_2$)alkyl, ($C_1$-$C_2$)alkylamino($C_1$-$C_2$) alkyl, di($C_1$-$C_2$)alkylamino($C_1$-$C_2$)alkyl, ($C_1$-$C_3$) alkylcarbonyl, ($C_1$-$C_4$)alkoxycarbonyl, ($C_1$-$C_4$) alkoxycarbonyl($C_1$-$C_4$)alkyl, ($C_1$-$C_4$) alkoxycarbonylcarbonyl, ($C_1$-$C_3$)alkylaminocarbonyl, di($C_1$-$C_3$)alkylaminocarbonyl, cyano($C_1$-$C_3$)alkyl, oxo, methoxyimino, and spiro-($C_1$-$C_4$)alkadioxy;

$R^4$ is selected from:

a) ($C_1$-$C_6$)alkyl, ($C_3$-$C_6$)cycloalkyl, ($C_1$-$C_6$)haloalkyl, ($C_3$-$C_6$)halocycloalkyl, ($C_2$-$C_6$)alkenyl, ($C_2$-$C_6$)haloalkenyl, ($C_2$-$C_6$)alkynyl, ($C_2$-$C_6$)haloalkynyl, ($C_1$-$C_6$)alkoxy, ($C_3$-$C_6$)cycloalkoxy, ($C_1$-$C_6$)haloalkoxy, ($C_3$-$C_6$)halocycloalkoxy, ($C_2$-$C_6$)alkenyloxy, ($C_2$-$C_6$) alkynyloxy, ($C_1$-$C_6$)alkylthio, ($C_3$-$C_6$)cycloalkylthio, ($C_1$-$C_6$)haloalkylthio, ($C_3$-$C_6$)halocycloalkylthio, ($C_1$-$C_6$)alkylamino, ($C_3$-$C_6$)cycloalkylamino, ($C_1$-$C_6$)haloalkylamino, ($C_3$-$C_6$)halocycloalkylamino, di($C_1$-$C_6$) alkylamino, di($C_3$-$C_6$)cycloalkylamino, di($C_1$-$C_6$) haloalkylamino, di($C_3$-$C_6$)halocycloalkylamino, ($C_1$-$C_6$)alkoxy($C_1$-$C_6$)alkyl, ($C_1$-$C_6$)althylthio($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl($C_1$-$C_6$)alkyl, or cyano($C_1$-$C_6$)alkyl; or b) unsubstituted or substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein one to four substituents are independently selected from:

i cyano, nitro, halo, aminocarbonyl, aminothiocarbonyl, carboxy, formyl, hydroxy, amino, carbamoyl, $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_3-C_6)$cycloalkenyl, $(C_3-C_6)$alkadienyl, $(C_2-C_6)$alkynyl, $(C_1-C_6)$alkoxy, $(C_3-C_6)$cycloalkoxy, $(C_1-C_6)$haloalkoxy, $(C_3-C_6)$cyclohaloalkoxy, $(C_2-C_6)$alkenyloxy, $(C_2-C_6)$alkynyloxy, $(C_1-C_6)$alkylthio, $(C_3-C_6)$cycloalkylthio, $(C_1-C_6)$haloalkylthio, $(C_3-C_6)$halocycloalkythio, $(C_2-C_6)$alkenylthio, $(C_2-C_6)$alkynylthio, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_2-C_6)$alkenylsulfinyl, $(C_3-C_6)$cycloalkenylsulfinyl, $(C_2-C_6)$alkynylsulfinyl, $(C_1-C_6)$alkylsulfonyl, $(C_3-C_6)$cycloalkysulfonyl, $(C_1-C_6)$haloalkylsulfonyl, $(C_3-C_6)$halocycloalkylsulfonyl, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_1-C_6)$alkylamino, $(C_3-C_6)$cycloalkylamino, di$(C_1-C_6)$alkylamino, di$(C_3-C_6)$(cycloalkyl)amino, $(C_1-C_6)$alkoxy$(C_1-C_6)$alkyl, $(C_3-C_6)$cycloalkoxyalkyl, $(C_1-C_6)$alkoxy$(C_3-C_6)$cycloalkyl, $(C_1-C_6)$alkylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl, $(C_3-C_6)$cycloalkylcarbonyl, $(C_1-C_6)$alkoxycarbonyl, $(C_1-C_6)$alkylaminocarbonyl, $(C_3-C_6)$cycloalkylaminocarbonyl, di$(C_1-C_6)$alkylaminocarbonyl, di$(C_3-C_6)$(cycloalkyl)aminocarbonyl, cyano$(C_1-C_6)$alkyl, or tri$(C_1-C_6)$alkylsilyl; or ii unsubstituted or substituted phenyl, phenyl$(C_1-C_6)$alkyl, heterocyclyl, phenoxy, heterocyclyloxy, benzoyl, heterocyclylcarbonyl, phenylthio, heterocyclylthio, phenylsulfonyl, or heterocyclylsulfonyl, wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl and cyano$(C_1-C_3)$alkyl;

wherein in said substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino;

$R^5$ is:

a) $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_2-C_6)$haloalkenyl, $(C_2-C_6)$alkynyl, $(C_2-C_6)$haloalkynyl, $(C_1-C_6)$alkoxy$(C_1-C_6)$alkyl, $(C_1-C_6)$althylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl$(C_1-C_6)$alkyl, or cyano$(C_1-C_6)$alkyl; or b) unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, where one to four substituents are independently selected from:

i cyano, nitro, halo, aminocarbonyl, aminothiocarbonyl, carboxy, formyl, hydroxy, amino, carbamoyl, $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_3-C_6)$cycloalkenyl, $(C_3-C_6)$alkadienyl, $(C_2-C_6)$alkynyl, $(C_1-C_6)$alkoxy, $(C_3-C_6)$cycloalkoxy, $(C_1-C_6)$haloalkoxy, $(C_3-C_6)$cyclohaloalkoxy, $(C_2-C_6)$alkenyloxy, $(C_2-C_6)$alkynyloxy, $(C_1-C_6)$alkythio, $(C_3-C_6)$cycloalkylthio, $(C_1-C_6)$haloalkylthio, $(C_3-C_6)$halocycloalkythio, $(C_2-C_6)$alkenylthio, $(C_2-C_6)$alkynylthio, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_2-C_6)$alkenylsulfinyl, $(C_3-C_6)$cycloalkenylsulfinyl, $(C_2-C_6)$alkynylsulfinyl, $(C_1-C_6)$alkylsulfonyl, $(C_3-C_6)$cycloalkysulfonyl, $(C_1-C_6)$haloalkylsulfonyl, $(C_3-C_6)$halocycloalkylsulfonyl, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_1-C_6)$alkylamino, $(C_3-C_6)$cycloalkylamino, di$(C_1-C_6)$alkylamino, di$(C_3-C_6)$(cycloalkyl)amino, $(C_1-C_6)$alkoxy$(C_1-C_6)$alkyl, $(C_3-C_6)$cycloalkoxyalkyl, $(C_1-C_6)$alkoxy$(C_3-C_6)$cycloalkyl, $(C_1-C_6)$alkylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl, $(C_3-C_6)$cycloalkylcarbonyl, $(C_1-C_6)$alkoxycarbonyl, $(C_1-C_6)$alkylaminocarbonyl, $(C_3-C_6)$cycloalkylaminocarbonyl, di$(C_1-C_6)$alkylaminocarbonyl, di$(C_3-C_6)$(cycloalkyl)aminocarbonyl, cyano$(C_1-C_6)$alkyl, or tri$(C_1-C_6)$alkylsilyl; or ii unsubstituted or substituted phenyl, phenyl$(C_1-C_6)$alkyl, heterocyclyl, phenoxy, heterocyclyloxy, benzoyl, heterocyclylcarbonyl, phenylthio, heterocyclylthio, phenylsulfonyl, or heterocyclylsulfonyl, wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, and cyano$(C_1-C_3)$alkyl;

wherein in said substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkoxy, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino; and $R^6$ and $R^7$ are independently selected from:

a) $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_2-C_6)$haloalkenyl, $(C_2-C_6)$alkynyl, $(C_2-C_6)$haloalkynyl, $(C_1-C_6)$alkoxy, $(C_3-C_6)$cycloalkoxy, $(C_1-C_6)$haloalkoxy, $(C_3-C_6)$halocycloalkoxy, $(C_2-C_6)$alkenyloxy, $(C_2-C_6)$alkynyloxy, $(C_1-C_6)$alkylthio, $(C_3-C_6)$cycloalkylthio, $(C_1-C_6)$haloalkylthio, $(C_3-C_6)$halocycloalkylthio, $(C_1-C_{2\,6})$alkylamino, $(C_3-C_6)$cycloalkylamino, $(C_1-C_6)$haloalkylamino, $(C_3-C_6)$halocycloalkylamino, di$(C_1C_6)$alkylamino, di$(C_3-C_6)$cycloalkylamino, di$(C_1-C_6)$haloalkylamino, di$(C_3-C_6)$halocycloalkylamino, $(C_1-C_6)$alkoxy$(C_1-C_6)$alkyl, $(C_1-C_6)$althylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl$(C_1-C_6)$alkyl, or cyano$(C_1-C_6)$alkyl; or b) unsubstituted or substituted phenyl, phenyl$(C_1-C_6)$alkyl, heterocyclyl, phenoxy, heterocycloxy, phenylthio, heterocyclylthio, naphthyl, phenylamino, heterocyclylamnino, N-phenyl-N-$(C_1-C_6)$alkylamino, or N-heterocyclyl-N-$(C_1-C_6)$alkylamino wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_2)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, and cyano$(C_1-C_3)$alkyl;

wherein $R^6$ and $R^7$ may be joined together with the phosphorus to which they are attached to form an unsaturated, partially unsaturated, or saturated, unsubstituted or substituted 4- to 7-membered heterocyclic ring wherein the heterocyclic ring contains one phosphorus and from zero to three heteroatoms selected from N, O, or S; and from one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino.

Compounds of formula I, II and III are preferred when:

$Q^1$ is O and $Q^2$ is S, n=2;

$R^1$ is unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, where the substituents are independently selected from the group consisting of one to four of the following groups: cyano, nitro, halo, amino, $(C_1-C_3)$alkyl, $(C_1-C_3)$haloalkyl, $(C_1-C_3)$alkoxy, $(C_1-C_3)$haloalkoxy, $(C_3)$alkenyloxy, $(C_3)$alkynyloxy, $(C_1-C_3)$alkythio, $(C_1-C_3)$haloalkylthio, $(C_3)$alkenylthio, $(C_3)$alkynylthio, $(C_1-C_3)$alkylsulfonyl, $(C_1-C_3)$haloalkylsulfonyl, $(C_1-C_3)$alkylsulfinyl, $(C_1-C_3)$haloalkylsulfinyl $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfinyl$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, and cyano$(C_1-C_3)$alkyl;

wherein in said substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein:

the heterocyclic ring contains from one to three heteroatoms selected from N, O, or S; and one to four substituents are independently selected from the group consisting of: cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino;
provided that when $R^1$ is phenyl, the phenyl is substituted at at least two adjacent positions, the substituents of which are fused to form a ring;

$R^4$ is selected from unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein one to four substituents are independently selected from:
  c) cyano, nitro, halo, carboxy, formyl, hydroxy, amino, $(C_1-C_3)$alkyl, $(C_1-C_3)$haloalkyl, $(C_1-C_3)$alkoxy, $(C_1-C_3)$haloalkoxy, $(C_3)$alkenyloxy, $(C_3)$alkynyloxy, $(C_1-C_3)$alkylthio, $(C_1-C_3)$haloalkylthio, $(C_1-C_3)$alkylsulfinyl, $(C_1-C_3)$haloalkylsulfinyl, $(C_1-C_3)$alkylsulfonyl, $(C_1-C_3)$haloalkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfinyl$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, or cyano$(C_1-C_3)$alkyl; or
  b) unsubstituted or substituted phenyl, phenyl$(C_1-C_2)$alkyl, heterocyclyl, phenoxy, heterocyclyloxy, benzoyl, heterocyclylcarbonyl, phenylthio, heterocyclylthio, phenylsulfonyl, or heterocyclylsulfonyl, wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkylthio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, and cyano$(C_1-C_3)$alkyl;

wherein two adjacent positions on $R^4$ may be joined together with the atoms to which they are attached to form an unsubstituted or substituted, unsaturated, partially unsaturated, or saturated 4-, 5-, 6- or 7-membered carbocyclic or heterocyclic ring wherein:
the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkylthio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino; and $R^6$ and $R^7$ are independently selected from:
a) $(C_1-C_3)$alkyl, $(C_1-C_3)$haloalkyl, $(C_1-C_3)$alkoxy, $(C_3)$alkenyloxy, $(C_3)$alkynyloxy, $(C_1-C_3)$alkylthio, $(C_1-C_3)$alkylamino, di$(C_1-C_3)$alkylamino, $(C_1-C_2)$alkoxy$(C_1-C_2)$alkyl, $(C_1-C_2)$althylthio$(C_1-C_2)$alkyl, $(C_1-C_2)$alkylsulfinyl$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_2)$alkylcarbonyl$(C_1-C_2)$alkyl, or cyano$(C_1-C_3)$alkyl; or
b) unsubstituted or substituted phenyl, phenyl$(C_1-C_2)$alkyl, phenoxy, phenylthio, naphthyl, phenylamino, or N-phenyl-N-$(C_1-C_3)$alkylamino, wherein one to four substituents are independently selected from the group consisting of cyano, nitro, halo, formyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, and cyano$(C_1-C_3)$alkyl; and wherein $R^6$ and $R^7$ may be joined together with the phosphorus to which they are attached to form an unsaturated, partially unsaturated, or saturated, unsubstituted or substituted 4- to 7-membered heterocyclic ring wherein the heterocyclic ring contains one phosphorus and from zero to three heteroatoms selected from N, O, or S; and from one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino.

Compounds of formula I, II and III are more preferred when:
$Q^1$ is O, $Q^2$ is S and n=2;
$R^1$ is unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein the substituents are independently selected from the group consisting of one to four of the following groups: halo, $(C_1-C_3)$alkyl, $(C_1-C_3)$alkoxy, $(C_1-C_3)$alkylthio, $(C_1-C_3)$alkylsulfonyl, $(C_1-C_3)$alkylsulfinyl, $(C_1-C_3)$alkylamino, and di$(C_1-C_3)$alkylamino;
wherein in said substituted phenyl, naphthyl or heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein:
the heterocyclic ring contains from one to three heteroatoms selected from N, O, or S; and
one to four substituents are independently selected from the group consisting of: cyano, $(C_1-C_3)$alkyl, $(C_1-C_3)$alkoxy, $(C_1-C_3)$alkylthio, $(C_1-C_3)$alkylsulfonyl, $(C_1-C_3)$alkylamino, di$(C_1-C_3)$alkylamino, $(C_1-C_3)$alkoxycarbonyl, $(C_1-C_3)$alkylaminocarbonyl, di$(C_1-C_3)$alkylaminocarbonyl, oxo, and methoxyimino;

provided that when $R^1$ is phenyl, the phenyl is substituted at least two adjacent positions, the substituents of which are fused to form a ring;

$R^2$ and $R^3$ are independently selected from the group consisting of: $(C_1-C_6)$alkyl, $(C_3-C_6)$cycloalkyl, halo$(C_1-C_6)$alkyl, $(C_3-C_6)$halocycloalkyl, $(C_2-C_6)$alkenyl, $(C_3-C_6)$cycloalkenyl, $(C_2-C_6)$haloalkenyl, $(C_2-C_6)$alkynyl, $(C_1-C_3)$alkoxy$(C_1-C_3)$alkyl, $(C_1-C_3)$althylthio$(C_1-C_3)$alkyl, $(C_1-C_3)$alkylsulfinyl$(C_1-C_3)$alkyl, $(C_1-C_3)$alkylsulfonyl$(C_1-C_3)$alkyl, $(C_1-C_3)$alkylamino$(C_1-C_3)$alkyl, di$(C_1-C_3)$alkylamino$(C_1-C_3)$alkyl, $(C_1-C_6)$alkylcarbonyl, $(C_1-C_3)$alkylcarbonyl$(C_1-C_3)$alkyl, $(C_1-C_6)$alkylaminocarbonyl, di$(C_1-C_6)$alkylaminocarbonyl, $(C_1-C_3)$alkylaminocarbonyl$(C_1-C_3)$alkyl, di$(C_1-C_3)$alkylaminocarbonyl$(C_1-C_3)$alkyl, $(C_1-C_3)$alkylcarbonylamino$(C_1-C_3)$alkyl, $(C_1-C_6)$alkoxycarbonyl, $(C_1-C_3)$alkoxycarbonyl$(C_1-C_3)$alkyl, cyano$(C_1-C_6)$alkyl, hydroxy$(C_1-C_6)$alkyl, and carboxy$(C_1-C_6)$alkyl;

wherein $R^2$ and $R^3$ may be joined together with the carbon to which they are attached to form an unsubstituted or substituted, partially unsaturated or saturated 3-, 4-, 5-, 6- or 7-membered carbocyclic or heterocyclic ring, wherein the heterocyclic ring contains from one to three heteroatoms selected from O or S; and one to four substituents are independently selected from the group consisting of cyano, $(C_1-C_3)$alkyl, $(C_1-C_3)$alkoxy, $(C_1-C_3)$alkythio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_4)$alkoxycarbonyl, $(C_1-C_3)$alkylaminocarbonyl, and di$(C_1-C_3)$alkylaminocarbonyl;

$R^4$ is selected from unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein one to four substituents are independently selected from the group consisting of cyano, nitro, halo, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfinyl, $(C_1-C_3)$haloalkylsulfinyl, $(C_1-C_3)$alkylsulfonyl, $(C_1-C_3)$haloalkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfinyl$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, and di$(C_1-C_3)$alkylaminocarbonyl;

wherein two adjacent positions on $R^4$ may be joined together with the atoms to which they are attached to form an unsubstituted or substituted, unsaturated, partially unsaturated, or saturated 5-, 6- or 7-membered carbocyclic or heterocyclic ring wherein the heterocyclic ring contains from one to three heteroatoms selected from N, O, or S; and one to four substituents are independently selected from the group consisting of cyano, $(C_1-C_3)$alkyl, $(C_1-C_3)$alkoxy, $(C_1-C_3)$alkythio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_4)$alkoxycarbonyl, $(C_1-C_3)$alkylaminocarbonyl, di$(C_1-C_3)$alkylaminocarbonyl, oxo, and methoxyimino;

$R^5$ is unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, where one to four substituents are independently selected from the group consisting of: cyano, nitro, halo, amino, $(C_1-C_3)$alkyl, $(C_1-C_3)$haloalkyl, $(C_1-C_3)$alkoxy, $(C_1-C_3)$haloalkoxy, $(C_3)$alkenyloxy, $(C_3)$alkynyloxy, $(C_1-C_3)$alkythio, $(C_1-C_3)$haloalkylthio, $(C_3)$alkenylthio, $(C_3)$alkynylthio, $(C_1-C_3)$alkylsulfonyl, $(C_1-C_3)$haloalkylsulfonyl, $(C_1-C_3)$alkylsulfinyl, $(C_1-C_3)$haloalkylsulfinyl $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfinyl$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, and cyano$(C_1-C_3)$alkyl;

wherein two adjacent positions may be joined together with the atoms to which they are attached to form an unsubstituted or substituted, unsaturated, partially unsaturated, or saturated 4-, 5-, 6- or 7-membered carbocyclic or heterocyclic ring, wherein:

the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, di$(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino; and $R^6$ and $R^7$ are independently selected from the group consisting of $(C_1-C_3)$alkyl, $(C_1-C_3)$alkoxy, $(C_1-C_3)$alkylthio, $(C_1-C_3)$alkylamino, di$(C_1-C_3)$alkylamino, and unsubstituted or substituted phenyl, wherein the substituents are from one to four and are independently selected from the group consisting of cyano, nitro, halo, formyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, and cyano$(C_1-C_3)$alkyl, wherein $R^6$ and $R^7$ may be joined together with the phosphorus to which they are attached to form an unsaturated, partially unsaturated, or saturated, unsubstituted or substituted 5- or 6-membered heterocyclic ring wherein the heterocyclic ring contains one phosphorus and from zero to three heteroatoms selected from N, O or S; and from one to four substituents are independently selected from the group consisting of $(C_1-C_3)$alkyl, $(C_1-C_3)$haloalkyl, $(C_1-C_3)$alkoxycarbonyl, $(C_1-C_3)$alkylaminocarbonyl, di$(C_1-C_3)$alkylaminocarbonyl, oxo, and methoxyimino.

Compounds of formula I, II and III are still more preferred when:

$Q^1$ is O, $Q^2$ is S and n=2;

$R^1$ is substituted phenyl wherein one to two substituents are independently selected from the group consisting of ($C_1$-$C_2$)alkyl and ($C_1$-$C_2$)alkoxy;

wherein in said substituted phenyl, two adjacent positions are joined together with the atoms to which they are attached to form an unsubstituted or substituted, unsaturated, partially unsaturated, or saturated 5-, 6- or 7-membered carbocyclic or heterocyclic ring wherein:

the heterocyclic ring contains from one to two oxygen atoms; and one to four substituents are independently selected from the group consisting of: cyano, ($C_1$-$C_2$)alkyl, ($C_1$-$C_2$)alkylamino, di($C_1$-$C_2$)alkylamino, ($C_1$-$C_2$)alkoxycarbonyl, ($C_1$-$C_2$)alkylaminocarbonyl, di($C_1$-$C_2$)alkylaminocarbonyl, oxo, and methoxyimino;

$R^2$ and $R^3$ are independently selected from the group consisting of: ($C_1$-$C_6$)alkyl, ($C_3$-$C_6$)cycloalkyl, halo($C_1$-$C_6$)alkyl, ($C_1$-$C_3$)alkoxy($C_1$-$C_3$)alkyl, ($C_1$-$C_3$)althylthio($C_1$-$C_3$)alkyl, ($C_1$-$C_3$)alkylsulfinyl($C_1$-$C_3$)alkyl, ($C_1$-$C_3$)alkylsulfonyl($C_1$-$C_3$)alkyl, ($C_1$-$C_3$)alkylamino($C_1$-$C_3$)alkyl, di($C_1$-$C_3$)alkylamino($C_1$-$C_3$)alkyl, ($C_1$-$C_6$)alkylcarbonyl, ($C_1$-$C_3$)alkylcarbonyl($C_1$-$C_3$)alkyl, ($C_1$-$C_6$)alkylaminocarbonyl, di($C_1$-$C_6$)alkylaminocarbonyl, ($C_1$-$C_3$)alkylaminocarbonyl($C_1$-$C_3$)alkyl, di($C_1$-$C_3$)alkylaminocarbonyl($C_1$-$C_3$)alkyl, ($C_1$-$C_3$)alkylcarbonylamino($C_1$-$C_3$)alkyl, ($C_1$-$C_6$)alkoxycarbonyl, and $C_1$-$C_3$)alkoxycarbonyl($C_1$-$C_3$)alkyl;

wherein $R^2$ and $R^3$ may be joined together with the carbon to which they are attached to form an unsubstituted or substituted, partially unsaturated or saturated 5-, 6- or 7-membered carbocyclic or heterocyclic ring wherein:

the heterocyclic ring contains one heteroatom selected from O or S; and one to four substituents are independently selected from the group consisting of ($C_1$-$C_3$)alkyl, ($C_1$-$C_3$)alkylamino, di($C_1$-$C_3$)alkylamino, ($C_1$-$C_4$)alkoxycarbonyl, ($C_1$-$C_3$)alkylaminocarbonyl, and di($C_1$-$C_3$)alkylaminocarbonyl;

$R^4$ is selected from unsubstituted or substituted phenyl or pyridyl wherein one to four substituents are independently selected from the group consisting of ($C_1$-$C_3$)alkyl and ($C_1$-$C_3$)alkoxy;

$R^5$ is unsubstituted or substituted phenyl wherein one to two substituents are independently selected from the group consisting of ($C_1$-$C_2$)alkyl and ($C_1$-$C_2$)alkoxy;

wherein two adjacent positions may be joined together with the atoms to which they are attached to form an unsubstituted or substituted, unsaturated, partially unsaturated, or saturated 5-, 6- or 7-membered carbocyclic or heterocyclic ring, wherein:

the heterocyclic ring contains from one to two oxygen atoms; and one to four substituents are independently selected from the group consisting of cyano, ($C_1$-$C_2$)alkyl, ($C_1$-$C_2$)alkylamino, di($C_1$-$C_2$)alkylamino, ($C_1$-$C_2$)alkoxycarbonyl, ($C_1$-$C_2$)alkylaminocarbonyl, di($C_1$-$C_2$)alkylaminocarbonyl, oxo, and methoxyimino; and $R^6$ and $R^7$ taken together with the phosphorus to which they are attached form a saturated, unsubstituted or substituted 5- or 6-membered heterocyclic ring, wherein the heterocyclic ring contains one phosphorus and from one to two heteroatoms selected from N, O or S; and from one to four substituents are independently selected from the group consisting of ($C_1$-$C_3$)alkyl and ($C_1$-$C_3$)haloalkyl.

Compounds of formula I, II and III are most preferred when:

$Q^1$ is O, $Q^2$ is S and n=2;

$R^1$ is selected from the group consisting of 2-methyl-3,4-methylenedioxyphenyl, 2-ethyl-3,4-methylenedioxyphenyl, 2-methyl-3,4-ethylenedioxyphenyl, 2-ethyl-3,4-ethylenedioxyphenyl, 2-methyl-3,4-oxydimethylenephenyl, 2-ethyl-3,4-oxydimethylenephenyl, 2-methyl-3,4-oxytrimethylenephenyl, and 2-ethyl-3,4-oxytrimethylenephenyl;

$R^5$ is selected from the group consisting of 4-ethylphenyl, 3-fluoro4-ethylphenyl, 2-fluoro-4-ethylphenyl, 2,3-dimethylphenyl, 2,3-diethylphenyl, 2-methyl-3-methoxyphenyl, 2-ethyl-3-methoxyphenyl, 2-methyl-3,4-methylenedioxyphenyl, 2-ethyl-3,4-methylenedioxyphenyl, 2-methyl-3,4-ethylenedioxyphenyl, 2-ethyl-3,4-ethylenedioxyphenyl, 2-methyl-3,4-oxydimethylenephenyl, 2-ethyl-3,4-oxydimethylenephenyl, 2-methyl-3,4-oxytrimethylenephenyl, 2-ethyl-3,4-oxytrimethylenephenyl, 2-methyl-3,4-dimethyleneoxyphenyl, 2-ethyl-3,4-dimethyleneoxyphenyl, 2-methyl-3,4-trimethyleneoxyphenyl, and 2-ethyl-3,4-trimethyleneoxyphenyl; and $R^6$ and $R^7$ taken together with the phosphorus to which they are attached form a saturated 6-membered heteocyclic ring, wherein the heterocyclic ring contains one phosphorus and two oxygen atoms, and the two oxygen atoms are joined by three carbon atoms having up to four substituents of ($C_1$-$C_2$)alkyl.

Synthesis

The compounds of the present invention may be made according to the following synthesis routes, which one of ordinary skill in the art will readily recognize.

Method A

Compounds of formula I, II, and III can be prepared from amine compounds of formula IV by reaction with an acid halide or with an acid mediated by a coupling agent. Thus, use of a carboxylic acid chloride $R^1$COCl or $R^1CO_2H$ in combination with a coupling agent such diisopropyl carbodiimide affords compounds of formula I.

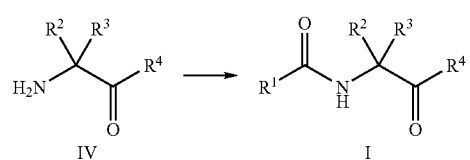

Use of a sulfonyl chloride $R^5SO_2Cl$ affords compounds of formula II

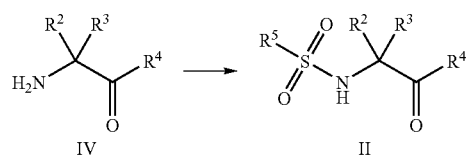

and use of a phosphoryl chloride ($R^6R^7P$(=O)Cl) or thiophosphoryl chloride ($R^6R^7P$(=S)Cl) affords compounds of formula III.

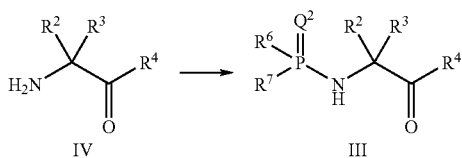

Amine compounds of formula IV are available by various procedures known to those skilled in the art (Larramona C. R. Hebd. Seances Acad. Sci. 1951, 232, 849; Ogata, Y. et al J. Org. Chem. 1977, 42, 4061-4066; Suzuki, M. et al J. Org. Chem. 1973, 38, 3571-3575; Bestmann, H. J.; Kunstmann, R. Chem. Ber. 1969, 102, 1816-1832; Farnum, D. G.; Carlson, G. R. Synthesis 1972, 191-2).

Method B

Alternatively compounds of formula I are prepared from Weinreb amides of formula V and organometallic reagents of formula VI such as Grignard and organolithium reagents.

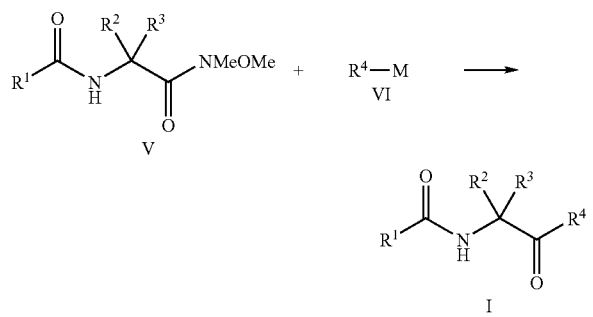

M = e.g. MgBr, MgCl, MgI, Li

Amides V are prepared from azlactones VII following the procedure of Kemp, A.; Ner, S. K.; Rees, L.; Suckling, C. J.; Tedford, M. C.; Bell, A. R.; Wrigglesworth, R. J. Chem. Soc. Perkin Trans. 2 1993, 741-748.

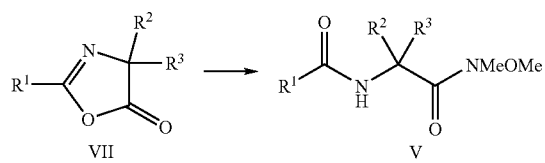

Method C

Furthermore compounds of formula I are prepared from secondary alcohols of formula VIII. This oxidation reaction may be effected by a variety of reagents including Dess-Martin periodinane and pyridinium chlorochromate.

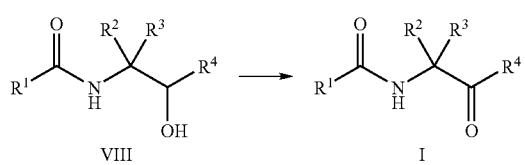

Secondary alcohols VIII are prepared by reaction of aldehydes IX with organometallic reagents VI:

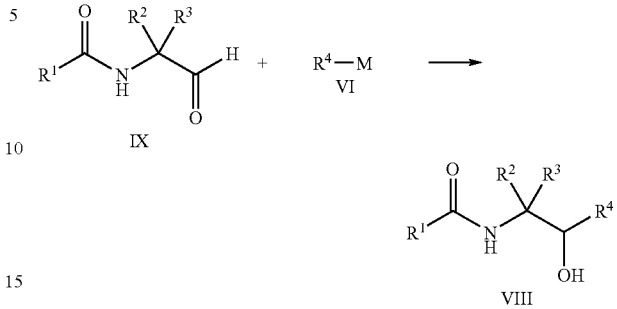

M = e.g. MgBr, MgCl, MgI, Li

Aldehydes IX are prepared by oxidation of primary alcohols X using various oxidizing agents known to those skilled in the art:

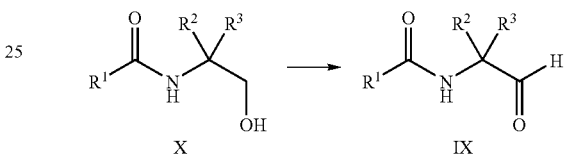

Primary alcohols X are prepared by reduction of azlactones VII in the case when $R^1$=formula II:

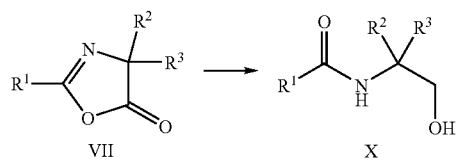

or by reaction of aminoalcohols XI with acid chlorides $R^1COCl$

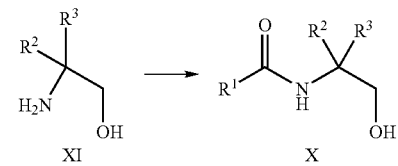

Method D

Furthermore compounds of formula II are prepared from secondary alcohols of formula XII. This oxidation reaction may be effected by a variety of reagents including Dess-Martin periodinane and pyridinium chlorochromate.

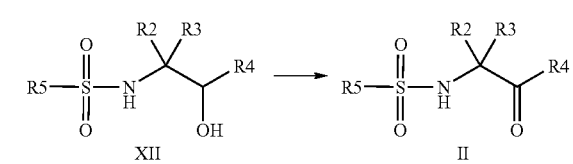

Secondary alcohols XII are prepared by reaction of sulfonyl chlorides with aminoalcohols XIII:

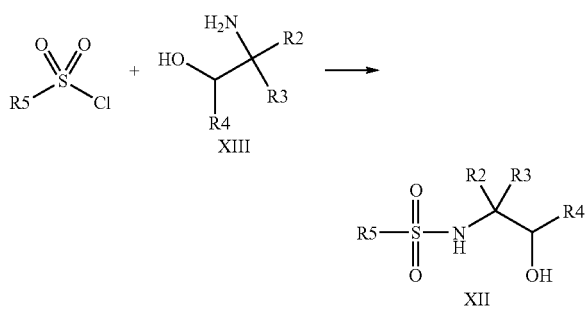

The corresponding reaction of aminoalcohol XIII with an acid chloride affords secondary alcohol VIII:

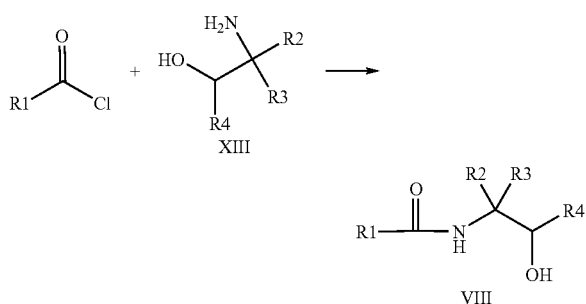

Aminoalcohols XIII are prepared by reduction of nitroalcohols XIV. This reduction reaction may be effected by a variety of reagents including zinc under acidic conditions.

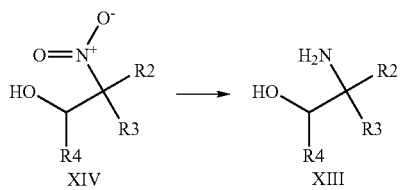

Nitroalcohols XIV are prepared by reaction with aldehydes under basic conditions.

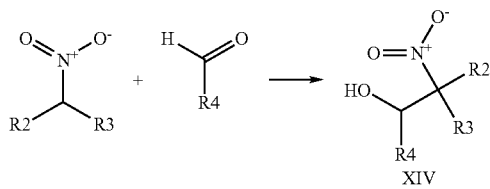

Because the compounds of formula I, II or III may contain a number of optically active carbon atoms, they may exist as enantiomers, diastereomers, stereoisomers, or their mixtures.

The term "alkyl" includes both branched and straight chain alkyl groups. Typical alkyl groups include, for example, methyl, ethyl, n-propyl, isopropyl, n-butyl, sec-butyl, isobutyl, tert-butyl, n-pentyl, isopentyl, n-hexyl, n-heptyl, isooctyl, nonyl, and decyl.

The term "halo" refers to fluoro, chloro, bromo or iodo.

The term "haloalkyl" refers to an alkyl group substituted with one or more halo groups such as, for example, chloromethyl, 2-bromoethyl, 3-iodopropyl, trifluoromethyl, and perfluoropropyl.

The term "cycloalkyl" refers to a cyclic aliphatic ring structure, optionally substituted with alkyl, hydroxy, or halo, such as cyclopropyl, methylcyclopropyl, cyclobutyl, 2-hydroxycyclopentyl, cyclohexyl, and 4-chlorocyclohexyl.

The term "hydroxyalkyl" refers to an alkyl group substituted with one or more hydroxy groups such as, for example, hydroxymethyl and 2,3-dihydroxybutyl.

The term "alkylsulfonyl" refers to a sulfonyl moiety substituted with an alkyl group such as, for example, mesyl, and n-propylsulfonyl.

The term "alkenyl" refers to an ethylenically unsaturated hydrocarbon group, straight or branched chain, having 1 or 2 ethylenic bonds such as, for example, vinyl, allyl, 1-butenyl, 2-butenyl, isopropenyl, and 2-pentenyl.

The term "haloalkenyl" refers to an alkenyl group substituted with one or more halo groups.

The term "alkynyl" refers to an unsaturated hydrocarbon group, straight or branched, having 1 or 2 acetylenic bonds such as, for example, ethynyl and propargyl.

The term "alkylcarbonyl" refers to an alkylketo functionality, for example acetyl, n-butyryl and the like.

The term "flash chromatography" refers to silica gel chromatography performed under air, argon, or nitrogen pressure typically in the range of 10 to 50 psi.

The term "gradient chromatography" refers to silica gel chromatography in which the chemical substance is eluted from a column with a progressively changing composition of a solvent mixture.

The term "Rf" refers to the fractional distance of movement of a chemical substance of interest on a thin layer chromatography plate, relative to the distance of movement of the eluting solvent system.

The terms "Parr hydrogenator" and "Parr shaker" refer to apparatus available from Parr Instrument Company, Moline Ill., which are designed to facilitate vigorous mixing of a solution containing a chemical substance of interest with an optional solid suspended catalyst and a pressurized, contained atmosphere of a reactant gas. Typically, the gas is hydrogen and the catalyst is palladium, platinum, or oxides thereof deposited on small charcoal particles. The hydrogen pressure is typically in the range of 30 to 70 psi.

The term "Dess-Martin reagent" refers to (1,1,1-triacetoxy)-1,1-dihydro-1,2-benziodoxol-3(1H)-one as a solution in dichloromethane available from Acros Organics/Fisher Scientific Company, L.L.C.

The term "PS-NMM" refers to a —$SO_2NH(CH_2)_3$-morpholine functionalized polystyrene resin available from Argonaut Technologies, San Carlos, Calif.

The term "AP-NCO" refers to an isocyante-functionalized resin available from Argonaut Technologies, San Carlos, Calif.

The term "AP-trisamine" refers to a polystyrene-$CH_2NHCH_2CH_2NH(CH_2CH_2NH_2)_2$ available from Argonaut Technologies, San Carlos, Calif.

The term "PS-TsNHNH2 resin" refers to a polystyrene-Ph-S(O)$_2$NHNH$_2$ resin available from Argonaut Technologies, San Carlos, Calif.

The term "hydroxybenzotriazole resin" refers to a hydroxybenzotriazole-modified polystyrene resin; one type is available from Argonaut Technologies, San Carlos, Calif.

The terms "Chem Elute" and "Chem Elute cartridge" refer to a diatomaceous earth solid phase extraction media used for compound purification, available from Varian Inc.

The term "heterocyclyl" or "heterocycle" refers to an unsubstituted or substituted; saturated, partially unsaturated, or unsaturated 5 or 6-membered ring containing one, two or three heteroatoms, preferably one or two heteroatoms independently selected from the group consisting of oxygen, nitrogen and sulfur. Examples of heterocyclyls include, for example, pyridyl, thienyl, furyl, pyrimidinyl, pyrazinyl, quinolinyl, isoquinolinyl, pyrrolyl, indolyl, tetrahydrofuryl, pyrrolidinyl, piperidinyl, tetrahydropyranyl, morpholinyl, piperazinyl, dioxolanyl, and dioxanyl.

The term "alkoxy" includes both branched and straight chain alkyl groups attached to a terminal oxygen atom. Typical alkoxy groups include, for example, methoxy, ethoxy, n-propoxy, isopropoxy, and tert-butoxy.

The term "haloalkoxy" refers to an alkoxy group substituted with one or more halo groups such as, for example chloromethoxy, trifluoromethoxy, difluoromethoxy, and perfluoroisobutoxy.

The term "alkylthio" includes both branched and straight chain alkyl groups attached to a terminal sulfur atom such as, for example methylthio.

The term "haloalkylthio" refers to an alkylthio group substituted with one or more halo groups such as, for example trifluoromethylthio.

The term "alkoxyalkyl" refers to an alkyl group substituted with an alkoxy group such as, for example, isopropoxymethyl.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In a specific embodiment of the invention, polynucleotides are detected by employing hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius for the hybridization step. In a more preferred embodiment, the hybridization conditions comprise 2×SSPE and 63 degrees Celsius for both the hybridization and washing steps.

In one embodiment, the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}P$-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←→) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., 1987, PNAS 84:7413; Mackey, et al., 1988. Proc. Natl. Acad. Sci. U.S.A. 85:8027-8031; and Ulmer et al., 1993, Science 259:1745-1748). The use of cationic lipids may promote encapsulation of negatively charged nucleic acids, and also promote fusion with negatively charged cell membranes (Felgner and Ringold, 1989, Science 337: 387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum. Gene Ther. 3: 147-154; and Wu and Wu, 1987, J. Biol. Chem. 262: 4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease SI), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (see Cherbas L., et. al., (1991), *Genes Dev.* 5, 120-131); AGGTCAN$_{(n)}$AGGTCA,where N$_{(n)}$ can be one or more spacer nucleotides (see D'Avino P P., et. al., (1995), *Mol. Cell. Endocrinol*, 113, 1-9); and GGGTTGAAT-GAATTT (see Antoniewski C., et. al., (1994). Mol. Cell Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in Saccharomyces); AOX1 promoter (useful for expression in Pichia); β-lactamase, lac, ara, tet, trp, lP$_L$, lP$_R$, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (CsVMV), chlorophyll a/b binding protein, ribulose 1, 5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell a-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence.

A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

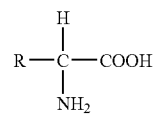

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one (1) wild-type or naturally occurring amino acid with a different amino acid relative to the wild-type or naturally occurring polypeptide. A substitution mutant polypeptide may comprise only one (1) wild-type or naturally occurring amino acid substitution and may be referred to as a "point mutant" or a "single point mutant" polypeptide. Alternatively, a substitution mutant polypeptide may comprise a substitution of two (2) or more wild-type or naturally occurring amino acids with 2 or more amino acids relative to the wild-type or naturally occurring polypeptide. According to the invention, a Group H nuclear receptor ligand binding domain polypeptide comprising a substitution mutation comprises a substitution of at least one (1) wild-type or naturally occurring amino acid with a different amino acid relative to the wild-type or naturally occurring Group H nuclear receptor ligand binding domain polypeptide.

Wherein the substitution mutant polypeptide comprises a substitution of two (2) or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth (20$^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson, C., et al., 1978, J. Biol. Chem. 253: 6551; Zoller and Smith, 1984, DNA 3: 479-488; Oliphant et al., 1986, Gene 44: 177; Hutchinson et al., 1986, Proc. Natl. Acad. Sci. U.S.A. 83: 710), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art.

For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50: 667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol*. 215:403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism. More preferably, the change is at least 5-fold greater. Even more preferably, the change is at least 10-fold greater. Still more preferably, the change is at least 100 fold greater. Even still more preferably, the change is at least 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal". The present invention is useful to search for orthogonal ligands and orthogonal receptor-based gene expression systems such as those described in co-pending U.S. application Ser. No. 09/965,697, which is incorporated herein by reference in its entirety.

The term "modulate" means the ability of a given ligand/receptor complex to induce or suppress the transactivation of an exogenous gene.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. For example, transgenic plants are obtained by regeneration from the transformed cells. Numerous transformation procedures are known from the literature such as agroinfection using *Agrobacterium tumefaciens* or its $T_1$ plasmid, electroporation, microinjection of plant cells and protoplasts, and microprojectile transformation. Complementary techniques are known for transformation of animal cells and regeneration of such transformed cells in transgenic animals. Exogenous genes can be either natural or synthetic genes and therapeutic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject. The term "therapeutic gene" means a gene which imparts a beneficial function to the host cell in which such gene is expressed. Therapeutic genes are not naturally found in host cells.

The term "ecdysone receptor complex" generally refers to a heterodimeric protein complex consisting of two members of the steroid receptor family, ecdysone receptor ("EcR") and ultraspiracle ("USP") proteins (see Yao, T. P.,et. al. (1993) Nature 366,476-479; Yao, T.-P.,et. al., (1992) Cell 71, 63-72). The functional ecdysteroid receptor complex may also include additional protein(s) such as immunophilins. Additional members of the steroid receptor family of proteins, known as transcriptional factors (such as DHR38, betaFTZ-1 or other insect homologs), may also be ligand dependent or independent partners for EcR and/or USP. The ecdysone receptor complex can also be a heterodimer of ecdysone receptor protein and the vertebrate homolog of ultraspiracle protein, retinoic acid-X-receptor ("RXR") protein. Homodimer complexes of the ecdysone receptor protein or USP may also be functional under some circumstances.

An ecdysteroid receptor complex can be activated by an active ecdysteroid or non-steroidal ligand bound to one of the proteins of the complex, inclusive of EcR, but not excluding other proteins of the complex.

The ecdysone receptor complex includes proteins which are members of the steroid receptor superfamily wherein all members are characterized by the presence of an amino-terminal transactivation domain, a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the ecdysone receptor complex may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the ecdysone receptor. As a result, they are insensitive to the ligands of this invention. Thus, the ligands of this invention will have negligible physiological or other effects on transformed cells, or the whole organism. Therefore, cells can grow and express the desired product, substantially unaffected by the presence of the ligand itself.

The term "subject" means an intact plant or animal or a cell from a plant or animal. It is also anticipated that the ligands will work equally well when the subject is a fungus or yeast. When the subject is an intact animal, preferably the animal is a vertebrate, most preferably a mammal.

The ligands of the present invention, when used with the ecdysone receptor complex which in turn is bound to the response element linked to an exogenous gene, provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the ecdysone receptor complex to a specific control, or regulatory, DNA element. The ecdysone receptor protein, like other members of the steroid receptor family, possesses at least three domains, a transactivation domain, a DNA binding domain, and a ligand binding domain. This receptor, like a subset of the steroid receptor family, also possesses less well-defined regions responsible for heterodimerization properties. Binding of the ligand to the ligand binding domain of ecdysone receptor protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g. EcR+EcR or USP+USP). Preferably, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL4 protein from yeast (see Sadowski, et. al. (1988) Nature, 335, 563-564) or LexA protein from *E. coli* (see Brent and Ptashne (1985), Cell, 43, 729-736) to accommodate chimeric ecdysone receptor complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. The term "promoter" means a specific nucleotide sequence recognized by RNA polymerase. The sequence is the site at which transcription can be specifically initiated under proper conditions. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

Another aspect of this invention is a method to modulate the expression of one or more exogenous genes in a subject, comprising administering to the subject an effective amount, that is, the amount required to elicit the desired gene expression or suppression, of a ligand comprising a compound of formula I, II or III and wherein the cells of the subject contain:
  a) an ecdysone receptor complex comprising:
    1) a DNA binding domain;
    2) a binding domain for the ligand; and
    3) a transactivation domain; and
  b) a DNA construct comprising:
    1) the exogenous gene; and
    2) a response element; and wherein:
  i) the exogenous gene is under the control of the response element; and
  ii) binding of the DNA binding domain to the response element in the presence of the ligand results in activation or suppression of the gene.

A related aspect of this invention is a method for regulating endogenous or heterologous gene expression in a transgenic subject comprising contacting a ligand comprising a compound of formula I, II or III with an ecdysone receptor within the cells of the subject wherein the cells contain a DNA binding sequence for the ecdysone receptor and wherein formation of an ecdysone receptor-ligand-DNA binding sequence complex induces expression of the gene.

A fourth aspect of the present invention is a method for producing a polypeptide comprising the steps of:
  a) selecting a cell which is substantially insensitive to exposure to a ligand comprising a compound of formula I, II or III;
  b) introducing into the cell:
    1) a DNA construct comprising:
      a) an exogenous gene encoding the polypeptide; and
      b) a response element;
    wherein the gene is under the control of the response element; and
    2) an ecdysone receptor complex comprising:
      a) a DNA binding domain;
      b) a binding domain for the ligand; and
      c) a transactivation domain; and
  c) exposing the cell to the ligand.

As well as the advantage of temporally controlling polypeptide production by the cell, this aspect of the invention provides a further advantage, in those cases when accumulation of such a polypeptide can damage the cell, in that expression of the polypeptide may be limited to short periods. Such control is particularly important when the exogenous gene is a therapeutic gene. Therapeutic genes may be called upon to produce polypeptides which control needed functions, such as the production of insulin in diabetic patients. They may also be used to produce damaging or even lethal proteins, such as those lethal to cancer cells. Such control may also be important when the protein levels produced may constitute a metabolic drain on growth or reproduction, such as in transgenic plants.

Numerous genomic and cDNA nucleic acid sequences coding for a variety of polypeptides are well known in the art. Exogenous genetic material useful with the ligands of this invention include genes that encode biologically active proteins of interest, such as, for example, secretory proteins that can be released from a cell; enzymes that can metabolize a substrate from a toxic substance to a non-toxic substance, or from an inactive substance to an active substance; regulatory proteins; cell surface receptors; and the like. Useful genes also include genes that encode blood clotting factors, hormones such as insulin, parathyroid hormone, luteinizing hormone releasing factor, alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor, colony stimulating factor-1, tumor necrosis factor, and erythropoietin; genes encoding inhibitor substances such as $alpha_1$-antitrypsin, genes encoding substances that function as drugs such as diphtheria and cholera toxins; and the like. Useful genes also include those useful for cancer therapies and to treat genetic disorders. Those skilled in the art have access to nucleic acid sequence information for virtually all known genes and can either obtain the nucleic acid molecule directly from a public depository, the institution that published the sequence, or employ routine methods to prepare the molecule.

For gene therapy use, the ligands described herein may be taken up in pharmaceutically acceptable carriers, such as, for example, solutions, suspensions, tablets, capsules, ointments, elixirs, and injectable compositions. Pharmaceutical preparations may contain from 0.01% to 99% by weight of the ligand. Preparations may be either in single or multiple dose forms. The amount of ligand in any particular pharmaceutical preparation will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

The ligands described herein may also be administered in conjunction with other pharmaceutically active compounds. It will be understood by those skilled in the art that pharmaceutically active compounds to be used in combination with the ligands described herein will be selected in order to avoid adverse effects on the recipient or undesirable interactions between the compounds. Examples of other pharmaceutically active compounds which may be used in combination with the ligands include, for example, AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflamatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, porphyria agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media. In some cases the ligands may be useful as an adjunct to drug therapy, for example, to "turn off" a gene that produces an enzyme that metabolizes a particular drug.

For agricultural applications, in addition to the applications described above, the ligands of this invention may also be used to control the expression of pesticidal proteins such as *Bacillus thuringiensis* (Bt) toxin. Such expression may be tissue or plant specific. In addition, particularly when control of plant pests is also needed, one or more pesticides may be combined with the ligands described herein, thereby providing additional advantages and effectiveness, including fewer total applications, than if the pesticides are applied separately. When mixtures with pesticides are employed, the relative proportions of each component in the composition will depend upon the relative efficacy and the desired application rate of each pesticide with respect to the crops, pests, and/or weeds to be treated. Those skilled in the art will recognize that mixtures of pesticides may provide advantages such as a broader spectrum of activity than one pesticide used alone. Examples of pesticides which can be combined in compositions with the ligands described herein include fungicides, herbicides, insecticides, miticides, and microbicides.

The ligands described herein can be applied to plant foliage as aqueous sprays by methods commonly employed, such as conventional high-liter hydraulic sprays, low-liter sprays, air-blast, and aerial sprays. The dilution and rate of application will depend upon the type of equipment employed, the method and frequency of application desired, and the ligand application rate. It may be desirable to include additional adjuvants in the spray tank. Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials*, and *McCutcheon's Functional Materials*, all published annually by McCutcheon Division of MC Publishing Company (New Jersey). The ligands can also be mixed with fertilizers or fertilizing materials before their application. The ligands and solid fertilizing material can also be admixed in mixing or blending equipment, or they can be incorporated with fertilizers in granular formulations. Any relative proportion of fertilizer can be used which is suitable for the crops and weeds to be treated. The ligands described herein will commonly comprise from 5% to 50% of the fertilizing composition. These compositions provide fertilizing materials which promote the rapid growth of desired plants, and at the same time control gene expression.

HOST CELLS AND NON-HUMAN ORGANISMS OF THE INVENTION

As described above, ligands for modulating gene expression system of the present invention may be used to modulate gene expression in a host cell. Expression in transgenic host cells may be useful for the expression of various genes of interest. The present invention provides ligands for modulation of gene expression in prokaryotic and eukaryotic host cells. Expression in transgenic host cells is useful for the expression of various polypeptides of interest including but not limited to antigens produced in plants as vaccines, enzymes like alpha-amylase, phytase, glucanes, and xylanse, genes for resistance against insects, nematodes, fungi, bacteria, viruses, and abiotic stresses, antigens, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

Thus, the present invention provides ligands for modulating gene expression in an isolated host cell according to the invention. The host cell may be a bacterial cell, a fungal cell, a nematode cell, an insect cell, a fish cell, a plant cell, an avian cell, an animal cell, or a mammalian cell. In still another embodiment, the invention relates to ligands for modulating gene expression in an host cell, wherein the method comprises culturing the host cell as described above in culture medium under conditions permitting expression of a polynucleotide encoding the nuclear receptor ligand binding domain comprising a substitution mutation, and isolating the nuclear receptor ligand binding domain comprising a substitution mutation from the culture.

In a specific embodiment, the isolated host cell is a prokaryotic host cell or a eukaryotic host cell. In another specific embodiment, the isolated host cell is an invertebrate host cell or a vertebrate host cell. Preferably, the host cell is selected from the group consisting of a bacterial cell, a fungal cell, a yeast cell, a nematode cell, an insect cell, a fish cell, a plant cell, an avian cell, an animal cell, and a mammalian cell. More preferably, the host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell. Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*; plant species selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum,* papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat; animal; and mammalian host cells.

In a specific embodiment, the host cell is a yeast cell selected from the group consisting of a *Saccharomyces,* a *Pichia,* and a *Candida* host cell.

In another specific embodiment, the host cell is a *Caenorhabdus elegans* nematode cell.

In another specific embodiment, the host cell is an insect cell.

In another specific embodiment, the host cell is a plant cell selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum,* papaya, peanut, pea, pepper, pigeonpea, pineapple, *Phaseolus,* potato, pumpkin, rice, sorghum, soybean, squash, sugarcane, sugarbeet, sunflower, sweet potato, tea, tomato, tobacco, watermelon, and wheat cell.

In another specific embodiment, the host cell is a zebrafish cell.

In another specific embodiment, the host cell is a chicken cell.

In another specific embodiment, the host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification [e.g., glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent. The present invention also relates to a non-human organism comprising an isolated host cell according to the invention. In a specific embodiment, the non-human organism is a prokaryotic organism or a eukaryotic organism. In another specific embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In a specific embodiment, the non-human organism is a yeast selected from the group consisting of *Saccharomyces, Pichia,* and *Candida.*

In another specific embodiment, the non-human organism is a *Caenorhabdus elegans* nematode.

In another specific embodiment, the non-human organism is a plant selected from the group consisting of an apple, *Arabidopsis,* bajra, banana, barley, beans, beet, blackgram, chickpea, chili, cucumber, eggplant, favabean, maize, melon, millet, mungbean, oat, okra, *Panicum,* papaya, peanut, pea, pepper, pigeonpea, pineapple, *Phaseolus,* potato, pumpkin, rice, sorghum, soybean, squash, sugarcane, sugarbeet, sunflower, sweet potato, tea, tomato, tobacco, watermelon, and wheat.

In another specific embodiment, the non-human organism is a *Mus musculus* mouse.

Gene Expression Modulation System of the Invention

The present invention relates to a group of ligands that are useful in an ecdysone receptor-based inducible gene expression system. As presented herein, a novel group of ligands provides an improved inducible gene expression system in both prokaryotic and eukaryotic host cells. Thus, the present invention relates to ligands that are useful to modulate expression of genes. In particular, the present invention relates to ligands having the ability to transactivate a gene expression modulation system comprising at least one gene expression cassette that is capable of being expressed in a host cell comprising a polynucleotide that encodes a polypeptide comprising a Group H nuclear receptor ligand binding domain. Preferably, the Group H nuclear receptor ligand binding is from an ecdysone receptor, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor. More preferably, the Group H nuclear receptor ligand binding domain is from an ecdysone receptor.

In a specific embodiment, the gene expression modulation system comprises a gene expression cassette comprising a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a gene expression cassette comprising a) a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation, and b) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a first gene expression cassette comprising a polynucleotide that encodes a first polypeptide comprising a DNA-binding domain that recognizes a response element associated with a gene whose expression is to be modulated and a nuclear receptor ligand binding domain, and a second gene expression cassette comprising a polynucleotide that encodes a second polypeptide comprising a transactivation domain and a nuclear receptor ligand binding domain, wherein one of the nuclear receptor ligand binding domains is a Group H nuclear receptor ligand binding domain comprising a substitution mutation. In a preferred embodiment, the first polypeptide is substantially free of a transactivation domain and the second polypeptide is substantially free of a DNA binding domain. For purposes of the invention, "substantially free" means that the protein in question does not contain a sufficient sequence of the domain in question to provide activation or binding activity. The gene expression modulation system may further comprise a third gene expression cassette comprising: i) a response element recognized by the DNA-binding domain of the first polypeptide of the first gene expression cassette; ii) a promoter that is activated by the transactivation domain of the second polypeptide of the second gene expression cassette; and iii) a gene whose expression is to be modulated.

Wherein when only one nuclear receptor ligand binding domain is a Group H ligand binding domain comprising a substitution mutation, the other nuclear receptor ligand binding domain may be from any other nuclear receptor that forms a dimer with the Group H ligand binding domain comprising the substitution mutation. For example, when the Group H nuclear receptor ligand binding domain comprising a substitution mutation is an ecdysone receptor ligand binding domain comprising a substitution mutation, the other nuclear receptor ligand binding domain ("partner") may be from an ecdysone receptor, a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a USP (see co-pending applications PCT/US01/09050, PCT/US02/05235, and PCT/US02/05706, incorporated herein by reference in their entirety). The "partner" nuclear receptor ligand binding domain may further comprise a truncation mutation, a deletion mutation, a substitution mutation, or another modification.

Preferably, the vertebrate RXR ligand binding domain is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

Preferably, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), a ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

Preferably, the chimeric RXR ligand binding domain comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In a preferred embodiment, the chimeric RXR ligand binding domain comprises at least one vertebrate species RXR polypeptide fragment and one invertebrate species RXR polypeptide fragment.

In a more preferred embodiment, the chimeric RXR ligand binding domain comprises at least one vertebrate species RXR polypeptide fragment and one non-Dipteran/non-Lepidopteran invertebrate species RXR homolog polypeptide fragment.

In a specific embodiment, the gene whose expression is to be modulated is a homologous gene with respect to the host cell. In another specific embodiment, the gene whose expression is to be modulated is a heterologous gene with respect to the host cell.

The ligands for use in the present invention as described below, when combined with the ligand binding domain of the nuclear receptor(s), which in turn are bound to the response element linked to a gene, provide the means for external temporal regulation of expression of the gene. The binding mechanism or the order in which the various components of this invention bind to each other, that is, for example, ligand to ligand binding domain, DNA-binding domain to response element, transactivation domain to promoter, etc., is not critical.

In a specific example, binding of the ligand to the ligand binding domain of a Group H nuclear receptor and its nuclear receptor ligand binding domain partner enables expression or suppression of the gene. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al. (1988) Nature, 335: 563-564) or LexA protein from *Escherichia coli* (see Brent and Ptashne (1985), Cell, 43: 729-736), or synthetic response elements specific for targeted interactions with proteins designed, modified, and selected for such specific interactions (see, for example, Kim, et al. (1997), *Proc. Natl. Acad. Sci., USA*, 94: 3616-3620) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The ecdysone receptor is a member of the nuclear receptor superfamily and classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), orphan receptor 1 (OR-1), steroid hormone nuclear receptor 1 (NER-1), retinoid X receptor interacting protein-15 (RIP-15), liver X receptor β (LXRβ), steroid hormone receptor like protein (RLD-1), liver X receptor (LXR), liver X receptor α (LXRα), farnesoid X receptor (FXR), receptor interacting protein 14 (RIP-14), and farnesol receptor (HRR-1

In particular, described herein are novel ligands useful in gene expression modulation system comprising a Group H nuclear receptor ligand binding domain comprising a substitution mutation. This gene expression system may be a "single switch"-based gene expression system in which the transactivation domain, DNA-binding domain and ligand binding domain are on one encoded polypeptide. Alternatively, the gene expression modulation system may be a "dual switch"- or "two-hybrid"-based gene expression modulation system in which the transactivation domain and DNA-binding domain are located on two different encoded polypeptides.

An ecdysone receptor-based gene expression modulation system of the present invention may be either heterodimeric or homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366, 476-479; Yao, et al., (1992) Cell 71, 63-72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., Curr. Opin. Cell Biol. 9:222-232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al. Mol Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. The EcR receptor, like a subset of the steroid receptor family, also possesses less well-defined regions responsible for heterodimerization properties. Because the domains of nuclear receptors are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. It has previously been shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050).

Method of Modulating Gene Expression of the Invention

The present invention also relates to methods of modulating gene expression in a host cell using a gene expression modulation system according to the invention. Specifically, the present invention provides a method of modulating the expression of a gene in a host cell comprising the steps of: a) introducing into the host cell a gene expression modulation system according to the invention; and b) introducing into the host cell a ligand; wherein the gene to be modulated is a component of a gene expression cassette comprising: i) a response element comprising a domain recognized by the DNA binding domain of the gene expression system; ii) a promoter that is activated by the transactivation domain of the gene expression system; and iii) a gene whose expression is to be modulated, whereby upon introduction of the ligand into the host cell, expression of the gene is modulated.

The invention also provides a method of modulating the expression of a gene in a host cell comprising the steps of: a) introducing into the host cell a gene expression modulation system according to the invention; b) introducing into the host cell a gene expression cassette according to the invention, wherein the gene expression cassette comprises i) a response element comprising a domain recognized by the DNA binding domain from the gene expression system; ii) a promoter that is activated by the transactivation domain of the gene expression system; and iii) a gene whose expression is to be modulated; and c) introducing into the host cell a ligand; whereby upon introduction of the ligand into the host cell, expression of the gene is modulated.

The present invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

Genes of interest for expression in a host cell using methods disclosed hereinmay be endogenous genes or heterologous genes. Nucleic acid or amino acid sequence information for a desired gene or protein can be located in one of many public access databases, for example, GEN-BANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in the methods described herein.

Examples of genes of interest for expression in a host cell using methods set forth herein include, but are not limited to: antigens produced in plants as vaccines, enzymes like alpha-amylase, phytase, glucanes, and xylanse, genes for resistance against insects, nematodes, fungi, bacteria, viruses, and abiotic stresses, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Measuring Gene Expression/Transcription

One useful measurement of the methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of the methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using the present invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybridizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

The present invention may be better understood by reference to the following non-limiting Examples, which are provided as exemplary of the invention.

EXAMPLES

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" program is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "μL" means microliter(s), "mL" means milliliter(s), "L" means liter(s), "μM" means micromolar, "mM" means millimolar, "μg" means microgram(s), "mg" means milligram(s), "A" means adenine or adenosine, "T" means thyrnine or thymidine, "G" means guanine or guanosine, "C" means cytidine or cytosine, "x g" means times gravity, "nt" means nucleotide(s), "aa" means amino acid(s), "bp" means base pair(s), "kb" means kilobase(s), "k" means kilo, "μ" means micro, and "° C." means degrees Celsius.

Example 1

Preparation of Compounds

Example of Method A

Preparation of 5-ethyl-2,3-dihydro-benzo[1,4]dioxine-6-carboxylic acid (1-benzoyl-cyclopentyl)-amide (Compound Example 22)

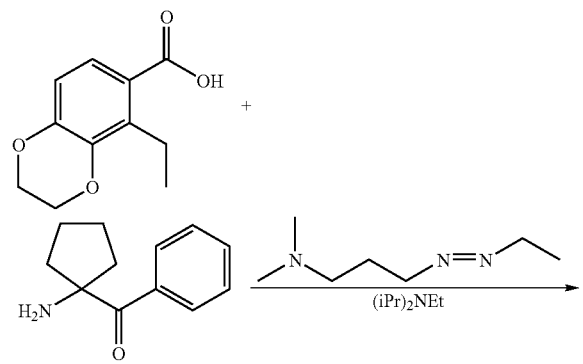

-continued

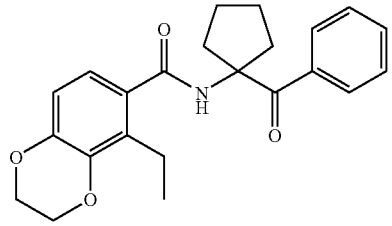

To a stirred solution of crude 1-amino-1-benzoylcyclopentane (500 mg, ~1 mmol based on 40% purity), 2-ethyl-3,4-ethylenbedioxybenzoic acid (220 mg, 1.1 mmol), diisopropylethylamine (416 μL, 2.3 mmol) and 4-dimethylaminopyridine (12 mg, 0.1 mmol) in $CH_2Cl_2$ (3 mL) was added N-(3-(dimethylamino)propyl)-N'-ethylcarbodiimide (222 mg, 1.16 mmol). The mixture was stirred over the weekend. A 20 mL Chem Elut cartridge was pre-wetted with 5% aqueous HCl (8 mL) and the reaction mixture was added. The cartridge was eluted with ether (25 mL). A second 20 mL Chem Elut cartridge was pre-wetted with saturated aqueous $NaHCO_3$ and the ether eluate was added to it and collected. The eluate was evaporated to dryness to leave an oil which was applied to a 5 g silica cartridge, prewetted with hexanes. The cartridge was eluted sequentially with 0, 10, 25, 50, 75 and 100% ether in hexanes (20 mL of each) and six fractions were collected. Fractions 5 and 6 were combined to afford 5-ethyl-2,3-dihydro-benzo[1,4]dioxine-6-carboxylic acid (1-benzoyl-cyclopentyl)-amide (compound 22, 131 mg). $^1H$ NMR ($CDCl_3$) δ(ppm): 0.88 (t, 3H, J=7.4 Hz), 1.81 (m, 4H), 2.03 (m, 2H), 2.25 (q, J=7.4 Hz), 2H), 2.55 (m, 2H), 4.18 (s, 4H), 6.43 (d, J=8.4 Hz, 1H), 6.74 (s, 1H), 7.40 (m, 3H), 7.85 (m, 2H); $^{13}C$ NMR ($CDCl_3$) δ14.6, 19.5, 24.9, 37.4, 53.4, 64.0, 64.1, 70.7, 114.2, 119.3, 127.8, 128.2, 128.8, 131.4, 132.1, 136.6, 141.4, 144,5, 168.8, 201.4.

Example of Method B

Preparation of 5-(3-methoxy-2-methyl-phenyl)-6-oxa-4-aza-spiro[2.4]hept-4-en-7-one (VII, $R^1$=2-Me-3-MeO-Ph, $R^2=R^3$=—$(CH_2)_2$—)

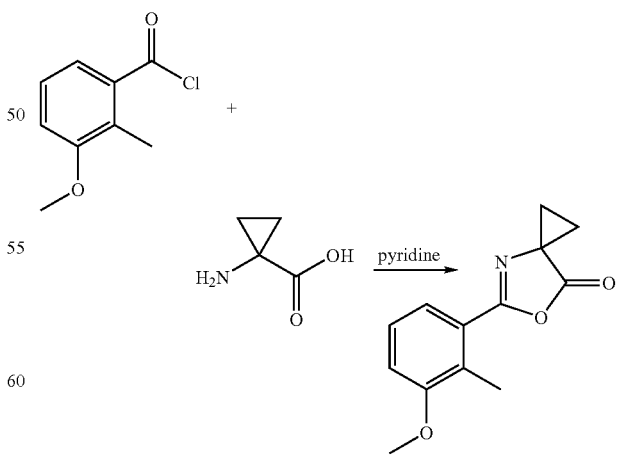

To a stirred solution of 1-aminocyclopropanecarboxylic acid (1.06 g, 10.5 mmol) in pyridine (20 mL) cooled to ~5° C., solid 3-methoxy-2-methylbenzoyl chloride (4.35 g, 23.6 mmol) was added. The mixture was stirred at room temperature for 1 week and evaporated under reduced pressure to leave an oily solid. This material was taken up in 20% ether in hexanes (175 mL), washed with water (50 mL), 5% aqueous HCl (2×50 mL) and saturated aqueous NaHCO$_3$ (50 mL). The organic layer was dried over MgSO$_4$ and evaporated under reduced pressure to leave 5-(3-methoxy-2-methyl-phenyl)-6-oxa4-aza-spiro[2.4]hept-4-en-7-one (1.90 g) as a yellow solid. $^1$H NMR (CDCl$_3$) δ(ppm): 1.80 (m, 2H), 1.90 (m, 2H), 2.49 (s, 3H), 3.85 (s, 3H), 7.01 (d, 1H), 7.22 (t, 1H), 7.40 (d, 1H).

Preparation of 3-methoxy-N-[1-(methoxy-methyl-carbamoyl)-cyclopropyl]-2-methyl-benzamide, R$^1$=2-Me-3-MeO—Ph, R$^2$=R$^3$=—(CH$_2$)$_2$—

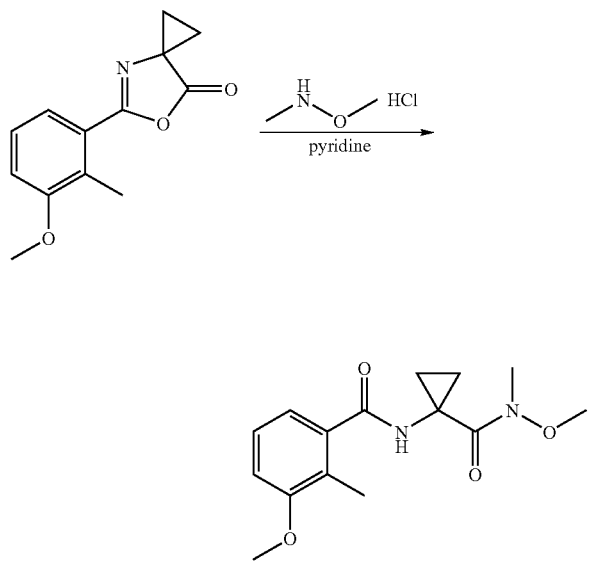

A mixture of 5-(3-methoxy-2-methyl-phenyl)-6-oxa-4-aza-spiro[2.4]hept-4-en-7-one (VII, R$^1$=2-Me-3-MeO—Ph, R$^2$=R$^3$=—(CH$_2$)$_2$—, 1.90 g, 8.2 mmol), N,O-dimethylhydroxylamine hydrochloride (0.96 g, 9.9 mmol), pyridine (0.80 mL, 9.9 mmol) and methylene chloride (30 mL) was stirred at room temperature for 1 week. The mixture was diluted with ethyl acetate (150 mL), washed with 5% aqueous HCl (2×50 mL) and saturated aqueous NaHCO$_3$ (2×50 mL), and dried. Removal of the solvent afforded a crude product (2.54 g) as a syrup. The crude product was purified by flash chromatography on a silica gel (75 g) column eluted sequentially with 0, 20, 40, 60, 80, 100% ether in hexanes (200 mL of each) and ethyl acetate (500 mL) to afford 3-methoxy-N-[1-(methoxy-methyl -carbamoyl)-cyclopropyl]-2-methyl-benzamide (1.67 g, 69%) as a white solid, mp 173-175° C. $^1$H NMR (CDCl$_3$) δ(ppm): 1.15 (m, 2H), 1.53 (m, 2H), 2.23 (s, 3H), 3.22 (s, 3H), 3.69 (s, 3H), 3.82 (s, 3H), 6.67 (s, 1H), 6.86 (d, J=7.9 Hz, 1H), 6.90 (d, J=7.9 Hz, 1H), 7.13 (t, J=7.9 Hz, 1H); $^{13}$C NMR (CDCl$_3$) δ12.3, 15.1, 33.6, 35.1, 55.6, 61.0, 111.4, 118.6, 124.9, 126.5, 137.4, 157.9, 170.3, 170.9. Calculated for C$_{15}$H$_{20}$N$_2$O$_4$: C, 61.63; H, 6.90; N, 9.58. Found: C, 61.24; H, 6.75; N, 9.30.

Preparation of N-[1-(3,5-dimethyl-benzoyl)-cyclopropyl]-3-methoxy-2-methyl-benzamide (Compound Example 13)

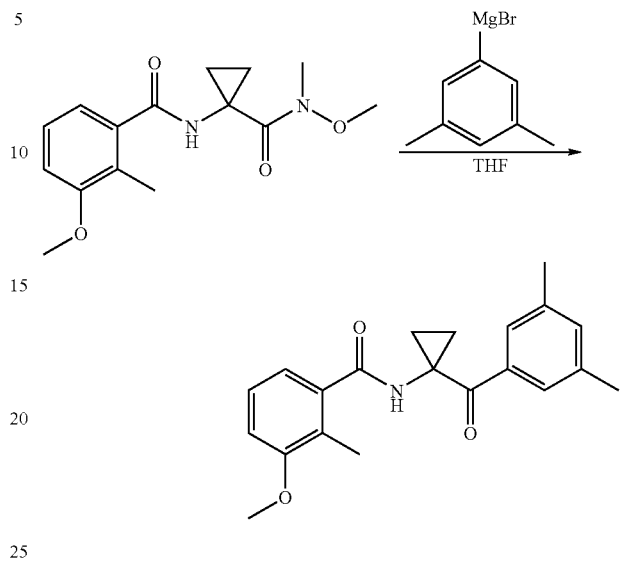

A round-bottom flask was flushed with dry N$_2$ and charged with a stirbar and 3-methoxy-N-[1-(methoxy-methyl-carbamoyl)-cyclopropyl]-2-methyl-benzamide (V, R$^1$=2-Me-3-MeO—Ph, R$^2$=R$^3$=—(CH$_2$)$_2$, 73 mg, 0.25 mmol) and 3,5-dimethylphenylmagnesium bromide (1M in THF, 1 mL, 1.0 mmol) was added. The mixture was allowed to stir for 5 h and poured into stirred saturated aqueous NaHCO$_3$ (6 mL). The mixture was added to a 20 mL Chem Elut cartridge and allowed to stand for 5 min. The cartridge was eluted with CH$_2$Cl$_2$ (25 mL). The eluate was evaporated to dryness to afford crude product (67 mg) as a solid.

The crude product was applied to a 2 g silica cartridge and eluted with 25, 50 and 75% ethyl acetate in hexanes (10 mL of each) and ethyl acetate (3×10 mL) and six fractions were collected. Fractions 2, 3 and 4 were combined to afford N-[1-(3,5-dimethyl-benzoyl)-cyclopropyl]-3-methoxy-2-methyl-benzamide 13 (58 mg) as a white solid, mp 174-176° C. $^1$H NMR (CDCl$_3$) δ(ppm): 1.31 (m, 2H), 1.83 (m, 2H), 1.93 (s, 3H), 2.32 (s, 6H), 3.79 (s, 3H), 6.47 (s, 1H), 6.56 (d, J=7.9 Hz, 1H), 6.81 (d, J=7.9 Hz, 1H), 7.06 (d, J=7.9 Hz, 1H), 7.10 (s, 1H), 7.33 (s, 2H); $^{13}$C NMR (CDCl$_3$) δ(ppm): 11.9, 18.6, 21.2, 40.7, 55.6, 111.4, 118.1, 123.5, 125.1, 126.4, 133.1, 137.1, 137.7, 138.0, 157.9, 170.4, 202.3.

Example of Method C

Preparation of 4-isopropyl-2-(3-methoxy-2-methyl-phenyl)-4-methyl-4H-oxazol-5-one (VII. R$^1$=2-Me-3-MeO—Ph, R$^2$=i-Pr, R$^3$=Me)

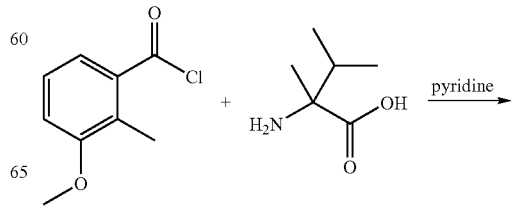

-continued

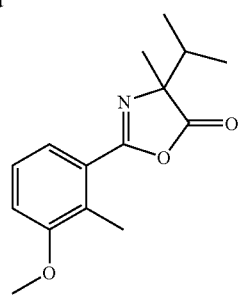

To a stirred suspension of α-methylvaline (2.62 g, 20 mmol) in pyridine (40 nmL) cooled to ~5° C. was added solid 3-methoxy-2-benzoyl chloride (8.31 g, 45 mmol). The mixture was allowed to warm to room temperature and stirred for 1 week. Pyridine was removed by rotary evaporation and the residue was taken up in ether (150 mL) and water (50 mL). The organic layer was separated, washed with 5% aqueous HCl (50 mL) and saturated aqueous NaHCO$_3$ (50 mL), and dried over MgSO$_4$. Removal of the solvent left 4-isopropyl-2-(3-methoxy-2-methyl-phenyl)-4-methyl-4H-oxazol-5-one (6.41 g) as an oily solid. $^1$H NMR (CDCl$_3$) δ(ppm): 0.97 (d, J=6.6 Hz, 3H), 1.09 (d, J=6.6 Hz, 3H), 1.51 (s, 3H), 2.12 (m, 1H), 2.50 (s, 3H), 3.85 (s, 3H), 7.02 (m, 1H), 7.24 (m, 1H), 7.40 (m, 1H).

Preparation of N-(1-hydroxymethyl-1,2-dimethyl-propyl)-3-methoxy-2-methyl-benzamide (X, R$^1$=2-Me-3-MeO—Ph, R$^2$=i-Pr, R$^3$=Me)

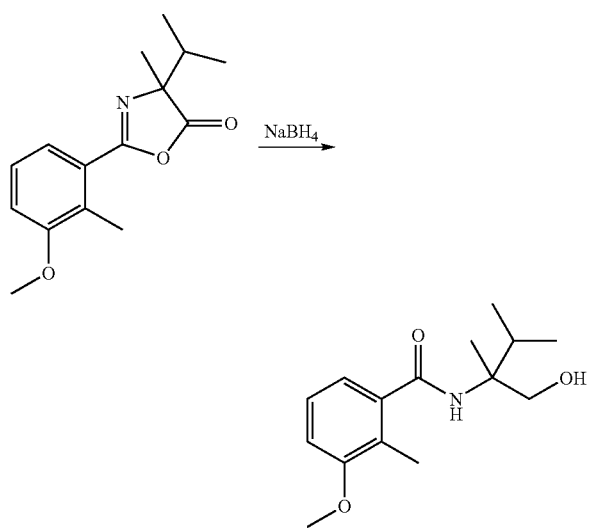

To a stirred solution of 4-isopropyl-2-(3-methoxy-2-methyl-phenyl)-4-methyl-4H-oxazol-5-one (VII, R$^1$=2-Me-3-MeO—Ph, R$^2$=i-Pr, R$^3$=Me, 1.76 g, 6.7 mmol) in THF (30 mL) at temperature was added solid sodium borohydride (0.15 g, 4.0 mmol). The mixture was stirred for 16 h and evaporated under reduced pressure to dryness. Removal of the solvent left a white glassy solid which was taken up in CH$_2$Cl$_2$ (150 mL), washed with 1% aqueous HCl (50 mL) and saturated aqueous NaHCO$_3$ (50 mL) and dried. Removal of the solvent left N-(1-hydroxymethyl-1,2-dimethyl-propyl)-3-methoxy-2-methyl-benzamide (1.25 g) as a white solid. Mp 142-145° C. $^1$H NMR (CDCl$_3$) δ(ppm): 0.97 (d, J=6.6 Hz, 3H), 0.98 (d, J=6.6 Hz, 3H), 1.11 (s, 3H), 2.26 (s, 3H), 2.50 (m, 1H), 3.75 (m, 2H), 3.84 (s, 3H), 5.39 (br s, 1H), 5.83 (br s, 1H), 6.90 (m, 2H), 7.18 (m, 1H); $^{13}$C NMR (CDCl$_3$) δ12.4, 16.8, 17.0, 18.3, 31.1, 55.5, 62.4, 68.1, 111.2, 118.1, 124.0, 126.6, 138.2, 157.9, 171.3.

Preparation of N-(1-formyl-1,2-dimethyl-propyl)-3-methoxy-2-methyl-benzamide (IX, R$^1$=2-Me-3-MeO—Ph. R$^2$=i-Pr, R$^3$=Me)

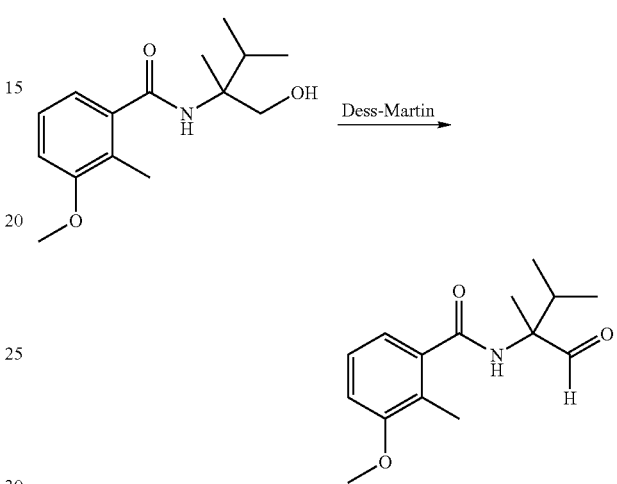

To a stirred solution of N-(1-hydroxymethyl-1,2-dimethyl-propyl)-3-methoxy-2-methyl-benzamide (X, R$^1$=2-Me-3-MeO—Ph, R$^2$=i-Pr, R$^3$=Me, 285 mg, 1.1 mmol) in CH$_2$Cl$_2$ (10 mL) at room temperature was added Dess-Martin periodinane solution (15% by weight, 2.4 mL, ca. 1.1 mmol). The mixture was stirred at room temperature for 4 h and poured into saturated aqueous NaHCO$_3$ (50 mL). Solid Na$_2$S$_2$O$_3$ (2.13 g, 8.6 mmol) was added and the mixture was stirred for 0.5 h. The mixture was extracted with ether (150 mL). The ether extract was washed with saturated aqueous NaHCO$_3$ (50 mL), dried and evaporated under reduced pressure to afford N-(1-formyl-1,2-dimethyl-propyl)-3-methoxy-2-methyl-benzamide (293 mg) as an oil. $^1$H NMR (CDCl$_3$) δ(ppm): 0.98 (d, J=6.6 Hz, 3H), 1.04 (d, J=6.6 Hz, 3H), 1.51 (s, 3H), 2.27 (s, 3H), 2.29 (m, 1H), 3.84 (s, 3H), 6.30 (br s, 1H), 6.91 (m, 1H), 6.96 (m, 1H), 7.18 (m, 1H), 9.60 (s, 1H).

Preparation of N-[1,2-dimethyl-1-(3-methyl-benzoyl)-propyl]-3-methoxy-2-methyl-benzamide (Compound Example 31)

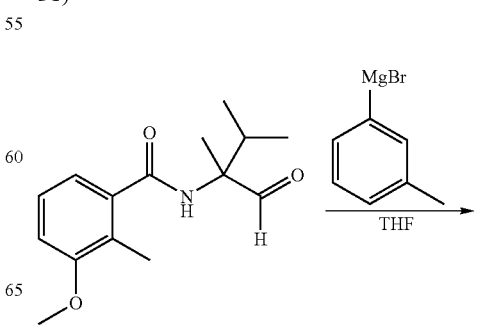

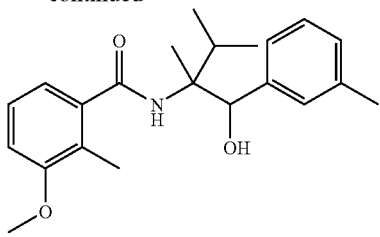

An oven-dried vial equipped with a stir bar was flushed with N₂, charged with N-(1-formyl-1,2-dimethyl-propyl)-3-methoxy-2-methyl-benzamide (IX, R¹=2-Me-3-MeO—Ph, R²=i-Pr, R³=Me, 131 mg, 0.5 mmol) in dry THF (1 mL) and cooled in dry ice acetone. 3-methylphenyl-magnesium bromide (1.0 M, 2 mL, 2.0 mmol) was added and the mixture was stirred at room temperature for 2 hours. The reaction was quenched by addition of saturated aqueous NaHCO₃ (5 mL) and poured onto a 10 mL Chem Elut cartridge. After 5 min the cartridge was eluted with CH₂Cl₂ (25 mL). The eluate was evaporated to leave a secondary alcohol, N-[1-(hydroxy-m-tolyl-methyl)-1,2-dimethyl-propyl]-3-methoxy-2-methyl-benzamide (VIII, R¹=2-Me-3-MeO—Ph, R²=i-Pr, R³=Me, R⁴=3-Me—Ph, 180 mg). ¹H and ¹³C NMR showed complete consumption of aldehyde.

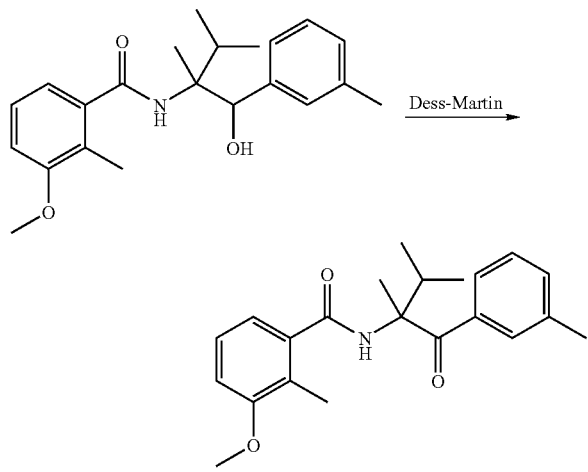

To a stirred solution of crude N-[1-(hydroxy-m-tolyl-methyl)-1,2-dimethyl-propyl]-3-methoxy-2-methyl-benzamide, VIII, in CH₂Cl₂ (2 mL) was added Dess-Martin periodinane (1.4 mL, 15% wt in CH₂Cl₂, 0.65 mmol). The mixture was stirred at room temperature for 6 h, diluted with saturated aqueous NaHCO₃ (5 mL) and treated with solid Na₂S₂O₃ (~1 g, 6.3 mmol). The mixture was stirred for 0.5 h, added to a 10 g Chem Elut cartridge, allowed to stand for 5 min and eluted with CH₂Cl₂ (20 mL). The eluate was evaporated to leave crude ketone 1 (95 mg). The crude ketone was taken up in CH₂Cl₂ (4 mL), treated with PS-TsNHNH₂ resin (0.20 g, 2.9 mmol/g, 0.58 mmol) and allowed to stand for 6 h. The mixture was filtered and washed with CH₂Cl₂ and ether. The eluate was evaporated to leave a solid which was fractionated on a 2 g silica cartridge eluted sequentially with 0, 25, 50 and 75% ether in hexanes (10 mL of each) and ether (2×10 mL). The fourth fraction (75% ether in hexanes) contained N-[1,2-dimethyl-1-(3-methyl-benzoyl)-propyl]-3-methoxy-2-methyl-benzamide 31 (27 mg) as an off-white solid. ¹H NMR (CDCl₃) δ(ppm): 0.94 (d, J=6.8 Hz, 3H), 1.09 (d, J=6.7 Hz, 3H), 1.67 (s, 3H), 2.01 (s, 3H), 2.37 (s, 3H), 2.50 (m, 1H), 6.36 (br s, 1H), 6.76 (d, J=7.6 Hz, 1H), 6.84 (d, J=8.1 Hz, 1H), 7.12 (m, 1H), 7.40 (m, 2H), 7.78 (m, 2H).

Example of Method D

Preparation of (3,5-dichloro-phenyl)-(1-nitro-cyclohexyl)-methanol (XIV)

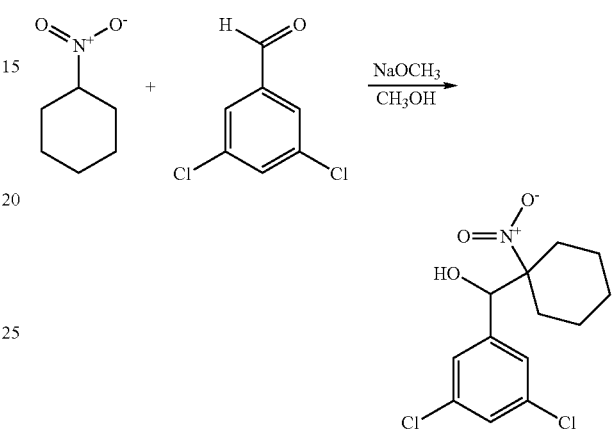

25% sodium methoxide solution (24.9 mmol, 5.7 mL) was diluted with methanol (40 mL), cooled in an ice bath, and nitrocyclohexane was added dropwise over 10 min. The mixture was stirred for 30 min, cooled in an ice bath, and solid 3,5-dichlorobenzaldehyde was added. The mixture was stirred over the weekend, recooled in an ice bath, and treated with 2 mL of glacial acetic acid. The mixture was poured into water (125 mL) and extracted with ether (2×75 mL). The combined ether extracts were washed with water (100 mL) and dried over MgSO₄. Removal of the solvent left crude (3,5-dichloro-phenyl)-(1-nitro-cyclohexyl)-methanol (8.93 g) as a yellow oil. Flash chromatography on silica gel, eluting with a 0-100% ether in hexanes gradient provided product of increased purity (ca. 70%). ¹H NMR (500 MHz, CDCl₃) δ(ppm): 7.35 (s, 1H), 7.19 (s, 2H), 4.90 (s, 1H), 0.9-1.8 (m, 10H).

Preparation of (1-amino-cyclohexyl)-(3,5-dichloro-phenyl)-methanol (XIII)

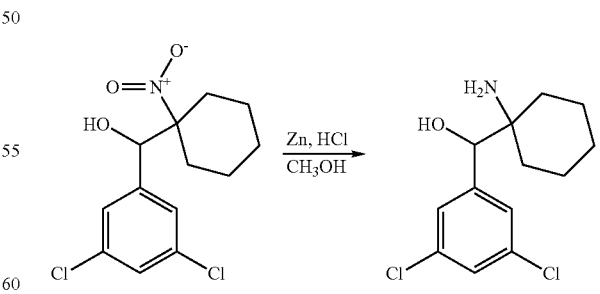

To a stirred solution of (3,5-dichloro-phenyl)-(1-nitro-cyclohexyl)-methanol (5.87 g, 19.3 mmol) in methanol (40 mL) and concentrated HCl (10 mL), cooled to ~5° C., was added zinc powder. The mixture was stirred at room temperature overnight and filtered through Celite. The filter cake was washed with methanol (2×100 mL) and the filtrate was evaporated to dryness. The residue was treated with 5% aqueous NaOH (100 mL) and extracted with ethyl acetate (2×200 mL). The combined organic extracts were dried over $Na_2SO_4$ and evaporated to leave (1-amino-cyclohexyl)-(3,5-dichloro-phenyl)-methanol (4.36 g) as a white solid. $^1H$ NMR (500 MHz, $CDCl_3$) δ(ppm): 7.25 (s, 1H), 7.185 (s, 2H), 4.21 (s, 1H), 1.55 (m, 4H), 1.3 (m, 3H), 1.1 (m, 3H).

Preparation of N-[1-[(3,5-dichloro-phenyl)-hydroxy-methyl]-cyclohexyl]-4-methyl-benzenesulfonamide (XII)

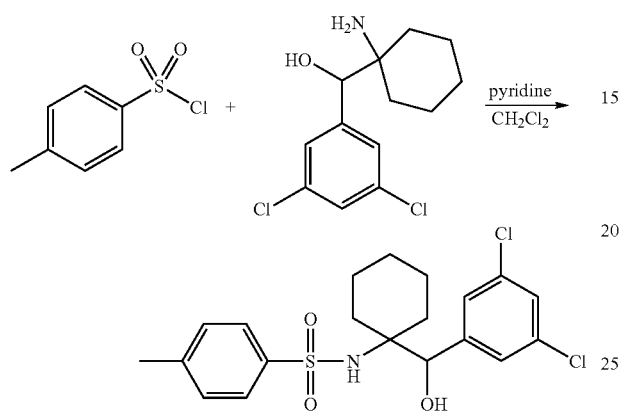

To a stirred solution of (1-amino-cyclohexyl)-(3,5-dichloro-phenyl)-methanol and pyridine (100 μL, 1.24 mmol) in $CH_2Cl_2$ (4 mL) was added p-toluenesulfonyl chloride. The mixture was heated at ca. 35° C. for 8 hours. The mixture was applied to a 10 mL Chem Elut cartridge pre-wetted with 5% aqueous HCl (5 mL) and eluted with $CH_2Cl_2$ (25 mL). The eluate was applied to a second Chem Elut cartridge pre-wetted with saturated aqueous $NaHCO_3$. The eluate from the second cartridge was evaporated to leave N-{1-[(3,5-dichloro-phenyl)-hydroxy-methyl]-cyclohexyl}-4-methyl-benzenesulfonamide (139 mg) as an oil. $^1H$ NMR (500 MHz, $CDCl_3$) δ(ppm): 7.7 (d, 2H), 7.2 (s, 2H), 7.15 (d, 2H), 7.1 (s, 1H), 4.82 (s, 1H), 4.16 (s, 1H), 2.33 (s, 3H), 0.9-1.9 (m, 10H).

Preparation of N-[1-(3,5-dichloro-benzoyl)-cyclohexyl]-4-methyl-benzenesulfonamide (II)

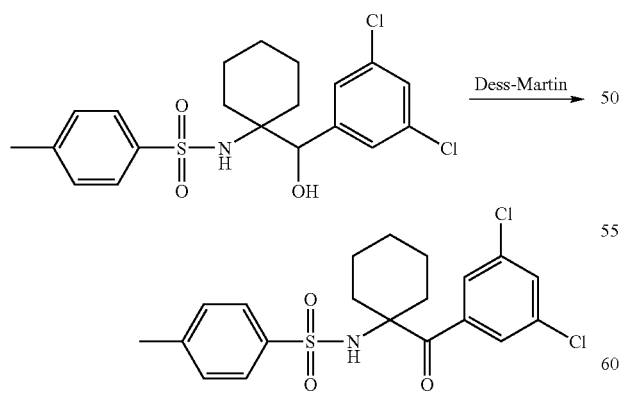

To a stirred solution of N-{1-[(3,5-dichloro-phenyl)-hydroxy-methyl]-cyclohexyl}4-methyl-benzenesulfonamide in $CH_2Cl_2$ (4 mL) was added Dess-Martin reagent. The mixture was stirred for 6 hours and saturated aqueous $NaHCO_3$ (5 mL) and solid $Na_2S_2O_3$ (ca. 1 g) were added. After stirring for 30 min, the mixture was applied to a 10 mL Chem Elut cartridge and allowed to stand for 5 min. The cartridge was eluted with $CH_2Cl_2$ (25 mL) and the eluate was evaporated to leave the intended ketone (102 mg) as an oil. The crude product was dissolved in $CH_2Cl_2$ (4 mL) and stirred with PS-TsNHNH$_2$ resin (100 mg, 0.28 mmol) for 3 hours. The mixture was filtered and washed with $CH_2Cl_2$ (5 mL), ether (5 mL), and $CH_2Cl_2$ (5 mL). The filtrate was evaporated to leave N-[1-(3,5-dichloro-benzoyl)-cyclohexyl]4-methyl-benzenesulfonamide (98 mg) as an oil. $^1H$ NMR (500 MHz, $CDCl_3$) δ(ppm): 7.8 (s, 2H), 7.6 (d, 2H), 7.4 (s, 1H), 7.2 (d, 2H), 5.75 (s, 1H), 2.35 (s, 3H), 1.9 (m, 2H), 1.8 (m, 2H), 1.4 (m, 3H), 1.3 (m, 2H), 1.2 (m, 1H).

Miscellaneous Methods

Preparation of [1-(methoxy-methyl-carbamoyl)-1-methyl-ethyl]-carbamic acid tert-butyl ester

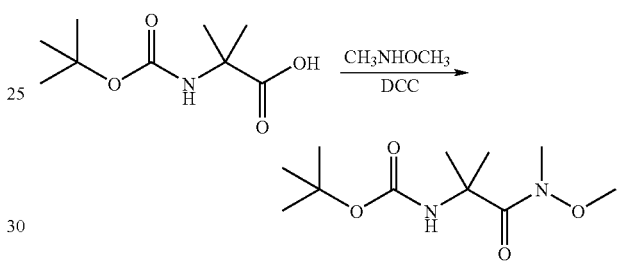

To a stirred mixture of Boc-Aib-OH (5 g, 24.61 mmol, 1 eq), MeNHOMe.HCl (2.88 g, 29.53 mmol, 1.2 eq), DMAP (3.61 g, 29.53 mmol, 1.2 eq), i-Pr$_2$NEt (5.02 mL, 29.53 mmol, 1.2 eq) and $CH_2Cl_2$ (100 mL) was added DCC (6.09 g, 29.53 mmol, 1.2 eq). The mixture was stirred at room temperature for 5 days. The mixture was filtered to remove precipitated N,N'-dicyclohexylurea and the filtrate was evaporated under reduced pressure. The residue was dissolved in ethyl acetate (200 mL), washed with 10% aqueous citric acid (3×200 mL), 10% aqueous NaHCO$_3$ (3×200 mL) and saturated aqueous sodium chloride (3×200 mL), and dried over MgSO$_4$. Removal of the solvent yeided the crude product which was purified by column chromatography (hexane/ethyl acetate 60:40) to afford [1-(methoxy-methyl-carbamoyl)-1-methyl-ethyl]-carbamic acid tert-butyl ester (4.85 g, 80%) as a white solid. $^1H$ NMR (200 MHz, $CDCl_3$) δ(ppm): 1.43 (s, 6H), 1.58 (s, 9H), 3.22 (s, 3H), 3.69 (s, 3H), 6.95 (bs, 1H). MS (ESI, +ve ion): m/z 247.2 (M+1)$^+$.

Preparation of 2-amino-N-methoxy-2,N-dimethyl-propionamide

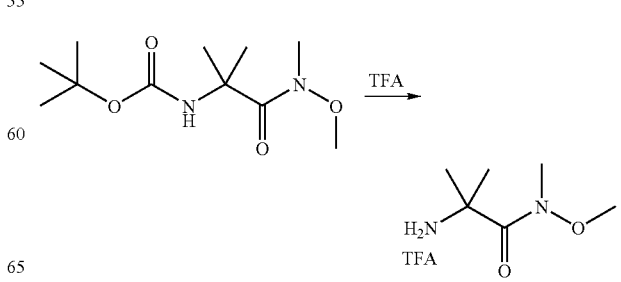

The Boc-protected Weinreb amide, [1-(methoxy-methyl-carbamoyl)-1-methyl-ethyl]-carbamic acid tert-butyl ester, (1.1 g, 4.47 mmol), was taken up in TFA/CH$_2$Cl$_2$ (1:1, 50 mL) and stirred for 20 min. Removal of the solvent left 2-amino-N-methoxy-2,N-dimethyl-propionamide (1.15 g, 99%, quantitative yield) as its TFA salt. $^1$H NMR (200 MHz, CD$_3$OD) δ(ppm): 1.63 (s, 6H), 3.25 (s, 3H), 3.78 (s, 3H). MS (ESI, positive ion): mz/z 147.3 (M+1)$^+$.

Preparation of N-(1,1-dimethyl-2-oxo-butyl)-benzamide

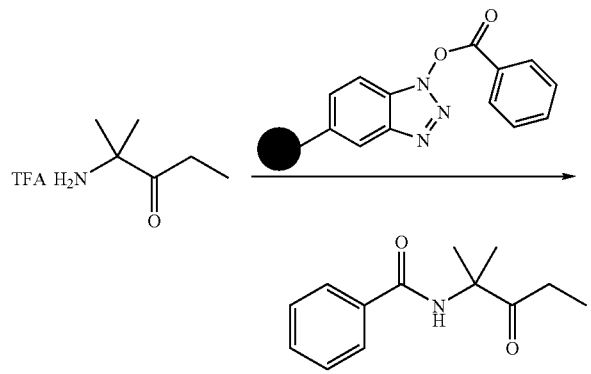

Hydroxybenzotriazole resin (0.107 g, 0.196 mmol) was treated with benzoic acid (0.12 g, 0.982 mmol, 5 eq), DIC (0.152 mL, 0.982 mmol, 5 eq) and DMAP (0.024 g, 0.196 mmol, 1 eq) in DMF-CH$_2$Cl$_2$ (1:1) and shaken for 5 h. The mixture was filtered and the resin was washed with DMF (10×5 mL) and CH$_2$Cl$_2$ (10×5 mL) to give resin-supported benzoic acid benzotriazol-1-yl ester. To a suspension of the resin-ester (0.196 mmol, 1.5 eq) in CH$_2$Cl$_2$ (2 mL) were added i-Pr$_2$NEt (0.033 mL, 0.196 mmol, 1.5 eq) and 2-amino-2-methyl-pentan-3-one (0.03 g, 0.131 mmol, 1 eq). The mixture was agitated for 16 h and filtered. The filtrate was shaken with a weakly basic ion exchange resin Amberlite IRA-95 (1 g, 4.7 mmol g$^{-1}$, 25 eq) for 16 h to remove benzoic acid present in the solution and filtered. The filtrate was eluted through a short column of silica gel (hexane/ethyl acetate 50:50) to remove the unreacted amine. The organic solvent was evaporated to leave N-(1,1-dimethyl-2-oxo-butyl)-benzamide (0.03 g, 87%) as a white solid. $^1$H NMR (200 MHz, CDCl$_3$) δ(ppm): 1.14 (t, J=7.2 Hz, 3H), 1.57 (s, 6H), 2.63 (q, J=7 Hz, 2H), 7.21 (bs, 1H), 7.38-7.56 (aromatic H's, 3H), 7.79 (dd, J=8, 1.8 Hz, 2H). MS (ESI, positive ion): mz/z 220.2 (M+1)$^+$.

Preparation of N-[4-(3,5-dimethyl-benzoyl)-piperidin-4-yl]-3-methoxy-2-methyl-benzamide

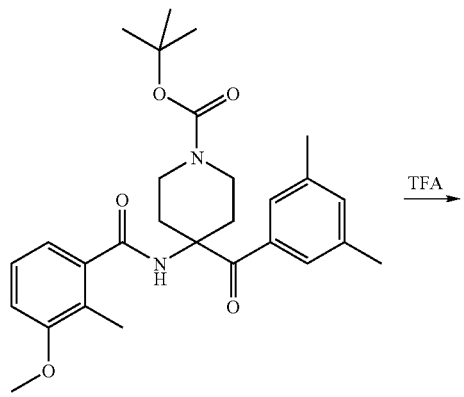

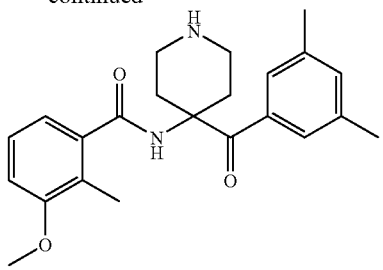

A solution of 4-(3,5-dimethyl-benzoyl)-4-(3-methoxy-2-methyl-benzoylamino)-piperidine-1-carboxylic acid tert-butyl ester in CH$_2$Cl$_2$ and trifluoroacetic acid (20 mL) was stirred at room temperature for 2 hours. The solvent was removed on a rotary evaporator, and the residue was partitioned between ether (150 mL) and saturated aqueous NaHCO$_3$ (50 mL). Significant amounts of undissolved solid were present. The ether layer was dried over MgSO$_4$ and evaporated to leave N-[4-(3,5-dimethyl-benzoyl)-piperidin-4-yl]-3-methoxy-2-methyl-benzamide (0.50 g) as a solid. Additional product (0.11 g) was obtained by extraction and concentration of the aqueous layer with CH$_2$Cl$_2$ (2×50 mL). $^1$H NMR (500 MHz, CDCl$_3$) δ(ppm): 7.55 (s, 2H), 7.12 (m, 2H), 6.87 (d, 1H), 6.77 (d, 1H), 6.65 (br, 1H), 3.8 (s, 3H), 3.1 (br, 2H), 2.95 (br, 2H), 2.3 (s, 6H), 2.25 (br s, 4H), 1.94 (s, 3H).

Preparation of N-[1-acetyl-4-(3,5-dimethyl-benzoyl)-piperidin-4-yl]-3-methoxy-2-methyl-benzamide

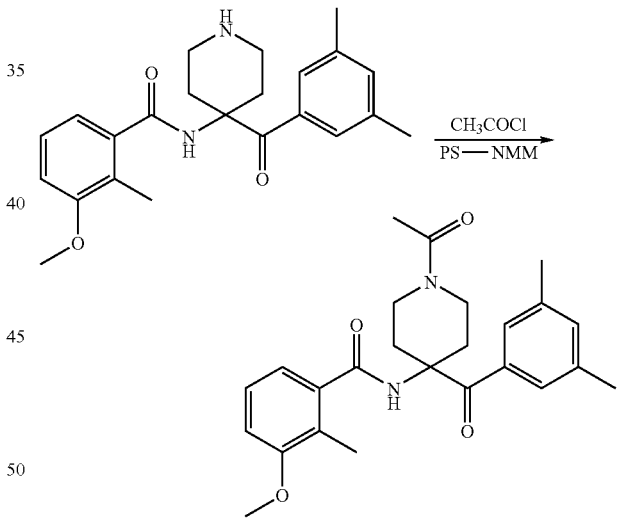

A 25 mL vial was charged with a magnetic stir bar and morpholinomethylpolystyrene (PS-NMM, ~300 mg, 1.92 mmol/g, 0.6 mmol). A solution of N-[4-(3,5-dimethyl-benzoyl)-piperidin-4-yl]-3-methoxy-2-methyl-benzamide (76 mg, 0.2 mmol in 2 mL CH$_2$Cl$_2$) was added, followed by acetyl chloride (16 μL, 0.22 mmol). The mixture was stirred for 2 days, filtered, and fractionated on a 2 g silica gel cartridge, eluting with a 0-100% ethyl acetate in hexanes gradient to provide N-[1-acetyl-4-(3,5-dimethyl-benzoyl)-piperidin-4-yl]-3-methoxy-2-methyl-benzamide. $^1$H NMR (500 MHz, CDCl$_3$) δ(ppm): 7.6 (s, 2H), 7.15 (m, 2H), 6.87 (d, 2H), 6.7 (d, 1H), 4.17 (dt, 1H), 3.8 (s, 3H), 3.78 (m, 1H), 3.45 (t, 1H), 3.25 (t, 1H), 2.5 (m, 1H), 2.35 (m, 1H), 2.32 (s, 6H), 2.2 (m, 1H), 2.17 (m, 1H), 2.05 (s, 3H), 1.92 (s, 3H).

Some related $R^2/R^3$ derivatizations were performed with morpholinopropyl-modified silica gel as base; excess alkylating or acylating agent was removed with diamine-modified silica gel.

TABLE 1

Compounds of Formula I Prepared

| Compound Example | Q | $R^1$ | $R^2$ | $R^3$ | $R^4$ | Method |
|---|---|---|---|---|---|---|
| 1 | O | 2-Me-3-MeO-Ph | —(CH$_2$)$_4$— | | Ph | A |
| 2 | O | 2-Me-3-MeO-Ph | —(CH$_2$)$_4$— | | 3-Me-Ph | B |
| 3 | O | 4-Et-Ph | —(CH$_2$)$_4$— | | Ph | A |
| 4 | O | 2-Me-3-MeO-Ph | —(CH$_2$)$_5$— | | 3-MeO-Ph | B |
| 5 | O | 2-Me-3-MeO-Ph | —(CH$_2$)$_4$— | | 3-MeO-Ph | B |
| 6 | O | 2-Me-3-MeO-Ph | —(CH$_2$)$_3$— | | 3-Me-Ph | B |
| 7 | O | 2-Me-3-MeO-Ph | —(CH$_2$)$_5$— | | 3-Me-Ph | B |
| 8 | O | 2-Me-3-MeO-Ph | Bn | Me | 3-Me-Ph | B |
| 9 | O | 2-Me-3-MeO-Ph | —(CH$_2$)$_2$— | | 3-Me-Ph | B |
| 10 | O | 2-Me-3-MeO-Ph | —(CH$_2$)$_4$— | | 3,5-diMe-Ph | B |
| 11 | O | 2-Me-3-MeO-Ph | —(CH$_2$)$_5$— | | 3,5-diMe-Ph | B |
| 12 | O | 2-Me-3-MeO-Ph | Bn | Me | 3,5-diMe-Ph | B |
| 13 | O | 2-Me-3-MeO-Ph | —(CH$_2$)$_2$— | | 3,5-diMe-Ph | B |
| 14 | O | 2-Me-3-MeO-Ph | —(CH$_2$)$_3$— | | 3,5-diMe-Ph | B |
| 15 | O | 2-Me-3-MeO-Ph | —(CH$_2$)$_5$— | | 4-Me-Ph | B |
| 16 | O | 2-Me-3-MeO-Ph | Bn | Me | 4-Me-Ph | B |
| 17 | O | 2-Me-3-MeO-Ph | —(CH$_2$)$_4$— | | 3-Me-4-F-Ph | B |
| 18 | O | 2-Me-3-MeO-Ph | —(CH$_2$)$_5$— | | 3-Me-4-F-Ph | B |
| 19 | O | 2-Me-3-MeO-Ph | —(CH$_2$)$_2$— | | 3-Me-4-F-Ph | B |
| 20 | O | 2-Me-3-MeO-Ph | i-Pr | Me | 3,5-diMe-Ph | C |
| 21 | O | 2-Et-3-MeO-Ph | —(CH$_2$)$_4$— | | Ph | A |
| 22 | O | 2-Et-3,6-OCH$_2$CH$_2$O-Ph | —(CH$_2$)$_4$— | | Ph | A |
| 23 | O | 2-Me-3,4-OCH$_2$O-Ph | —(CH$_2$)$_4$— | | Ph | A |
| 24 | O | 2-Me-3-MeO-Ph | —(CH$_2$)$_2$— | | 4-Me-Ph | B |
| 25 | O | 2-Me-3-MeO-Ph | —CH$_2$CH$_2$OCH$_2$CH$_2$— | | 3-Me-Ph | B |
| 26 | O | 2-Me-3-MeO-Ph | —CH$_2$CH$_2$SCH$_2$CH$_2$— | | 3-Me-Ph | B |
| 27 | O | 2-Me-3-MeO-Ph | —CH$_2$CH$_2$OCH$_2$CH$_2$— | | 3,5-diMe-Ph | B |
| 28 | O | 2-Me-3-MeO-Ph | —CH$_2$CH$_2$SCH$_2$CH$_2$— | | 3,5-diMe-Ph | B |
| 29 | O | 2-Me-3-MeO-Ph | —CH$_2$CH$_2$C(OCH$_2$CH$_2$O)CH$_2$CH$_2$— | | 3,5-diMe-Ph | B |
| 30 | O | 2-Me-3-MeO-Ph | i-Pr | Me | 2-MeO-Ph | C |
| 31 | O | 2-Me-3-MeO-Ph | i-Pr | Me | 3-Me-Ph | C |
| 32 | O | 2-Me-3-MeO-Ph | i-Pr | Me | 3-MeO-Ph | C |
| 33 | O | 2-Me-3-MeO-Ph | i-Pr | Me | 4-Me-Ph | C |
| 34 | O | 2-Me-3-MeO-Ph | i-Pr | Me | Ph | C |
| 35 | O | 2-Me-3-MeO-Ph | —CH$_2$CH$_2$C(OCH$_2$CH$_2$O)CH$_2$CH$_2$— | | 3-Me-Ph | B |
| 36 | O | 2-Me-3-MeO-Ph | Et | Et | 2-Me-Ph | C |
| 37 | O | 2-Me-3-MeO-Ph | Et | Et | 2-MeO-Ph | C |
| 38 | O | 2-Me-3-MeO-Ph | Et | Et | 4-F-ph | C |
| 39 | O | 2-Me-3-MeO-Ph | —(CH$_2$)$_4$— | | 2-Me-Ph | C |
| 40 | O | 2-Me-3-MeO-Ph | —(CH$_2$)$_4$— | | 2-MeO-Ph | C |
| 41 | O | 2-Me-3-MeO-Ph | —(CH$_2$)$_4$— | | 4-MeO-Ph | C |
| 42 | O | 2-Me-3-MeO-Ph | —(CH$_2$)$_4$— | | 4-F-Ph | C |
| 43 | O | 2-Me-3-MeO-Ph | —(CH$_2$)$_4$— | | 3,4-OCH$_2$O-Ph | C |
| 44 | O | 2-Me-3-MeO-Ph | —(CH$_2$)$_5$— | | 2-Me-Ph | C |
| 45 | O | 2-Me-3-MeO-Ph | —(CH$_2$)$_5$— | | 2-MeO-Ph | C |
| 46 | O | 2-Me-3-MeO-Ph | —(CH$_2$)$_5$— | | 4-MeO-Ph | C |
| 47 | O | 2-Me-3-MeO-Ph | —(CH$_2$)$_5$— | | 3,4-OCH$_2$O-Ph | C |
| 48 | O | 2-Me-3-MeO-Ph | Et | Et | 3-Me-Ph | C |
| 49 | O | 2-Me-3-MeO-Ph | Et | Et | 3-MeO-Ph | C |
| 50 | O | 2-Me-3-MeO-Ph | Et | Et | 3-Me-4-F-Ph | C |
| 51 | O | 2-Me-3-MeO-Ph | Et | Et | 3,5-diMe-Ph | C |
| 52 | O | 2-Me-3-MeO-Ph | i-Bu | Me | 3-Me-Ph | C |
| 53 | O | 2-Me-3-MeO-Ph | i-Bu | Me | 3-MeO-Ph | C |
| 54 | O | 2-Me-3-MeO-Ph | i-Bu | Me | 3-Me-4-F-Ph | C |
| 55 | O | 2-Me-3-MeO-Ph | i-Bu | Me | 3,5-diMe-Ph | C |
| 56 | O | 2-Me-3-MeO-Ph | i-Pr | Me | 3-Me-4-F-Ph | C |
| 57 | O | 2-Me-3-MeO-Ph | Ph | i-Pr | 3-Me-Ph | C |
| 58 | O | 2-Me-3-MeO-Ph | Et | Et | 4-MeO-Ph | C |
| 59 | O | 2-Me-3-MeO-Ph | Et | Et | 3,4-OCH2O-Ph | C |
| 60 | O | 2-Me-3-MeO-Ph | —(CH$_2$)$_5$— | | 4-F-Ph | C |
| 61 | O | 2-Me-3-MeO-Ph | —CH$_2$CH$_2$C(=O)CH$_2$CH$_2$— | | 3-Me-Ph | C |
| 62 | O | 2-Me-3-MeO-Ph | —CH$_2$CH$_2$S(=O)CH$_2$CH$_2$— | | 3,5-diMe-Ph | C |
| 63 | O | 2-Me-3-MeO-Ph | i-Pr | Me | 2-Me-Ph | C |
| 64 | O | 2-Me-3-MeO-Ph | —(CH$_2$)$_5$— | | 2,6-diMeO-3-pyridyl | C |

TABLE 1-continued

Compounds of Formula I Prepared

| Compound Example | Q | R¹ | R² | R³ | R⁴ | Method |
|---|---|---|---|---|---|---|
| 65 | O | 2-Me-3-MeO-Ph | —(CH$_2$)$_4$— | | 3,5-diMeO-4-Me-Ph | C |
| 66 | O | 2-Me-3-MeO-Ph | —(CH$_2$)$_5$— | | 3,5-diMeO-4-Me-Ph | C |
| 67 | O | 2-Me-3-MeO-Ph | —(CH$_2$)$_4$— | | 3-MeO-4,5-diF-Ph | C |
| 68 | O | 2-Me-3-MeO-Ph | —(CH$_2$)$_5$— | | 3-MeO-4,5-diF-Ph | C |
| 69 | O | 2-Me-3-MeO-Ph | —(CH$_2$)$_5$— | | Ph | C |
| 70 | O | 2-Me-3-MeO-Ph | —(CH$_2$)$_6$— | | 2-MeO-Ph | C |
| 71 | O | 2-Me-3-MeO-Ph | —(CH$_2$)$_6$— | | 3,5-diMe-Ph | C |
| 72 | O | 2-Me-3-MeO-Ph | 4-F-Ph | Me | 2-MeO-Ph | C |
| 73 | O | 2-Me-3-MeO-Ph | 4-F-Ph | Me | 3,5-diMe-Ph | C |
| 74 | O | 2-Me-3-MeO-Ph | Me | Me | 2-MeO-Ph | C |
| 75 | O | 2-Me-3-MeO-Ph | Me | Me | 3,5-diMe-Ph | C |
| 76 | O | 2-Me-3-MeO-Ph | Me | Me | Ph | C |
| 77 | O | 2-Me-3-MeO-Ph | Et | Et | 4-Me-Ph | C |
| 78 | O | 2-Me-3-MeO-Ph | Et | Et | Ph | C |
| 79 | O | 2-Me-3-MeO-Ph | —(CH$_2$)$_4$— | | 4-Me-Ph | C |
| 80 | O | 2-Et-3,4-OCH$_2$CH$_2$O-Ph | —(CH$_2$)$_5$— | | 3,5-di-Me-Ph | A |
| 81 | O | 2-Me-3,4-OCH$_2$CH$_2$O-Ph | —(CH$_2$)$_5$— | | 3,5-di-Me-Ph | A |
| 82 | O | 3,4-OCH$_2$CH$_2$O-Ph | —(CH$_2$)$_5$— | | 3,5-di-Me-Ph | A |
| 83 | O | 3,4-CH$_2$OCH$_2$O-Ph | —(CH$_2$)$_5$— | | 3,5-di-Me-Ph | A |
| 84 | O | 2-Et-3,4-OCH$_2$CH$_2$O-Ph | —(CH$_2$)$_4$— | | 3,5-di-Me-Ph | A |
| 85 | O | 2-Me-3,4-OCH$_2$CH$_2$O-Ph | —(CH$_2$)$_4$— | | 3,5-di-Me-Ph | A |
| 86 | O | 3,4-OCH$_2$CH$_2$O-Ph | —(CH$_2$)$_4$— | | 3,5-di-Me-Ph | A |
| 87 | O | 3,4-CH$_2$OCH$_2$O-Ph | —(CH$_2$)$_4$— | | 3,5-di-Me-Ph | A |
| 88 | O | 3,4-OCH$_2$O-Ph | | (CH$_2$)$_4$ | 3,5-di-Me-Ph | A |
| 89 | O | 2-Me-Ph | | (CH$_2$)$_4$ | 3,5-di-Me-Ph | A |
| 90 | O | Ph | t-Bu | H | 4-Cl-Ph | |
| 91 | O | 4-Cl-Ph | | (CH$_2$)$_4$ | Ph | |
| 92 | O | Me | Ph | H | 4-Me-Ph | |
| 93 | O | Me | 4-Me-Ph | H | Ph | |
| 94 | O | Me | Ph | H | Ph | |
| 95 | O | 4-Cl-Ph | Me | Me | Ph | |
| 96 | O | 4-Me-Ph | t-Bu | H | Ph | |
| 97 | O | 2,3-di-Me-Ph | t-Bu | H | Ph | |
| 98 | O | 4-NO$_2$-Ph | t-Bu | H | Ph | |
| 99 | O | 2-Me-3-MeO-Ph | | (CH$_2$)$_2$ | 3-MeO-Ph | |
| 100 | O | 2-Me-3-MeO-Ph | Benzyl | Me | 3-MeO-Ph | |
| 101 | O | 2-Me-3-MeO-Ph | | (CH$_2$)$_2$ | 2-Me-Ph | |
| 102 | O | 3-Me-benzofuran-2-yl | | (CH$_2$)$_4$ | Ph | |
| 103 | O | 2,7-dimethyl-[1,2,4]triazolo[1,5-a] pyrimidine-6-yl | | (CH$_2$)$_4$ | Ph | |
| 104 | O | Ph | Me | Me | Ph | |
| 105 | O | 2-Me-Ph | Me | Me | Ph | |
| 106 | O | 3,4-OCH$_2$O-Ph | Me | Me | Ph | |
| 107 | O | 3-MeO-Ph | Me | Me | Ph | |
| 108 | O | 4-Et-Ph | Me | Me | Ph | |
| 109 | O | 2-Me-3-MeO-Ph | | —CH$_2$CH$_2$N(C(O)OtBu)CH$_2$CH$_2$— | 3-Me-Ph | |
| 110 | O | 2-Me-3-MeO-Ph | | —CH$_2$CH$_2$N(C(O)OtBu)CH$_2$CH$_2$— | 3,5-di-Me-Ph | C |
| 111 | O | 2-Me-3-MeO-Ph | i-Pr | Me | 3,4-OCH$_2$O-Ph | |
| 112 | O | 2-Me-3-MeO-Ph | i-Pr | Me | Me | |
| 113 | O | 2-Me-3-MeO-Ph | t-Bu | H | 3-Me-Ph | C |
| 114 | O | 2-Me-3-MeO-Ph | t-Bu | H | 3-MeO-Ph | C |
| 115 | O | 2-Me-3-MeO-Ph | t-Bu | H | 3,5-di-Me-Ph | C |
| 116 | O | 2-MeO-Ph | Me | Me | 3-Me-Ph | C |
| 117 | O | 2-MeO-Ph | Me | Me | 3-MeO-Ph | C |
| 118 | O | 2-Me-3-MeO-Ph | i-Bu | Me | 4-MeO-Ph | C |
| 119 | O | 2-MeO-Ph | Me | Me | 3,5-di-Me-Ph | |
| 120 | O | 2-Me-3-MeO-Ph | | (CH$_2$)$_5$ | n-Bu | |
| 121 | O | Ph | Me | Me | Et | |
| 122 | O | 3-MeO-Ph | Me | Me | Et | |
| 123 | O | 3,4-OCH$_2$O-Ph | Me | Me | Et | |
| 124 | O | 2-Me-Ph | Me | Me | Et | |
| 125 | O | 4-Et-Ph | Me | Me | Et | |
| 126 | O | Ph | Me | Me | 3,5-di-Me-Ph | |
| 127 | O | 2-Me-Ph | Me | Me | 3,5-di-Me-Ph | |
| 128 | O | 3-MeO-Ph | Me | Me | 3,5-di-Me-Ph | |
| 129 | O | 4-Et-Ph | Me | Me | 3,5-di-Me-Ph | |
| 130 | O | 3,4-OCH$_2$O-Ph | Me | Me | 3,5-di-Me-Ph | |
| 131 | O | Ph | | (CH$_2$)$_4$ | Et | |
| 132 | O | 2-Me-Ph | | (CH$_2$)$_4$ | Et | |
| 133 | O | 3-MeO-Ph | | (CH$_2$)$_4$ | Et | |

TABLE 1-continued

Compounds of Formula I Prepared

| Compound Example | Q | R¹ | R² | R³ | R⁴ | Method |
|---|---|---|---|---|---|---|
| 134 | O | 4-Et-Ph | | (CH₂)₄ | Et | |
| 135 | O | 3,4-OCH₂O-Ph | | (CH₂)₄ | Et | |
| 136 | O | Ph | | (CH₂)₄ | 3,5-di-Me-Ph | |
| 137 | O | 3-MeO-Ph | | (CH₂)₄ | 3,5-di-Me-Ph | |
| 138 | O | 4-Et-Ph | | (CH₂)₄ | 3,5-di-Me-Ph | |
| 139 | O | Ph | | (CH₂)₄ | Ph | |
| 140 | O | 2-Me-Ph | | (CH₂)₄ | Ph | |
| 141 | O | 3-MeO-Ph | | (CH₂)₄ | Ph | |
| 142 | O | 3,4-OCH₂O-Ph | | (CH₂)₄ | Ph | |
| 143 | O | 2-Et-3-MeO-Ph | | (CH₂)₅ | 3,5-di-Me-Ph | A/C/misc |
| 144 | O | 2-Et-3-MeO-Ph | | (CH₂)₄ | 3,5-di-Me-Ph | A/C/misc |
| 145 | O | CF₃ | | (CH₂)₄ | 3,5-di-Me-Ph | A/C/misc |
| 146 | O | 2-Me-3-MeO-Ph | | —CH₂N[(C=O)Ot-Bu]CH₂CH₂CH₂— | 3,5-di-Me-Ph | C |
| 147 | O | 2-Me-3-MeO-Ph | | —CH₂CH₂NHCH₂CH₂— | 3,5-di-Me-Ph | C/misc |
| 148 | O | 2-Me-3-MeO-Ph | | —CH₂NHCH₂CH₂CH₂— | 3,5-di-Me-Ph | C/misc |
| 149 | O | 2-Me-3-MeO-Ph | | —CH₂CH₂N[(C=O)CH₃]CH₂CH₂— | 3,5-di-Me-Ph | C/misc |
| 150 | O | 2-Me-3-MeO-Ph | | —CH₂CH₂N[(C=O)(C=O)OEt]CH₂CH₂— | 3,5-di-Me-Ph | C/misc |
| 151 | O | 2-Me-3-MeO-Ph | | —CH₂CH₂N[S(O)₂CH₃]CH₂CH₂— | 3,5-di-Me-Ph | C/misc |
| 152 | O | 2-Me-3-MeO-Ph | | —CH₂CH₂N[CH₂(C=O)OEt]CH₂CH₂— | 3,5-di-Me-Ph | C/misc |
| 153 | O | 2-Me-3-MeO-Ph | | —CH₂N[(C=O)CH₃]CH₂CH₂CH₂— | 3,5-di-Me-Ph | C/misc |
| 154 | O | 2-Me-3-MeO-Ph | | —CH₂N[(C=O)(C=O)OEt]CH₂CH₂CH₂— | 3,5-di-Me-Ph | C/misc |
| 155 | O | 2-Me-3-MeO-Ph | | —CH₂N[S(O)₂CH₃]CH₂CH₂CH₂— | 3,5-di-Me-Ph | C/misc |
| 156 | O | 2-Me-3-MeO-Ph | | —CH₂N[(CH₂(C=O)OCH₃]CH₂CH₂CH₂— | 3,5-di-Me-Ph | C/misc |
| 157 | O | 2-Me-3-MeO-Ph | | —CH₂CH₂N[(C=O)NHEt]CH₂CH₂— | 3,5-di-Me-Ph | C/misc |
| 158 | O | 2-Me-3-MeO-Ph | | —CH₂CH₂N[(C=O)OiPr]CH₂CH₂— | 3,5-di-Me-Ph | C/misc |
| 159 | O | 2-Me-3-MeO-Ph | | —CH₂CH₂N[CH₂CN]CH₂CH₂— | 3,5-di-Me-Ph | C/misc |
| 160 | O | 2-Me-3-MeO-Ph | | —CH₂N[(C=O)NHEt]CH₂CH₂CH₂—CH₂— | 3,5-di-Me-Ph | C/misc |
| 161 | O | 2-Me-3-MeO-Ph | | —CH₂CH₂CH₂N(CH₃)CH₂— | 3,5-di-Me-Ph | C/misc |
| 162 | O | 2-NH₂-Ph | Et | H | Ph | |
| 163 | O | 4-Et-Ph | | (CH₂)₅ | 3,5-di-Cl-Ph | D |
| 164 | O | 2-Me-3-MeO-Ph | | (CH₂)₅ | 2-MeO-5-F-Ph | C |
| 165 | O | 2-Me-3-MeO-Ph | | (CH₂)₅ | 2-MeO-5-Me-Ph | C |
| 166 | O | 2-Me-3-MeO-Ph | | (CH₂)₅ | 2,5-di-MeO-Ph | C |
| 167 | O | 2-Me-3-MeO-Ph | | (CH₂)₅ | 4-Me-2-pyridyl | C |
| 168 | O | 2-Me-3-MeO-Ph | | (CH₂)₅ | 6-Me-2-pyridyl | C |
| 169 | O | 4-Et-Ph | | (CH₂)₅ | 2-MeO-5-F-Ph | C |
| 170 | O | 4-Et-Ph | | (CH₂)₅ | 2-MeO-5-Me-Ph | C |
| 171 | O | 4-Et-Ph | | (CH₂)₅ | 2,5-di-MeO-Ph | C |
| 172 | O | 4-Et-Ph | | (CH₂)₅ | 4-Me-2-pyridyl | C |
| 173 | O | 4-Et-Ph | | (CH₂)₅ | 6-Me-2-pyridyl | C |
| 174 | O | 4-Et-Ph | | (CH₂)₅ | 2-MeO-Ph | C |
| 175 | O | 4-Et-Ph | | (CH₂)₅ | 3,5-di-Me-Ph | C/D |
| 176 | O | 4-Et-Ph | | (CH₂)₅ | 3-Me-Ph | C |
| 177 | O | 2-Me-3-MeO-Ph | i-Pr | Et | 2-MeO-Ph | C |
| 178 | O | 2-Me-3-MeO-Ph | i-Pr | Et | 3,5-di-Me-Ph | C |

TABLE 2

Compounds of Formula II Prepared.

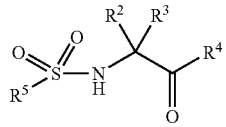

| Compound Example | R²-R³ | R⁴ | R⁵ | Method | EC$_{50}$ (μM) 27-63 | Rel Max FI 27-63 |
|---|---|---|---|---|---|---|
| 179 (RG-121198) | —(CH$_2$)$_5$— | 3,5-di-Me-Ph | 4H-benzo[1,3]dioxine-6-yl | A/C/misc | 6.53 | 0.28 |
| 180 (RG-121197) | —(CH$_2$)$_4$— | 3,5-di-Me-Ph | 4-Me-Ph | A/C/misc | 1.24, 1.80 | 0.86, 1.00 |
| 181 (RG-121502) | —(CH$_2$)$_5$— | 3,5-di-Cl-Ph | 4-Me-Ph | D | | |
| 182 (RG-121503) | —(CH$_2$)$_5$— | 3,5-di-Cl-Ph | 3-MeO-Ph | D | | |

TABLE 3

Physical Characterization of Compounds

| Compound Example | ¹H NMR(CDCl$_3$) |
|---|---|
| 1 | 1.68(s, 3H), 1.78(m, 4H), 2.02(m, 2H), 2.51(m, 2H), 3.74(s, 3H), 6.37(d, 1H), 6.72(d, 1H), 6.93(t, 1H), 7.04(s, 1H), 7.33(m, 2H), 7.42(m, 1H), 7.82(m, 2H) |
| 2 | 1.82(s, 3H), 1.84(m, 4H), 2.05(m, 2H), 2.37(s, 3H), 2.62(m, 2H), 3.78(s, 3H), 6.35(s, 1H), 6.63(d, 1H), 6.80(d, 1H), 7.04(t, 1H), 7.24(m, 2H), 7.62(d, 1H), 7.69(s, 1H) |
| 3 | 1.20(t, 3H), 1.86(m, 4H), 2.10(m, 2H), 2.67(m, 4H), 6.67(s, 1H), 7.15(d, 2H), 7.38(m, 3H), 7.49(d, 2H), 7.91(d, 2H) |
| 4 | 1.3-1.9(4H), 1.92(s, 3H), 1.99(m, 2H), 2.35(m, 2H), 3.80(s, 3H), 3.82(s, 3H), 6.29(s, 1H), 6.75(d, 1H), 6.83 (d, 1H), 7.00(m, 1H), 7.12(t, 1H), 7.22(m, 1H), 7.50(m, 3H) |
| 5 | 1.82(m, 2H), 1.84(s, 3H), 2.05(m, 2H), 2.60(m, 2H), 3.77(s, 3H), 3.82(s, 3H), 6.43(brs, 1H), 6.56(d, J=80Hz, 1H), 6.81(d, J=8.0Hz, 1H), 7.4(m, 2H), 7.26(t, J=8.0Hz), 7.42(m, 2H) |
| 6 | 1.83(s, 3H), 2.04(m, 2H), 2.33(m, 2H), 2.35(s, 3H), 3.07(m, 2H), 3.76(s, 3H), 6.56(d, J=7.9Hz, 1H), 6.78 (d, J=7.9Hz, 1H), 6.84(brs, 1H), 7.02(t, J=7.9Hz, 1H), 7.24(m, 2H), 7.52(d, J=7.3Hz, 1H), 7.63(s, 1H) |
| 7 | 1.20-1.85(6H), 1.91(s, 3H), 2.01(m, 2H), 2.36(s, 3H), 2.40(m, 2H), 3.80(s, 3H), 6.28(brs, 1H), 6.73(d, J = 7.9Hz, 1H), 6.84(d, J=7.9Hz), 7.12(t, J=7.9Hz, 1H), 7.4(m, 2H), 7.71(m, 2H) |
| 8 | 1.78(s, 3H), 1.94(s, 3H), 2.38(s, 3H), 3.64(AB quartet, 2H), 3.79(s, 3H), 6.44(brs, 1H), 6.71(d, J=7.9Hz, 1H), 6.83(d, J=7.9Hz, 1H), 7.06(t, J=7.9Hz, 1H), 7.12(m, 1H), 7.24(m, 5H), 7.80(m, 3H) |
| 9 | 1.30(m, 2H), 1.81(m, 2H), 1.88(s, 3H), 2.36(s, 3H), 3.77(s, 3H), 6.52(d, J=7.5Hz, 1H), 6.63(brs, 1H), 6.80(d, J=8.1Hz, 1H), 7.04(t, J=7.9Hz, 1H), 7.26(m, 2H), 7.52(m, 2H) |
| 10 | 1.80(m, 4H), 1.85(s, 3H), 2.06(m, 2H), 2.31(s, 6H), 2.58(m, 2H), 3.77(s, 3H), 6.46(brs, 1H), 6.52(d, J=7.6Hz, 1H), 6.79(d, J=8.1Hz, 1H), 7.04(t, J=7.9Hz, 1H), 7.10(s, 1H), 7.46(s, 2H) |
| 11 | 1.20-1.90(m, 6H), 1.96(s, 3H), 2.0(m, 2H), 2.31(s, 6H), 2.35(m, 2H), 3.80(s, 3H), 6.25(brs, 1H), 6.73(d, J=7.6Hz, 1H), 6.84(d, J=8.2Hz, 1H), 7.09(s, 1H), 7.13(t, J=7.9Hz, 1H), 7.50(s, 2H) |
| 12 | 1.80(s, 3H), 2.01(s, 3H), 2.34(s, 6H), 3.65(AB quartet, 2H), 3.80(s, 3H), 6.43(brs, 1H), 6.73(d, J=7.6Hz, 1H), 6.85(d, J=8.1Hz, 1H), 7.09(t, J=7.9Hz, 1H), 7.14(m, 3H), 7.26(m, 3H), 7.59(s, 2H) |
| 13 | 1.31(m, 2H), 1.83(m, 2H), 1.93(s, 3H), 2.32(s, 6H), 3.79(s, 3H), 6.47(s, 1H), 6.56(d, J=7.9Hz, 1H), 6.81 (d, J=7.9Hz, 1H), 7.06(d, J=7.9Hz, 1H), 7.10(s, 1H), 7.33(s, 2H) |
| 14 | 1.85(s, 3H), 2.03(m, 2H), 2.31(s, 6H), 2.34(m, 2H), 3.04(m, 2H), 3.76(s, 3H), 6.55(d, J=7.9Hz, 1H), 6.77 (d, J=7.9Hz, 1H), 6.84(brs, 1H), 7.02(t, J=7.9Hz), 7.10(s, 1H), 7.39(s, 2H) |
| 15 | 1.3-1.8(6H), 1.87(s, 3H), 2.03(m, 2H), 2.34(m, 2H), 2.36(s, 3H), 3.80(s, 3H), 6.34(brs, 1H), 6.77(d, J=7.5Hz, 1H), 6.84(d, J=8.2Hz, 1H), 7.15(m, 2H), 7.85(m, 2H) |
| 16 | 1.81(s, 3H), 1.95(s, 3H), 2.39(s, 3H), 3.66(AB quartet, 2H), 3.79(s, 3H), 6.52(brs, 1H), 6.73(d, J=7.6Hz, 1H), 6.82(d, J=8.1Hz, 1H), 7.10(m, 3H), 7.26(m, 4H), 7.94(d, J=8.2Hz, 2H) |
| 17 | 1.83(m, 4H), 1.87(s, 3H), 2.05(m, 2H), 2.29(s, 3H), 2.65(m, 2H), 3.79(s, 3H), 6.35(s, 1H), 6.58(d, J=7.6Hz, 1H), 6.81(d, J=8.3Hz, 1H), 6.97(t, J=8.9Hz, 1H), 7.08(t, J=7.9Hz, 1H), 7.70(m, 1H), 7.77(m, 1H) |
| 18 | 1.3-1.9(6H), 1.94(s, 3H), 2.05(m, 2H), 2.28(s, 3H), 2.29(m, 2H), 3.81(s, 3H), 6.28(s, 1H), 6.76(d, J=7.6Hz, 1H), 6.86(d, J=8.1Hz, 1H), 6.96(t, J=9.0Hz, 1H), 7.14(t, J=7.9Hz, 1H), 7.82(m, 2H) |
| 19 | 1.30(m, 2H), 1.81(m, 2H), 1.91(s, 3H), 2.28(s, 3H), 3.79(s, 3H), 6.55(d, J=7.6Hz), 6.62(s, 1H), 6.82(d, J=8.2Hz, 1H), 6.98(t, J=8.9Hz, 1H), 7.16(t, J=8.0Hz, 1H), 7.62(m, 2H) |
| 20 | 0.94(d, 3H), 1.08(d, 3H), 1.68(s, 3H), 2.05(s, 3H), 2.32(s, 6H), 2.50(m, 1H), 3.81(s, 3H), 6.35(s, 1H), 7.75 (d, 1H), 7.85(d, 1H), 7.12(m, 2H), 7.60(s, 2H) |
| 21 | 0.92(t, 3H), 1.81(m, 4H), 2.05(m, 2H), 2.25(q, 2H), 2.60(m, 2H), 3.76(s, 3H), 6.42(d, 1H), 6.55(s, 1H), 6.78(d, 1H), 7.00(t, 1H), 7.4(m, 3H), 7.86(d, 2H) |
| 22 | 0.88(t, 3H, J=7.4Hz), 1.81(m, 4H), 2.03(m, 2H), 2.25(q, J=7.4Hz, 2H), 2.55(m, 2H), 4.18(s, 4H), 6.43 (d, J=8.4Hz, 1H), 6.51(d, J=8.4Hz, 1H), 6.74(s, 1H), 7.40(m, 3H), 7.85(m, 2H) |
| 23 | 1.67(s, 3H), 1.81(m, 4H), 2.05(m, 2H), 2.55(m, 2H), 5.86(s, 2H), 6.32(d, J=8.2Hz, 1H), 6.41(d, J=8.2Hz, 2H), 7.40(m, 3H), 7.85(m, 2H) |

TABLE 3-continued

Physical Characterization of Compounds

| Compound Example | $^1$H NMR(CDCl$_3$) |
|---|---|
| 24 | 1.30(m, 2H), 1.82(m, 2H), 1.89(s, 3H), 2.38(s, 3H), 3.79(s, 3H), 6.53(brs, 1H), 6.59(d, 1H), 6.80(d, 1H), 7.04(t, 1H), 7.19(m, 2H), 7.66(m, 2H) |
| 25 | 1.89(s, 3H), 2.14(m, 2H), 2.36(s, 3H), 2.45(m, 2H), 3.73(m, 2H), 3.80(s, 3H), 3.92(m, 2H), 6.42(s, 1H), 6.68(d, J=7.9Hz, 1H), 6.83(d, J=7.9Hz, 1H), 7.12(t, J=7.9Hz, 1H), 7.25(m, 2H), 7.65(m, 2H) |
| 26 | 1.92(s, 3H), 2.36(s, 3H), 2.40-3.00(m, 8H), 3.81(s, 3H), 6.25(s, 1H), 6.74(d, J=8.0Hz, 1H), 6.82(d, J=8.0Hz, 1H), 7.11(t, J=8.0Hz, 1H), 7.25(m, 2H), 7.67(m, 2H) |
| 27 | 1.93(s, 3H), 2.15(m, 2H), 2.31(s, 6H), 2.41(m, 2H), 3.72(m, 2H), 3.80(s, 3H), 3.90(m, 2H), 6.54(brs, 1H), 6.68(d, J=7.5Hz, 1H), 6.84(d, J=8.2Hz, 1H), 7.12(m, 2H), 7.52(s, 2H) |
| 28 | 1.97(s, 3H), 2.31(s, 6H), 2.35-3.00(8H), 3.81(s, 3H), 6.26(brs, 1H), 6.76(d, J=7.6Hz, 1H), 6.87(m, 2H), 7.49(s, 2H) |
| 29 | 1.85(m, 4H), 1.95(s, 3H), 2.32(s, 6H), 2.40(m, 4H), 3.80(s, 3H), 3.98(s, 4H), 6.23(brs, 1H), 6.73(d, J=7.6Hz, 1H), 6.84(d, J=8.0Hz, 1H), 7.10(m, 2H), 7.50(s, 2H) |
| 30 | 1.02(d, J=6.8Hz, 3H), 1.08(d, J=6.8Hz, 3H), 1.78(s, 3H), 2.16(s, 3H), 2.52(m, 1H), 3.75(s, 3H), 3.81(s, 3H), 6.35(brs, 1H), 6.75(d, J=7.6Hz, 1H), 6.86(m, 2H), 6.98(t, J=7.5Hz, 1H), 7.11(t, J=7.9Hz, 1H), 7.38(m, 2H) |
| 31 | 0.94(d, J=6.8Hz, 3H), 1.09(d, J=6.8Hz, 3H), 1.67(s, 3H), 2.01(s, 3H), 2.37(s, 3H), 2.53(m, 1H), 6.38(br s, 1H), 6.76(d, J=7.9Hz, 1H), 6.85(d, J=7.9Hz, 1H), 7.16(t, J=7.9Hz, 1H), 7.26(m, 2H), 7.82(m, 2H) |
| 32 | 0.93(d, J=6.8Hz, 3H), 1.10(d, J=6.8Hz, 3H), 1.67(s, 3H), 2.02(s, 3H), 2.54(m, 1H0, 3.81(s, 3H), 3.83(s, 3H), 6.36(brs, 1H), 6.78(d, J=7.6Hz, 1H), 6.85(d, J=8.1Hz, 1H), 7.02(m, 1H), 7.16(m, 1H), 7.24(m, 1H), 7.59(m, 2H) |
| 33 | 0.93(d, J=6.8Hz, 3H), 1.08(d, J=6.8Hz, 3H), 1.67(s, 3H), 2.01(s, 3H), 2.37(s, 3H), 2.64(m, 1H)3.81(s, 3H), 6.38(brs, 1H), 6.79(d, J=7.6Hz, 1H), 6.86(d, J=8.2Hz, 1H), 7.17(m, 3H), 7.94(d, J=8.2Hz, 2H) |
| 34 | 0.93(d, J=6.8Hz, 3H), 1.09(d, J=6.8Hz, 3H), 1.67(s, 3H), 1.97(s, 3H), 2.54(m, 1H), 3.80(s, 3H), 6.40(br s, 1H), 6.74(d, J=7.9Hz, 1H), 6.84(d, J=7.9Hz, 1H), 7.11(t, J=7.9Hz, 1H), 7.36(m, 2H), 7.47(m, 1H), 8.00(m, 2H) |
| 35 | 1.81(m, 4H), 1.88(s, 3H), 2.35(s, 3H), 2.39(m, 4H), 3.78(s, 3H), 3.96(s, 4H), 6.46(brs, 1H), 7.69(d, 1H), 7.81(d, 1H), 7.07(t, 1H), 7.22(m, 2H), 7.70(m, 2H) |
| 36 | 0.92(t, J=7.4Hz), 2.17(s, 3H), 2.20(m, 2H), 2.40(s, 3H), 2.57(m, 2H), 3.83(s, 3H), 6.76(brs, 1H), 6.68(d, J=6.9Hz, 2H), 7.17(m, 2H), 7.29(m, 2H), 7.52(d, J=7.8Hz, 1H) |
| 37 | 0.96(t, J=7.4Hz, 6H), 2.05(m, 2H), 2.30(s, 3H), 2.61(m, 2H), 3.79(s, 3H), 3.85(s, 3H), 6.75(m, 5H), 7.18(t, J=8.0Hz, 1H), 7.26(m, 1H), 7.40(m, 1H) |
| 38 | 0.83(t, J=7.4Hz, 6H), 2.15(m, 2H), 2.21(s, 3H), 2.85(m, 2H), 3.85(s, 3H), 6.89(d, J=8.2Hz, 1H), 6.97(d, J=7.6Hz, 1H), 7.12(m, 4H), 8.02(m, 2H) |
| 39 | 1.80(s, 3H), 1.82(m, 4H), 2.14(m, 2H), 2.47(s, 3H), 2.55(m, 2H), 3.75(s, 3H), 6.30(m, 2H), 6.76(d, J=8.2Hz, 1H), 6.95(t, J=7.8Hz, 1H), 7.11(m, 1H), 7.25(m, 2H), 7.41(d, J=7.6Hz, 1H) |
| 40 | 1.83(m, 4H), 1.88(s, 3H), 2.20(m, 2H), 2.50(m, 2H), 3.76(s, 3H), 3.77(s, 3H), 6.28(brs, 1H), 6.36(d, J=7.5Hz, 1H), 6.78(d, J=8.2Hz, 1H), 6.86(d, J=8.3Hz, 1H), 7.00(m, 2H), 7.36(m, 1H), 7.58(m, 1H) |
| 41 | 1.80(m, 4H), 1.82(m, 2H), 2.03(m, 2H), 2.60(m, 2H), 3.77(s, 3H), 3.83(s, 3H), 6.58(d, J=7.9Hz, 1H), 6.64(brs, 1H), 6.79(d, J=7.9Hz, 1H), 6.82(d, J=8.8Hz, 2H), 7.04(t, J=7.9Hz, 1H), 7.88(d, J=8.8Hz, 2H) |
| 42 | 1.75(s, 3H), 1.78(m, 4H), 2.00(m, 2H), 2.55(m, 2H), 3.78(s, 3H), 6.44(d, J=7.5Hz, 1H), 6.78(d, J=8.1Hz, 1H), 6.86(brs, 1H), 7.0(m, 3H), 7.86(m, 2H) |
| 43 | 1.79(m, 4H), 1.86(s, 3H), 2.00(m, 2H), 2.55(m, 2H), 3.78(s, 3H), 5.98(s, 2H), 6.58(d, 1H), 6.76(m, 3H), 7.02(t, 1H), 7.40(s, 1H), 7.48(d, 1H) |
| 44 | 1.50(m, 2H), 1.81(m, 4H), 1.95(m, 2H), 1.97(s, 3H), 2.42(s, 3H), 2.48(m, 2H), 3.79(s, 3H), 6.02(brs, 1H), 6.61(d, J=7.5Hz, 1H), 6.82(d, J=8.1Hz, 1H), 7.09(m, 2H), 7.24(m, 2H), 7.52(d, J=7.6Hz, 1H) |
| 45 | 1.20-2.00(8H), 2.09(s, 3H), 2.45(m, 2H), 3.78(s, 3H), 3.81(s, 3H), 5.96(brs, 1H), 6.70(d, J=7.5Hz, 1H), 6.85(m, 2H), 7.00(t, J=7.5Hz, 1H), 7.11(t, J=7.8Hz, 1H), 7.34(m, 1H), 7.54(dd, J=7.5, 1.5Hz, 1H) |
| 46 | 1.30-2.1(8H), 1.90(s, 3H), 2.35(m, 2H), 3.80(s, 3H), 3.82(s, 3H), 6.42(brs, 1H), 6.82(m, 4H), 7.13(m, 1H), 7.99(d, J=8.9Hz, 2H) |
| 47 | 1.20-2.10(8H), 1.97(s, 3H), 2.35(m, 2H), 3.81(s, 3H), 5.99(s, 2H), 6.35(brs, 1H), 6.76(d, J=8.2Hz, 1H), 6.85(m, 2H), 7.17(t, 1H), 7.50(d, J=1.6Hz, 1H), 7.64(m, 1H) |
| 48 | 0.84(t, J=7.5Hz, 6H), 2.20(m, 2H), 2.25(s, 3H), 2.41(s, 3H), 2.88(m, 2H), 3.84(s, 3H), 6.89(d, J=8.0Hz, 1H), 6.99(d, J=7.5Hz, 1H), 7.19(m, 2H), 7.36(m, 2H), 7.70(m, 2H) |
| 49 | 0.85(t, J=7.4Hz, 6H), 2.20(m, 2H), 2.24(s, 3H), 2.85(m, 2H), 3.84(s, 3H), 3.85(s, 3H), 6.90(d, J=8.2Hz, 1H), 6.98(d, J=7.5Hz, 1H), 7.13(m, 3H), 7.36(t, J=8.1Hz, 1H), 7.43(m, 1H), 7.52(d, J=7.9Hz, 1H) |
| 50 | 0.83(t, J=7.4Hz, 6H), 2.17(m, 2H), 2.24(s, 3H), 2.33(s, 3H), 2.85(m, 2H), 3.85(s, 3H), 6.90(d, J=7.9Hz, 1H), 6.97(d, J=7.9Hz, 1H), 7.05(t, J=8.4Hz, 1H), 7.11(brs, 1H), 7.19(t, J=7.9Hz, 1H), 7.83(m, 2H) |
| 51 | 0.84(t, J=7.4Hz, 6H), 2.20(m, 2H), 2.27(s, 3H), 2.37(s, 6H), 2.88(m, 2H), 3.84(s, 3H), 6.89(d, J=8.2Hz, 1H), 6.99(d, J=7.6Hz, 1H), 7.18(m, 2H), 7.51(s, 2H) |
| 52 | 0.82(d, J=6.6Hz, 3H), 0.92(d, J=7.6Hz, 3H), 1.73(m, 1H), 1.89(s, 3H), 2.11(m, 1H), 2.14(s, 3H), 2.40(s, 3H), 2.63(m, 1H), 3.82(s, 3H), 6.87(m, 2H), 7.15(m, 2H), 7.30(m, 2H), 7.78(m, 2H) |
| 53 | 0.84(d, J=6.6Hz, 3H), 0.92(d, J=6.6Hz, 3H), 2.75(m, 1H), 1.89(s, 3H), 2.10(m, 1H), 2.14(s, 3H), 2.60(m, 1H), 3.82(s, 3H), 3.84(s, 3H), 6.85(m, 2H), 7.06(m, 2H), 7.15(t, J=7.9Hz, 1H), 7.32(t, J=8.0Hz, 1H), 7.50(m, 1H) 7.57(d, J=7.8Hz, 1H) |
| 54 | 0.83(t, J=6.6Hz, 3H), 0.91(d, J=6.6Hz, 3H), 1.72(m, 1H), 1.85(s, 3H), 2.06(m, 1H), 2.11(s, 3H), 2.31(s, 3H), 2.55(m, 1H), 3.82(s, 3H), 6.85(m, 2H), 7.00(t, J=8.8Hz, 1H), 7.16(m, 2H), 7.88(m, 2H) |
| 55 | 0.81(d, J=6.6Hz, 3H), 0.93(d, J=6.6Hz, 3H), 1.72(m, 2H), 1.89(s, 3H), 2.10(m, 2H), 2.18(s, 3H), 2.36(s, 6H), 2.65(m, 1H), 3.82(s, 3H), 6.88(m, 2H), 7.15(m, 3H), 7.57(s, 2H) |
| 56 | 0.90(d, J=6.8Hz, 3H), 1.09(d, J=6.8Hz, 3H), 1.63(s, 3H), 2.02(s, 3H0, 2.28(m, 3H), 2.45(m, 1H), 3.81(s, 3H), 6.42(brs, 1H), 6.76(d, J=7.9Hz, 1H), 6.87(d, J=7.9Hz, 1H), 6.96(t, J=7.9Hz, 1H), 7.15(t, J=8.0Hz, 1H), 7.90(m, 2H) |
| 57 | 0.89(t, 3H), 1.07(d, 3H), 1.97(s, 3H), 2.25(s, 3H), 3.22(m, 1H), 3.80(s, 3H), 6.7-7.7(13H) |
| 58 | 0.80(t, J=7.4Hz, 6H), 2.20(m, 2H), 2.27(s, 3H), 2.95(m, 2H), 3.85(s, 3H), 3.87(s, 3H), 6.94(m, 3H), 7.01(d, J=7.0Hz, 1H), 7.18(t, J=7.9Hz, 1H), 7.34(brs, 1H), 8.03(m, 2H) |

TABLE 3-continued

Physical Characterization of Compounds

| Compound Example | $^1$H NMR(CDCl$_3$) |
|---|---|
| 59 | 0.81(t, 6H), 2.20(m, 2H), 2.26(s, 3H), 2.90(m, 2H), 3.85(s, 3H), 6.05(s, 2H), 6.84(d, 1H), 6.91(d, 1H), 7.00 (d, 1H), 7.20(m, 2H), 7.48(s, 1H), 7.65(d, 1H) |
| 60 | 1.20-2.10(8H), 1.90(s, 3H), 2.35(m, 2H), 3.81(s, 3H), 6.32(brs, 1H), 6.77(d, J=7.6Hz, 1H), 6.87(d, J=8.2Hz, 1H), 7.04(m, 2H), 7.15(t, J=7.9Hz, 1H), 7.98(m, 2H) |
| 61 | 1.82(m, 2H), 1.91(s, 3H), 2.35(s, 3H), 2.48(m, 6H), 3.79(s, 3H), 6.7-7.9(8H) |
| 62 | 1.98(s, 3H), 2.33(s, 6H), 2.63(m, 2H), 3.00(m, 4H), 3.31(m, 2H), 3.81(s, 3H), 6.63(brs, 1H), 6.77(d, 1H), 7.90(d, 1H), 7.18(m, 2H), 7.58(s, 2H) |
| 63 | 1.06(d, J=6.9Hz, 3H), 1.09(d, J=6.9Hz, 3H), 1.73(s, 3H), 1.97(s, 3H), 2.48(s, 3H), 2.52(m, 1H), 3.79(s, 3H), 6.14(brs, 1H), 6.57(d, J=7.5Hz, 1H), 6.81(d, J=8.1Hz, 1H), 7.10(m, 2H), 7.26(m, 2H), 7.49(d, J=7.8Hz, 1H) |
| 64 | 1.20-2.60(10 H), 2.00(s, 3H), 3.82(s, 3H), 3.85(s, 3H), 3.93(s, 3H), 6.07(brs, 1H), 6.37(d, 1H), 6.71(d, 1H), 6.86(d, 1H), 7.13(t, 1H), 7.87(d, 1H) |
| 65 | 1.81(m, 4H), 1.86(s, 3H), 2.05(m, 2H), 2.28(s, 3H), 2.50(m, 2H), 3.72(s, 3H), 3.78(s, 3H), 6.48(brs, 1H), 6.56(d, J=7.9Hz, 1H), 6.80(d, J=7.9Hz, 1H), 7.05(t, J=7.9Hz, 1H), 7.58(s, 2H) |
| 66 | 1.20-2.15(8H), 1.94(s, 3H), 2.27(s, 3H), 2.30(m, 2H), 3.72(s, 3H), 3.80(s, 3H), 6.35(brs, 1H), 6.76(d, J=7.9Hz, 1H), 6.85(d, J=7.9Hz, 1H), 7.13(t, J=7.9Hz, 1H), 7.65(s, 2H) |
| 67 | 1.78(m, 4H), 1.87(s, 3H), 2.02(m, 2H), 2.53(m, 2H), 3.78(s, 3H), 3.90(s, 3H), 6.54(d, J=7.8Hz, 1H), 6.78 (d, J=7.8Hz, 1H), 6.80(brs, 1H), 7.02(t, J=7.8Hz, 1H), 7.37(m, 2H) |
| 68 | 1.25-2.10(8H), 2.00(s, 3H), 2.28(m, 2H), 3.82(s, 3H), 3.93(s, 3H), 6.37(brs, 1H), 6.80(d, J=8.0Hz, 1H), 6.87(d, J=8.0Hz, 1H), 7.16(t, J=8.0Hz, 1H), 7.45(m, 2H) |
| 69 | 1.20-2.10(8H), 1.84(s, 3H), 2.35(m, 2H), 3.79(s, 3H), 6.39(brs, 1H), 6.72(d, J=7.9Hz, 1H), 6.83(d, J=7.9Hz,) 1H), 7.11(t, J=7.9Hz, 1H), 7.34(m, 2H), 7.44(m, 1H), 7.92(m, 2H) |
| 70 | 1.63(m, 8H), 2.07(s, 3H), 3.300(m, 4H), 3.78(s, 3H), 3.81(s, 3H), 6.03(brs, 1H), 6.70(d, J=7.6Hz, 1H), 6.84(d, J=8.2Hz, 1H), 6.88(d, J=8.4Hz, 1H), 6.95(t, J=7.5Hz, 1H), 7.34(m, 1H), 7.54(m, 2H) |
| 71 | 1.62(m, 8H), 1.93(s, 3H), 2.222(m, 2H), 2.31(s, 6H), 2.45(m, 2H), 3.80(s, 3H), 6.30(brs, 1H), 6.71(d, J=7.9Hz, 1H), 6.83(d, J=7.9Hz, 1H), 7.08(s, 1H), 7.11(t, J=7.9Hz, 1H), 7.57(s, 2H) |
| 72 | 2.12(s, 3H), 2.20(s, 3H), 3.65(s, 3H), 3.83(s, 3H), 6.29(d, 1H), 6.71(t, 1H), 6.84(d, 1H), 6.89(d, 1H), 7.00-7.40 (7H), 7.80(brs, 1H) |
| 73 | 2.12(s, 3H), 2.21(s, 6H), 2.23(s, 3H), 3.82(s, 3H), 6.87(m, 1H), 7.10(m, 6H), 7.52(m, 2H), 7.90(brs, 1H) |
| 74 | 1.70(s, 6H), 2.15(s, 3H), 3.79(s, 3H), 3.80(s, 3H), 6.59(brs, 1H), 6.75-7.50(7H) |
| 75 | 1.75(s, 6H), 2.01(s, 3H), 2.33(s, 6H), 3.80(s, 3H), 6.68(brs, 1H), 6.74(d, J=7.5Hz, 1H), 6.83(d, J=8.1Hz, 1H), 7.10(m, 2H), 7.58(s, 2H) |
| 76 | 1.73(s, 6H), 1.91(s, 3H), 3.78(s, 3H), 6.78(m, 3H), 7.08(t, J=8.0Hz, 1H), 7.38(m, 2H), 7.46(m, 1H), 7.96 (m, 2H) |
| 77 | 0.82(t, J=7.4Hz, 6H), 2.20(m, 1H), 2.26(s, 3H), 2.41(s, 3H), 2.92(m, 1H), 3.84(s, 3H), 6.89(d, J=8.2Hz, 1H), 7.00(d, J=7.4Hz, 1H), 7.24(m, 3H), 7.87(d, J=8.3Hz, 2H) |
| 78 | 0.84(t, J=7.4Hz, 6H), 2.16(m, 1H), 2.22(s, 3H), 2.86(m, 1H), 6.88(d, J=8.2Hz, 1H), 6.97(d, J=7.5Hz, 1H), 7.18(m, 2H), 7.24(m, 2H), 7.35(m, 1H), 7.92(d, J=7.4Hz, 2H) |
| 79 | 1.77(s, 3H), 1.83(m, 4H), 2.03(m, 2H), 2.37(s, 3H), 2.59(m, 2H), 3.77(s, 3H), 6.52(d, 1H), 6.60(brs, 1H), 6.78(d, 1H), 7.01(t, 1H), 7.15(d, 2H), 7.78(s, 2H) |
| 80 | 1.01(t, 3H), 1.30-2.20(10H), 2.32(s, 6H), 2.44(m, 2H), 4.25(s, 4H), 6.20(brs, 1H), 6.69(m, 2H), 7.10(s, 1H), 7.51(s, 2H) |
| 81 | 1.25-2.40(10H), 1.95(s, 3H), 2.31(s, 6H), 5.96(s, 2H), 6.22(s, 1H), 6.61(d, 1H), 6.82(d, 1H), 7.07(s, 1H), 7.51(s, 2H) |
| 82 | 1.25-2.40(10H), 2.27(s, 6H), 4.27(s, 4H), 6.45(brs, 1H), 6.85(d, 1H), 7.02(s, 1H), 7.21(m, 2H), 7.50(s, 2H) |
| 83 | 1.25-2.40(10H), 2.27(s, 6H), 4.87(s, 2H), 5.25(s, 2H), 6.48(brs, 1H), 6.85(d, 1H), 7.02(s, 1H), 7.35(s, 1H), 7.49(m, 3H) |
| 84 | 0.95(t, 3H), 1.82(m, 4H), 2.05(m, 2H), 2.34(s, 6H), 2.59(m, 2H), 4.22(s, 4H), 6.19(brs, 1H), 6.51(d, 1H), 6.64(d, 1H), 7.09(s, 1H), 7.47(s, 2H) |
| 85 | 1.83(m, 4H), 1.90(s, 3H), 2.03(m, 2H), 2.32(s, 6H), 2.60(m, 2H), 5.93(s, 2H), 6.25(brs, 1H), 6.55(d, 1H), 6.65(d, 1H), 7.08(s, 1H), 7.46(s, 2H) |
| 86 | 1.83(m, 4H), 2.05(m, 2H), 2.28(s, 6H), 2.60(m, 2H), 4.24(s, 4H), 6.55(brs, 1H), 6.78(d, 1H), 7.05(m, 3H), 7.50(s, 2H) |
| 87 | 1.85(m, 4H), 2.08(m, 2H), 2.28(s, 6H), 2.61(m, 2H), 4.82(s, 2H), 5.24(s, 2H), 6.55(brs, 1H), 6.81(d, 1H), 7.03(s, 1H), 7.29(s, 1H), 7.33(m, 1H), 7.49(s, 2H) |
| 88 | 1.20-2.20(10H), 2.31(s, 6H), 4.26(m, 4H), 5.19(s, 1H), 6.84(d, 1H), 7.08(s, 1H), 7.25(m, 2H), 7.47(s, 2H) |
| 89 | 1.79(m, 4H), 2.01(m, 2H), 2.29(s, 6H), 2.32(m, 2H), 2.38(s, 3H), 5.19(s, 1H), 7.08(s, 1H), 7.15(d, J=8.2 Hz, 2H), 7.37(s, 2H), 7.52(d, J=8.2Hz, 2H) |
| 110 | 7.50(s, 2H), 7.11(m, 2H), 6.84(d, 1H), 6.68(d, 1H), 6.48(s, 1H), 3.95(m, 2H), 3.79(s, 3H), 3.18(m, 2H), 2.31(s, 6H), 2.23(m, 4H), 1.93(s, 3H), 1.47(s, 9H) |
| 147 | 7.55(s, 2H), 7.12(m, 2H), 6.87(d, 1H), 6.77(d, 1H), 6.65(br, 1H), 3.8(s, 3H), 3.1(br, 2H), 2.95(br, 2H), 2.3 (s, 6H), 2.25(brs, 4H), 1.94(s, 3H) |
| 148 | 7.7(s, 2H), 7.35(s, 1H), 7.2(m, 2H), 6.83(m, 2H), 3.78(s, 3H), 3.40(d, 1H), 3.08(d, 1H), 2.97(d, 1H), 2.7 (m, 2H), 2.4(m, 1H), 2.31(s, 6H), 2.25(m, 1H), 1.96(s, 3H), 1.75(m, 1H), 1.65(m, 1H) |
| 149 | 7.6(s, 2H), 7.15(m, 2H), 6.87(d, 2H), 6.7(d, 1H), 4.17(dt, 1H), 3.8(s, 3H), 3.78(m, 1H), 3.45(t, 1H), 3.25(t, 1H), 2.5(m, 1H), 2.35(m, 1H), 2.32(s, 6H), 2.2(m, 1H), 2.17(m, 1H), 2.05(s, 3H), 1.92(s, 3H). |
| 150 | 7.55(s, 2H), 7.15(s, 1H), 7.1(t, 1H), 6.87(d, 1H), 6.83(t, 1H), 6.68(d, 1H), 4.35(m, 1H), 3.90(m, 1H), 3.80 (s, 3H), 3.68(m, 1H), 3.45(m, 2H), 2.55(m, 1H), 2.33(s, 6H), 2.15-2.35(m, 3H), 1.92(s, 3H), 1.35(t, 3H) |
| 151 | 7.55(s, 2H), 7.15(s, 1H), 7.13(d, 1H), 6.85(d, 1H), 6.70(d, 1H), 6.6(s, 1H), 3.82(s, 3H), 3.45(m, 2H), 3.30 (m, 2H), 2.77(s, 3H), 2.57(m, 2H), 2.33(s, 6H), 2.25(m, 2H), 1.97(s, 3H) |
| 152 | 7.51(s, 2H), 7.15(t, 1H), 7.1(s, 1H), 6.87(d, 1H), 6.77(d, 1H), 6.27(s, 1H), 3.82(s, 3H), 3.75(s, 3H), 3.30(s, 2H), 2.9(m, 2H), 2.65(m, 2H), 2.45(m, 2H), 2.3(m, 2H), 2.32(s, 6H), 1.97(s, 3H) |

TABLE 3-continued

Physical Characterization of Compounds

| Compound Example | $^1$H NMR(CDCl$_3$) |
|---|---|
| 153 | 7.62 + 7.52(2s, 1H), 7.13(s, 1H), 7.09(m, 1H), 6.93 + 6.62(2s, 1H), 6.87 + 6.82(2d, 1H), 6.75 + 6.57(2d, 1H), 5.32 + 4.65(2d, 1H), 4.55 + 3.87(2d, 1H), 3.78(s, 3H), 3.17 + 2.83(2m, 1H), 2.7(m, 1H), 2.47(m, 1H), 2.32 + 2.30(2s, 6H), 2.17 + 1.92(2s, 3H), 2.0 + 1.77(2s, 3H), 2.05(m, 1H), 1.85(m, 1H), 1.77(m, 1H) |
| 154 | 7.57 + 7.55(2s, 2H), 7.14 + 7.1(2t, 1H), 7.13(brs, 1H), 7.06 + 6.56(2s, 1H), 6.92 + 6.83(2d, 1H), 6.87 + 6.7 (2d, 1H), 5.17 + 4.67(2d, 1H), 4.37(q, 2H), 4.32(m, 1H), 4.18(m, 1H), 3.8(s, 3H), 3.63(d, 1H), 3.17(m, 1H), 2.77(m, 1H), 2.66(m, 1H), 2.32(s, 6H), 2.25(m, 1H), 1.87 + 1.77(2s, 3H), 1.85(m, 1H), 1.17(t, 3H) |
| 155 | 7.65(s, 2H), 7.15(t, 1H), 7.13(s, 1H), 6.85(m, 2H), 6.77(s, 1H), 4.40(d, 1H), 3.9(d, 1H), 3.8(s, 3H), 3.1(d, 1H), 2.83(s, 3H), 2.75(m, 1H), 2.63(m, 1H), 2.33(s, 6H), 2.15(m, 1H), 1.95(s, 3H), 1.9(m, 2H) |
| 156 | 7.73(s, 2H), 7.45(s, 1H), 7.17(t, 1H), 7.10(s, 1H), 6.95(d, 1H), 6.85(d, 1H), 3.8(s, 3H), 3.7(s, 3H), 3.5(d, 1H), 3.33(d, 1H), 3.25(d, 1H), 2.85(d, 1H), 2.5,(d, 1H), 2.4(m, 2H), 2.34(s, 6H), 2.12(m, 1H), 2.05(s, 3H), 1.85(m, 1H), 1.75(m 1H) |
| 157 | 7.55(s, 2H), 7.13(s, 1H), 7.12(s, 1H), 7.07(t, 1H), 6.8(d, 1H), 6.65(d, 1H), 4.85(t, 1H), 3.77(s, 3H), 3.7(dt, 2H), 3.22(dt, 2H), 3.12(m, 2H), 2.3(s, 6H), 2.25(m, 4H), 1.87(s, 3H), 1.05(t, 3H) |
| 158 | 7.53(s, 2H), 7.13(s, 1H), 7.1(m, 1H), 6.85(d, 1H), 6.67(d, 1H), 6.63(s, 1H), 4.87(m, 1H), 3.93(dt, 2H), 3.78 (s, 3H), 3.2(br, 2H), 2.31(s, 6H), 2.2(m, 4H), 1.91(s, 3H), 1.25(d, 6H) |
| 159 | 7.5(s, 2H), 7.13(s, 1H), 7.13(t, 1H), 6.84(d, 1H), 6.72(d, 1H), 6.52(d, 1H), 3.8(s, 3H), 3.53(s, 2H), 2.8(m, 2H), 2.67(m, 2H), 2.4(m, 2H), 2.32(s, 6H), 1.95(s, 3H) |
| 160 | 7.55(s, 2H), 7.27(s, 1H), 7.12(s, 1H), 7.1(t, 1H), 6.84(d, 1H), 6.67(d, 1H), 4.8(t, 1H), 4.75(d, 1H), 4.0(d, 1H), 3.88(s, 3H), 3.25(m, 2H), 3.15(m, 1H), 2.93(dt, 1H), 2.6(d, 1H), 2.31(s, 6H), 2.26(dd, 1H), 1.82(s, 3H), 1.7(m, 1h), 1.05(t, 3H) |
| 161 | 7.65(s, 2H), 7.16(t, 1H), 7.12(s, 1H), 7.1(s, 1H), 6.85(d, 2H), 3.81(s, 3H), 3.22(d, 1H), 2.85(d, 1H), 2.45(d, 1H), 2.32(s, 6H), 2.27(s, 3H), 2.17(d, 1H), 2.05(dt, 1H), 2.02(s, 3H), 1.95(t, 1H), 1.8(m, 1H), 1.75(m, 1H) |
| 163 | 7.82(s, 2H), 7.6(d, 2H), 7.4(s, 1H), 7.3(d, 2H), 6.65(s, 1H), 2.7(q, 2H), 2.3(d, 2H), 2.0(dt, 2H), 1.85(d, 2H), 1.75(d, 1H), 1.5(q, 2H), 1.4(m, 1H), 1.24(t, 3H) |
| 164 | 7.37(m, 1H), 7.15(t, 1H), 7.05(m, 1H), 6.88(d, 1H), 6.82(m, 2H), 5.99(s, 1H), 3.82(s, 3H), 3.77(s, 3H), 2.40(d, 2H), 2.14(s, 3H), 1.86(t, 2H), 1.73(d, 3H), 1.5(q, 2H), 1.3(m, 1H) |
| 165 | 7.3(s, 1H), 7.15(m, 2H), 6.87(d, 1H), 6.8(m, 2H), 5.98(s, 1H), 3.81(s, 3H), 3.74(s, 3H), 2.44(d, 2H), 2.28 (s, 3H), 2.10(s, 3H), 1.89(m, 2H), 1.71(d, 3H), 1.47(q, 2H), 1.35(m, 1H) |
| 166 | 7.15(m, 2H), 6.9(m, 1H), 6.87(m, 1H), 6.82(m, 1H), 6.8(d, 1H), 5.99(s, 1H), 3.81(s, 3H), 3.77(s, 3H), 3.74 (s, 3H), 2.44(d, 2H), 2.12(s, 3H), 1.88(t, 2H), 1.75(m, 3H), 1.47(m, 1H) |
| 167 | 8.35(s, 1H), 7.82(s, 1H), 7.16(m, 1H), 7.11(t, 1H), 6.82(d, 1H), 6.22(d, 1H), 6.4(s, 1H), 3.79(s, 3H), 2.70 (d, 2H), 2.38(s, 3H), 2.05(t, 2H), 1.85(s, 3H), 1.8(m, 2H), 1.6(m, 3H), 1.4(m, 1H) |
| 168 | 7.8(d, 1H), 7.72(m, 1H), 7.2(d, 1H), 7.1(t, 1H), 6.85(d, 1H), 6.65(d, 1H), 6.4(s, 1H), 3.79(s, 3H), 2.7(d, 2H), 2.48(s, 3H), 2.1(t, 2H), 1.88(s, 3H), 1.8(m, 3H), 1.65(m, 2H), 1.4(m, 1H) |
| 169 | 7.62(d, 2H), 7.4(m, 1H), 7.25(d, 2H), 7.0(m, 1H), 6.8(d, 1H), 6.4(s, 1H), 3.77(s, 3H), 2.68(m, 2H), 2.34(d, 2H), 1.87(t, 2H), 1.75(d, 3H), 1.5(q, 2H), 1.3(m, 1H), 1.24(t, 3H) |
| 170 | 7.6(d, 2H), 7.32(s, 1H), 7.22(d, 2H), 7.1(d, 1H), 6.72(d, 1H), 6.37(s, 1H), 3.76(s, 3H), 2.7(q, 2H), 2.4(d, 2H), 2.26(s, 3H), 1.9(t, 2H), 1.7(d, 3H), 1.5(q, 2H), 1.3(m, 1H), 1.25(t, 3H) |
| 171 | 7.6(d, 2H), 7.22(d, 2H), 7.15(s, 1H), 6.85(m, 1H), 6.8(m, 1H), 6.37(s, 1H), 3.75(s, 3H), 3.73(s, 3H), 2.7(q, 2H), 2.42(d, 2H), 1.9(t, 2H), 1.72(br, 3H), 1.5(q, 2H), 1.3(m, 1H), 1.27(t, 3H) |
| 172 | 8.25(s, 1H), 7.8(s, 1H), 7.55(d, 2H), 7.2(d, 2H), 7.1(d, 1H), 6.8(s, 1H), 2.7(d, 2H), 2.63(m, 2H), 2.35(s, 3H), 2.05(t, 2H), 1.75(m, 3H), 1.65(m, 2H), 1.4(m, 1H), 1.21(t, 3H) |
| 173 | 7.8(d, 1H), 7.65(t, 1H), 7.57(d, 2H), 7.2(d, 2H), 7.15(d, 1H), 6.8(s, 1H), 2.7(m, 2H), 2.65(m, 2H), 2.41(s, 3H), 2.1(m, 2H), 1.8(m, 3H), 1.65(m, 2H), 1.4(m, 1H), 1.25(t, 3H) |
| 174 | 7.6(d, 2H), 7.55(d, 1H), 7.3(m, 1H), 7.22(d, 2H), 6.97(t, 1H), 6.85(d, 1H), 6.4(s, 1H), 3.78(s, 3H), 2.7(q, 2H), 2.4(d, 2H), 1.9(t, 2H), 1.7(m, 3H), 1.5(q, 2H), 1.3(m, 1H), 1.2(t, 3H) |
| 175 | 7.6(d, 2H), 7.55(s, 2H) 7.2(d, 2H), 7.03(s, 1H), 6.7(s, 1H), 2.7(q, 2H), 2.35(d, 2H), 2.25(s, 6H), 1.99(t, 2H), 1.8(m, 2H), 1.7(m, 1H), 1.52(q, 2H), 1.36(m, 1H), 1.22(t, 3H) |
| 176 | 7.75(m, 2H), 7.6(d, 2H), 7.2(m, 4H), 6.65(s, 1H), 2.67(q, 2H), 2.37(d, 2H), 2.31(s, 3H), 2.02(dt, 2H), 1.8 (d, 2H), 1.72(m, 1H), 1.55(q, 2H), 1.4(q, 1H), 1.22(t, 3H) |
| 177 | 7.4(m, 1H), 7.3(m, 1H), 7.17(m, 1H), 7.15(s, 1H), 6.98(m, 3H), 6.88(d, 1H), 3.84(s, 3H), 3.73(s, 3H), 2.95 (m, 1H), 2.64(m, 1H), 2.33(m, 1H), 2.29(s, 3H), 1.17(d, 3H), 1.01(t, 3H), 0.95(d, 3H) |
| 178 | 7.5(s, 2H), 7.21(m, 2H), 7.12(s, 1H), 7.07(d, 1H), 6.9(d, 1H), 3.38(s, 3H), 3.29(m, 1H), 2.67(m, 1H), 2.36 (s, 6H), 2.30(s, 3H), 2.26(m, 1H), 1.22(d, 3H), 0.88(m, 6H) |
| 181 | 7.8(s, 2H), 7.6(d, 2H), 7.4(s, 1H), 7.2(d, 2H), 5.75(s, 1H), 2.35(s, 3H), 1.9(m, 2H), 1.8(m, 2H), 1.4(m, 3H), 1.3(m, 2H), 1.2(m, 1H) |
| 182 | 7.8(s, 2H), 7.37(s, 1H), 7.3(m, 2H), 7.2(s, 1H), 6.98(d, 1H, 5.75(s, 1H), 3.72(s, 3H), 1.95(m, 2H), 1.85(m, 2H), 1.4(m, 3H), 1.25(m, 2H), 1.2(m, 1H) |

Example 2

Biological Testing of Compounds

The ligands of the present invention are useful in various applications including gene therapy, expression of proteins of interest in host cells, production of transgenic organisms, and cell-based assays.

Z3 Assay

Stable Cell Lines

Dr. F. Gage provided a population of stably transformed cells containing CVBE and 6×EcRE as described in Suhr, S. T., Gil, E. B., Senut M. C., Gage, F. H. (1998) Proc. Natl. Acad. Sci. USA 95, 7999-804. Human 293 kidney cells, also referred to as HEK-293 cells, were sequentially infected with retroviral vectors encoding first the switch construct CVBE, and subsequently the reporter consturt 6×EcRE Lac Z. The switch construct contained the coding sequence for amino acids 26-546 from Bombyx mori EcR (BE) (Iatrou) inserted in frame and downstream of the VP16 transactivation domain (VBE). A synthetic ATG start codon was placed under the control of cytomegalovirus (CVBE) immediate early promoter and flanked by long terminal repeats (LTR). The reporter construct contained six copies of the ecdysone response element (ECRE) binding site placed upstream of LacZ and flanked on both sides with LTR sequences (6×EcRE).

Dilution cloning was used to isolate individual clones. Clones were selected using 450 ug/mL G418 and 100 ng/mL puromycin. Individual clones were evaluated based on their response in the presence and absence of test ligands. Clone Z3 was selected for screening and SAR purposes.

Mammalian Cell Lines

Human 293 kidney cells stably transformed with CVBE and 6×EcRE lack were maintained in Minimum Essential Medium (Mediates, 10-010-CV) containing 10% FBS (Life Technologies, 26140-087), 450 gum G418 (Mediates, 30-234-CR), and 100 gnome promising (Sigma, P-7255), at 37° C. in an atmosphere containing 5% $CO_2$ and were subculture when they reached 75% confluence.

Treatment with Ligand

Z3 cells were seeded into 96-well tissue culture plates at a concentration of $2.5 \times 10^3$ cells per well and incubated at 37° C. in 5% $CO_2$ for twenty-four hours. Stock solutions of ligands were prepared in DMSO. Ligand stock solutions were diluted 100 fold in media and 50 µL of this diluted ligand solution (33 µM) was added to cells. The final concentration of DMSO was maintained at 0.03% in both controls and treatments.

Reporter Gene Assays

Reporter gene expression was evaluated 48 hours after treatment of cells, β-galactosidase activity was measured using Gal Screen™ bioluminescent reporter gene assay system from Tropix (GSY1000). Fold induction activities were calculated by dividing relative light units ("RLU") in ligand treated cells with RLU in DMSO treated cells. Luminescence was detected at room temperature using a Dynex MLX microtiter plate luminometer.

A schematic of switch construct CVBE, and the reporter construct 6×EcRE Lac Z is shown in FIG. 1. Flanking both constructs are long terminal repeats, G418 and puromycin are selectable markers, CMV is the cytomegalovirus promoter, VBE is coding sequence for amino acids 26-546 from Bombyx mori EcR inserted downstream of the VP16 transactivation domain, 6×EcRE is six copies of the ecdysone response element, lacZ encodes for the reporter enzyme β-galactosidase. Suhr, S. T., Gil, E. B., Senut M. C., Gage, F. H. (1998) Proc. Natl. Acad. Sci. USA 95, 7999-804. Swevers, L., Drevet, J. R., Lunke, M. D., Iatrou, K. (1995) Insect Biochem. Mol. Biol. 25, 857-866.

27-63 Assay

Gene Expression Cassette

GAL4 DBD (1-147)-CfEcR(DEF)/VP16AD-βRXREF-LmUSPEF: The wild-type D, E, and F domains from spruce budworm Choristoneura fumiferana EcR ("CfEcR-DEF"; SEQ ID NO: 1) were fused to a GAL4 DNA binding domain ("Gal4DBD1-147"; nucleotides 31 to 471 of SEQ ID NO: 2) and placed under the control of a phosphoglycerate kinase promoter ("PGK"; SEQ ID NO: 3). Helices 1 through 8 of the EF domains from Homo sapiens RXRβ and helices 9 through 12 of the EF domains of Locusta migratoria Ultraspiracle Protein ("HsRXRβ-EF-LmUSP-EF"; SEQ ID NO: 4) were fused to the transactivation domain from VP16 ("VP16AD"; SEQ ID NO: 5) and placed under the control of an elongation factor-1α promoter ("EF-1α"; SEQ ID NO: 6). Five consensus GAL4 response element binding sites ("5XGALARE"; comprising 5 copies of a GAL4RE comprising SEQ ID NO: 7) were fused to a synthetic TATA minimal promoter (SEQ ID NO: 8) and placed upstream of the luciferase reporter gene (SEQ ID NO: 9).

Stable Cell Line

CHO cells were transiently transfected with transcription cassettes for GALA DBD (1-147) CfEcR(DEF) and for VP16AD βRXREF-LmUSPEF controlled by ubiquitously active cellular promoters (PGK and EF-1α, respectively) on a single plasmid. Stably transfected cells were selected by Zeocin resistance. Individually isolated CHO cell clones were transiently transfected with a GAL4 RE-luciferase reporter (pFR Luc). 27-63 clone was selected using Hygromycin.

Treatment with Ligand

Cells were trypsinized and diluted to a concentration of $2.5 \times 10^4$ cells mL. 100 µL of cell suspension was placed in each well of a 96 well plate and incubated at 37° C. under 5% $CO_2$ for 24 h. Ligand stock solutions were prepared in DMSO and diluted 300 fold for all treatments. Dose response testing consisted of 8 concentrations ranging from 33 µM to 0.01 µM.

Reporter Gene Assay

Luciferase reporter gene expression was measured 48 h after cell treatment using Bright-Glom ™ Luciferase Assay System from Promega (E2650). Luminescence was detected at room temperature using a Dynex MLX microtiter plate luminometer.

13B3 Assay

Gene Expression Cassette

GAL4 DBD-CfEcR(DEF)/VP16AD-MmRXRE: The wild-type D, E, and F domains from spruce budworm Choristoneura fumiferana EcR ("CfEcR-DEF"; SEQ ID NO: 1) were fused to a GAL4 DNA binding domain ("Gal4DBD1-147"; nucleotides 31 to 471 of SEQ ID NO: 2) and placed under the control of the SV40e promoter of pM vector (PT3119-5, Clontech, Palo Alto, Calif.). The D and E domains from Mus Musculus RXR ("MmRXR-DF"; SEQ ID NO: 10) were fused to the transactivation domain from VP16 ("VP16AD"; SEQ ID NO: 5) and placed under the control of the SV40e promoter of the pVP16 vector (PT3127-5, Clontech, Palo Alto, Calif.).

Stable Cell Line

CHO cells were transiently transfected with transcription cassettes for GAL4 DBD-CfEcR(DEF) and for VP16AD-MmRXRE controlled by SV40e promoters. Stably transfected cells were selected using Hygromycin. Individually isolated CHO cell clones were transiently transfected with a GAL4 RE-luciferase reporter (pFR-Luc, Stratagene, La Jolla, Calif.). The 13B3 clone was selected using Zeocin.

Treatment with Ligand

Cells were trypsinized and diluted to a concentration of $2.5 \times 10^4$ cells mL. 100 μL of cell suspension was placed in each well of a 96 well plate and incubated at 37° C. under 5% $CO_2$ for 24 h. Ligand stock solutions were prepared in DMSO and diluted 300 fold for all treatments. Dose response testing consisted of 8 concentrations ranging from 33 μM to 0.01 μM.

Reporter Gene Assay

Luciferase reporter gene expression was measured 48 h after cell treatment using Bright-Glo™ Luciferase Assay System from Promega (E2650). Luminescence was detected at room temperature using a Dynex MLX microtiter plate luminometer.

AA3T3V1 Assay

Gene Expression Cassette

Gal4DBD/AaEcR (DEF): The wildtype D, E, and F domains from mosquito *Aedes aegypti* EcR ("AaEcR-DEF"; SEQ ID NO: 11) were fused to a GAL4 DNA binding domain (nucleotides 31 to 471 of SEQ ID NO: 2) and placed under the control of a long CMV promoter (SEQ ID NO: 12). The E domain from mouse (*Mus musculus*) RXR ("βRXR-E"; SEQ ID NO: 13) was fused to the carboxyl terminus of the activation domain from VP16 (SEQ ID NO: 5) and placed under the control of the SV40 promoter (SEQ ID NO: 14).

Cell Line and Treatment with Ligand

3T3 cells were trypsinized and plated at $2.5 \times 10^3$ cells/well on a 96-well plate. After incubation for 24 h at 37° C. under 5% $CO_2$, cells were transfected with the Gal4DBD/AaEcR (DEF) gene expression cassette and the reporter plasmid, pFRLuc, containing a 5×GAL4 response element and the firefly luciferase gene in serum free media using Superfect (Qiagen). After transfection for 4 h at 37° C., the cells were treated with ligand in serum media. Ligand stock solutions were prepared in DMSO and diluted 300-fold for all treatments. Single dose testing was performed at 33 μM. Dose response testing consisted of 8 concentrations ranging from 33 μM to 0.01 μM.

Reporter Gene Assay

Luciferase reporter gene expression was measured 48 h after cell treatment using Bright-Glo™ Luciferase Assay System from Promega (E2650). Luminescence was detected at room temperature using a Dynex MLX microtiter plate luminometer.

The results of the assays are shown in Tables 4 and 5. Fold inductions were calculated from single dose testing by dividing relative light units (RLU) in ligand treated cells by RLU in DMSO treated cells. $EC_{50}$s were calculated from dose response data using a three-parameter logistic model. Relative Max FI was determined as the maximum fold induction of the tested ligand (an embodiment of the invention) observed at any concentration relative to the maximum fold induction of GS™-E ligand (3,5-Dimethyl-benzoic acid N-tert-butyl-N'-(2-ethyl-3-methoxy-benzoyl)-hydrazide) observed at any concentration.

TABLE 4

Biological Assay Results: Fold Induction

| Compound Example | 13B3 Assay (33 μM) | 27-63 Assay (33 μM) | AA_3T3 Assay (33 μM) | Z3 Assay (33 μM) |
|---|---|---|---|---|
| 1 | 3 | | | 71 |
| 2 | 2622 | | | 786 |
| 3 | 13 | | | 133 |
| 4 | 45 | | | 233 |
| 5 | 1 | | | 127 |
| 6 | 1 | | | 82 |
| 7 | 3099 | | | 811 |
| 8 | 2 | | | 15 |
| 9 | 0 | | | 12 |
| 10 | 32706 | | | 464 |
| 11 | 94686 | | | 722 |
| 12 | 72 | | | 76 |
| 13 | 3 | | | 293 |
| 14 | 1024 | | | 945 |
| 15 | 371 | | | 921 |
| 16 | 0 | | | 10 |
| 17 | 1191 | | | 393 |
| 18 | 50157 | | | 657 |
| 19 | 0 | | | 6 |
| 20 | 107253 | | | 573 |
| 21 | 2 | | | 305 |
| 22 | 4 | | | 602 |
| 23 | 2 | | | 32 |
| 24 | 87 | | | 11 |
| 25 | 117 | | | 19 |
| 26 | 107178 | | | 751 |
| 27 | 31557 | 2742 | | 562 |
| 28 | 3182 | | | 1217 |
| 29 | 5 | | | 116 |
| 30 | 133 | | | 485 |
| 31 | 1005 | | | 312 |
| 32 | 96 | | | 33 |
| 33 | 78 | | | 31 |
| 34 | 6 | | | 66 |
| 35 | 2 | | | 9 |
| 36 | 0 | | | 4 |
| 37 | 885 | | | 327 |
| 38 | 18 | | | 51 |
| 39 | 24 | | | 30 |
| 40 | 2173 | | | 951 |
| 41 | 2 | | | 4 |
| 42 | 4 | | | 153 |
| 43 | 2 | | | 3 |
| 44 | 36 | | | 94 |
| 45 | 92919 | | | 665 |
| 46 | 102 | 5 | | 15 |
| 47 | 3 | | | 21 |
| 48 | 12 | | | 356 |
| 49 | 0 | | | 182 |
| 50 | 1 | | | 178 |
| 51 | 1381 | | | 817 |
| 52 | 114 | | | 239 |
| 53 | 0 | | | 112 |
| 54 | 0 | | | 41 |
| 55 | 24711 | | | 309 |
| 56 | 2 | | | 265 |
| 57 | 0 | | | 8 |
| 58 | 4 | | | 4 |
| 59 | 0 | | | 2 |
| 60 | 578 | | | 817 |
| 61 | 0 | | | 102 |
| 62 | 3 | 224 | | 347 |
| 63 | 14 | | | 453 |
| 64 | 599 | | | 1157 |
| 65 | 19 | | | 151 |
| 66 | 357 | | | 341 |
| 67 | 555 | | | 666 |
| 68 | 819 | | | 1009 |
| 69 | 164 | | | 1028 |
| 70 | | | 1878 | 831 |
| 71 | | | 1277 | 952 |
| 72 | | 1 | 3 | 1 |

TABLE 4-continued

Biological Assay Results: Fold Induction

| Compound Example | 13B3 Assay (33 μM) | 27-63 Assay (33 μM) | AA_3T3 Assay (33 μM) | Z3 Assay (33 μM) |
|---|---|---|---|---|
| 73 |  |  | 1 | 4 |
| 74 |  | 9 | 4 | 18 |
| 75 |  |  | 161 | 312 |
| 76 |  |  | 0 | 1 |
| 77 |  |  | 1 |  |
| 78 |  |  | 14 |  |
| 79 |  |  | 12 |  |
| 89 |  |  | 78 |  |
| 92 | 0 |  |  | 1 |
| 93 | 0 |  |  | 1 |
| 94 | 1 |  |  | 1 |
| 95 | 1 |  |  | 4 |
| 96 | 0 |  |  | 1 |
| 97 | 0 |  |  | 1 |
| 98 | 0 |  |  | 1 |
| 99 | 0 |  |  | 1 |
| 100 | 0 |  |  | 2 |
| 101 | 2 |  |  | 2 |
| 102 | 1 |  |  | 1 |
| 103 | 0 |  |  | 0 |
| 104 | 0 |  |  | 1 |
| 105 | 3 |  |  | 1 |
| 106 | 3 |  |  | 1 |
| 107 | 2 |  |  | 1 |
| 108 | 1 |  |  | 2 |
| 109 | 0 |  |  | 3 |
| 110 | 2 |  |  | 1 |
| 111 | 0 |  |  | 1 |
| 112 | 2 |  |  | 1 |
| 113 | 1 |  |  | 4 |
| 114 | 2 |  |  | 3 |
| 115 | 1 |  |  | 15 |
| 116 | 4 |  |  | 1 |
| 117 | 12 | 1 |  | 1 |
| 118 | 0 |  |  | 1 |
| 119 | 0 |  |  | 1 |
| 120 | 367 |  |  | 791 |
| 122 |  |  | 0 |  |
| 123 |  |  | 0 |  |
| 124 |  |  | 2 |  |
| 125 |  |  | 1 |  |
| 130 |  |  | 0 |  |
| 131 |  |  | 0 |  |
| 132 |  |  | 1 |  |
| 133 |  |  | 0 |  |
| 134 |  |  | 0 |  |
| 135 |  |  | 0 |  |
| 137 |  |  | 115 |  |
| 138 |  |  | 2134 |  |
| 139 |  |  | 2 |  |
| 140 |  |  | 0 |  |
| 141 |  |  | 1 |  |
| 142 |  |  | 0 |  |
| 143 |  |  | 1929 |  |
| 144 |  |  | 2339 |  |
| 145 |  |  | 0 |  |
| 146 | 1 |  | 0 | 1 |
| 147 | 1 |  | 0 | 1 |
| 148 | 2 |  | 0 | 7 |
| 149 | 1 |  | 2 | 2 |
| 150 | 1 |  | 0 | 3 |
| 151 | 1 |  | 0 | 3 |
| 152 | 3 |  | 0 | 6 |
| 153 | 1 |  | 0 | 3 |
| 154 | 2 |  | 2 | 7 |
| 155 | 2 |  | 0 | 4 |
| 156 | 3 |  | 0 | 78 |
| 157 | 1 |  | 1 | 2 |
| 158 | 0 |  | 1 | 4 |
| 159 | 1 |  | 0 | 2 |
| 160 | 1 |  | 0 | 1 |
| 161 | 1 |  | 0 | 27 |

TABLE 5

Biological Assay Results: Average $EC_{50}$/Rel Max FI

| Compound Example | 13B3 EC50 (μM) | Rel Max FI | 27-63 LC50 (μM) | Rel Max FI | AA_3T3 LC50 (μM) | Rel Max FI | Z3 LC50 (μM) | Rel Max FI |
|---|---|---|---|---|---|---|---|---|
| 1 | >33 | 0.00 |  |  |  |  | 2.67 | 0.14 |
| 2 | >33 | 0.24 |  |  |  |  | 3.38 | 0.46 |
| 3 | >33 | 0.00 |  |  |  |  | 12.91 | 0.20 |
| 4 | 3.46 | 0.64 | 4.28 | 1.06 |  |  | 1.19 | 0.54 |
| 5 | >33 | 0.02 |  |  |  |  | 8.82 | 0.12 |
| 6 | >33 | 0.00 |  |  |  |  | 10.67 | 0.05 |
| 7 | 6.73 | 0.55 | 3.52 | 0.77 |  |  | 3.51 | 0.78 |
| 10 | 3.27 | 0.71 | 1.91 | 0.86 |  |  | 1.87 | 0.85 |
| 11 | 1.80 | 1.15 | 1.43 | 0.97 |  |  | 1.41 | 0.99 |
| 12 | >33 | 0.00 | >33 | 0.00 |  |  | 10.04 | 0.09 |
| 13 | >33 | 0.00 | >33 | 0.09 |  |  | 20.36 | 0.22 |
| 14 | 6.60 | 0.33 | ~10 | 0.89 |  |  | 8.52 | 0.69 |
| 15 | 4.11 | 0.09 | 6.18 | 0.87 |  |  | 3.01 | 0.70 |
| 17 | 4.51 | 0.01 | ~5.5 | 0.40 |  |  | 3.47 | 0.43 |
| 18 | 3.96 | 0.29 | 3.27 | 0.53 |  |  | 3.41 | 0.67 |
| 20 | 4.00 | 0.92 | 2.56 | 0.71 |  |  | 2.06 | 0.75 |
| 21 | >33 | 0.00 | >33 | 0.09 |  |  | ~15 | 0.33 |

TABLE 5-continued

Biological Assay Results: Average $EC_{50}$/Rel Max FI

| Compound Example | 13B3 | | 27-63 | | AA_3T3 | | Z3 | |
|---|---|---|---|---|---|---|---|---|
| | EC50 (µM) | Rel Max FI | LC50 (µM) | Rel Max FI | LC50 (µM) | Rel Max FI | LC50 (µM) | Rel Max FI |
| 22 | >33 | 0.00 | 10.80 | 0.60 | | | ~10 | 0.48 |
| 25 | >33 | 0.00 | >33 | 0.00 | | | ~20 | 0.07 |
| 26 | ~20 | 0.11 | 11.00 | 0.83 | | | ~15 | 0.60 |
| 27 | ~20 | 0.36 | 10.00 | 0.96 | | | 10.00 | 0.81 |
| 28 | 3.25 | 0.74 | 1.80 | 0.85 | | | 1.60 | 0.98 |
| 29 | >33 | 0.00 | >33 | 0.00 | | | ~15 | 0.06 |
| 30 | >33 | 0.00 | >33 | 0.03 | | | ~15 | 0.20 |
| 31 | >33 | 0.08 | ~15 | 0.61 | | | 8.61 | 0.47 |
| 32 | >33 | 0.00 | >33 | 0.01 | | | 25.46 | 0.12 |
| 33 | >33 | 0.00 | >33 | 0.00 | | | ~20 | 0.05 |
| 34 | >33 | 0.00 | >33 | 0.00 | | | >33 | 0.04 |
| 37 | >33 | 0.08 | ~18 | 0.81 | | | 6.19 | 0.29 |
| 38 | >33 | 0.00 | >33 | 0.00 | | | 13.73 | 0.04 |
| 40 | ~15 | 0.58 | 6.61 | 0.67 | | | 5.16 | 0.70 |
| 42 | >33 | 0.00 | >33 | 0.01 | | | ~15 | 0.14 |
| 44 | >33 | 0.00 | >33 | 0.07 | | | 16.76 | 0.23 |
| 45 | 1.35 | 0.67 | 1.03 | 0.71 | | | 0.98 | 0.84 |
| 46 | >33 | 0.00 | >33 | 0.00 | | | >33 | 0.03 |
| 48 | 33.00 | 0.00 | >33 | 0.11 | | | 6.61 | 0.25 |
| 49 | >33 | 0.00 | >33 | 0.00 | | | >33 | 0.01 |
| 50 | >33 | 0.00 | >33 | 0.00 | | | 10.42 | 0.07 |
| 51 | ~15 | 0.64 | 6.23 | 0.54 | | | 4.53 | 0.61 |
| 52 | >33 | 0.00 | ~12 | 0.04 | | | 6.09 | 0.24 |
| 53 | >33 | 0.00 | >33 | 0.00 | | | 23.66 | 0.11 |
| 55 | 3.42 | 0.21 | 3.85 | 0.62 | | | 3.40 | 0.72 |
| 56 | >33 | 0.00 | >33 | 0.06 | | | 41.81 | 0.24 |
| 60 | >33 | 0.01 | ~9 | 0.35 | | | ~6 | 0.61 |
| 62 | >33 | 0.00 | ~30 | 0.04 | | | ~15 | 0.10 |
| 63 | >33 | 0.03 | 27.15 | 0.68 | | | 17.95 | 0.26 |
| 64 | 3.79 | 0.81 | 3.12 | 0.82 | | | 2.62 | 0.77 |
| 65 | ~20 | 0.03 | >20 | 0.28 | | | 8.84 | 0.06 |
| 66 | 23.83 | 0.50 | 14.55 | 0.76 | | | 3.33 | 0.17 |
| 67 | 17.62 | 0.50 | 6.59 | 0.77 | | | 4.17 | 0.54 |
| 68 | 8.79 | 1.00 | 3.70 | 0.98 | | | 2.83 | 0.70 |
| 69 | 19.39 | 0.19 | 14.43 | 0.84 | | | 7.52 | 0.56 |
| 70 | | | 3.36 | 0.66 | 3.21 | 0.48 | 1.94 | 0.78 |
| 71 | | | 2.97 | 0.88 | 8.18 | 0.42 | 1.61 | 0.69 |
| 75 | | | 41.95 | 0.29 | >33 | 0.02 | ~10 | 0.17 |
| 76 | | | >33 | 0.00 | | | >33 | 0.00 |
| 77 | | | >33 | 0.00 | | | 32.25 | 0.04 |
| 78 | | | 6.54 | 0.41 | >33 | 0.00 | >33 | 0.06 |
| 79 | | | 4.38 | 0.32 | >33 | 0.00 | 34.42 | 0.12 |
| 80 | | | 0.39 | 0.91 | | | 0.74 | 0.89 |
| 81 | | | 3.22 | 0.91 | | | 3.68 | 0.81 |
| 82 | | | 1.78 | 0.84 | | | 1.99 | 0.79 |
| 83 | | | 7.06 | 0.70 | | | 6.15 | 0.41 |
| 84 | | | 1.02 | 0.82 | | | 1.59 | 0.91 |
| 85 | | | 3.86 | 0.94 | | | 4.76 | 0.67 |
| 86 | | | 4.88 | 0.80 | | | 5.49 | 0.61 |
| 87 | | | 18.67 | 0.53 | | | 9.46 | 0.17 |
| 89 | | | >33 | 0.07 | >33 | 0.00 | | |
| 95 | | | | | | | 0.82 | 2.27 |
| 120 | 14.88 | 0.27 | 9.05 | 0.65 | | | 6.33 | 0.36 |
| 137 | | | >33 | 0.21 | >33 | 0.01 | | |
| 138 | | | 3.59 | 0.75 | ~4.7 | 0.22 | | |
| 139 | | | >33 | 0.00 | | | >33 | 0.00 |
| 140 | | | >33 | 0.00 | | | >33 | 0.00 |
| 141 | | | >33 | 0.00 | | | >33 | 0.00 |
| 142 | | | >33 | 0.00 | | | >33 | 0.00 |
| 143 | | | 1.50 | 0.91 | 2.81 | 0.59 | 1.81 | 0.85 |
| 144 | | | 1.52 | 0.93 | 2.67 | 0.70 | 2.15 | 0.86 |
| 156 | | | >33 | 0.00 | | | ~20 | 0.03 |
| 175 | | | | | | | 1.51 | 0.63 |

In addition, one of ordinary skill in the art is also able to predict that the ligands disclosed herein will also work to modulate gene expression in various cell types described above using gene expression systems based on group H and group B nuclear receptors.

---

We claim:

1. A method of modulating the expression of a target gene in a host cell, wherein the host cell includes a first gene expression cassette comprising a first polynucleotide encoding a first polypeptide comprising:
   (i) a transactivation domain;
   (ii) a DNA-binding domain; and
   (iii) a Group H nuclear receptor ligand binding domain;
a second gene expression cassette comprising:
   (i) a response element capable of binding to said DNA binding domain;
   (ii) a promoter that is activated by the transactivation domain; and
   (iii) said target gene;
the method comprising contacting said host cell with a compound of formula:

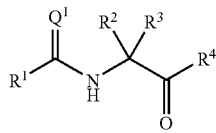

I wherein $Q^1$ is selected from the group consisting of O and S;
$R^1$ is
   i. $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_2-C_6)$haloalkenyl, $(C_2-C_6)$alkynyl, $(C_2-C_6)$haloalkynyl, $(C_1-C_6)$alkoxy, $(C_3-C_6)$cycloalkoxy, $(C_1-C_6)$haloalkoxy, $(C_3-C_6)$halocycloalkoxy, $(C_2-C_6)$alkenyloxy, $(C_2-C_6)$alkynyloxy, $(C_1-C_6)$alkylthio, $(C_3-C_6)$cycloalkylthio, 1-$C_6$)haloalkylthio, $(C_3-C_6)$halocycloalkylthio, $(C_1-C_6)$alkylamino, $(C_3-C_6)$cycloalkylamino, $(C_1-C_6)$haloalkylamino, $(C_3-C_6)$halocycloalkylamino, di$(C_1-C_6)$alkylamino, di$(C_3-C_6)$cycloalkylamino, di$(C_1-C_6)$haloalkylamino, di$(C_3-C_6)$halocycloalkylamino, $(C_1-C_6)$alkoxy$(C_1-C_6)$alkyl, $(C_1-C_6)$alkylthio$(C_1-C_6)$alkyl, $(C_1-C_6)$alkylsulfinyl$(C_1-C_6)$alkyl, $(C_1-C_6)$alkylsulfonyl$(C_{10}-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl$(C_1-C_6)$alkyl, or cyano$(C_1-C_6)$alkyl; or
   ii. unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, where the substituents are independently selected from one to four of the following:

i cyano, nitro, halo, aminocarbonyl, aminothiocarbonyl, carboxy, formyl, hydroxy, amino, carbamoyl, $(C_1-C_6)$alkyl, $(C_3-C_6)$cycloalkyl, $(C_1-C_6)$ haloalkyl, $(C_3-C_6)$halocycloalkyl, $(C_2-C_6)$alkenyl, $(C_3-C_6)$cycloalkenyl, $(C_3-C_6)$alkadienyl, $(C_2-C_6)$alkynyl, $(C_1-C_6)$alkoxy, $(C_3-C_6)$cycloalkoxy, $(C_1-C_6)$haloalkoxy, $(C_3-C_6)$cyclohaloalkoxy, $(C_2-C_6)$alkenyloxy, $(C_2-C_6)$alkynyloxy, $(C_1-C_6)$alkylthio, $(C_3-C_6)$cycloalkylthio, $(C_1-C_6)$haloalkylthio, $(C_3-C_6)$halocycloalkythio, $(C_2-C_6)$alkenylthio, $(C_2-C_6)$alkynylthio, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_2-C_6)$alkenylsulfinyl, $(C_3-C_6)$cycloalkenylsulfinyl, $(C_2-C_6)$alkynylsulfinyl, $(C_1-C_6)$alkylsulfonyl, $(C_3-C_6)$cycloalkysulfonyl, $(C_1-C_6)$haloalkylsulfonyl, $(C_3-C_6)$halocycloalkylsulfonyl, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_1-C_6)$alkylamino, $(C_3-C_6)$cycloalkylamino, di$(C_1-C_6)$alkylamino, di$(C_3-C_6)$(cycloalkyl)amino, $(C_1-C_6)$alkoxy$(C_1-C_6)$alkyl, $(C_3-C_6)$cycloalkoxyalkyl, $(C_1-C_6)$alkoxy$(C_3-C_6)$cycloalkyl, $(C_1-C_6)$ alkylthio$(C_1-C_6)$alkyl, $(C_1-C_6)$alkylsulfinyl$(Ct-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$ alkyl, $(C_1-C_6)$alkylcarbonyl, $(C_3-C_6)$cycloalkylcarbonyl, $(C_1-C_6)$alkoxycarbonyl, $(C_1-C_6)$alkylaminocarbonyl, $(C_3-C_6)$cycloalkylaminocarbonyl, di$(C_1-C_6)$alkylaminocarbonyl, di$(C_3-C_6)$(cycloalkyl)aminocarbonyl, cyano$(C_1-C_6)$alkyl, or tri$(C_1-C_6)$alkylsilyl; or
   ii unsubstituted or substituted phenyl, phenyl$(C_1-C_6)$alkyl, heterocyclyl, phenoxy, heterocyclyloxy, benzoyl, heterocyclylcarbonyl, phenylthio, heterocyclylthio, phenylsulfonyl, or heterocyclylsulfonyl wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, i -$C_2$)alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl or cyano$(C_1-C_3)$ alkyl;
wherein in said substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein: the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$ alkylamino, $(C_1-C_2)$alkoxy$(C_1-C_2)$alkyl, $(C_1-C_2)$alkylthio$(C_1-C_2)$alkyl, $(C_1-C_2)$ alkylsulfonyl$(C_1-C_2)$alkyl, $(C_1-C_2)$alkylamino$(C_1-C_2)$alkyl, di$(C_1-C_2)$alkylamino$(C_1-C_2)$ alkyl, $(C_1-C_3)$alkylcarbonyl, 1-$C_3$)alkoxycarbonyl, $(C_1-C_3)$alkylaminocarbonyl, di$(C_1-C_3)$alkylaminocarbonyl, cyano$(C_1-C_3)$alkyl, oxo, and methoxyimino; $R^2$ and $R^3$ are independently selected from:

(a) cyano, aminocarbonyl, carboxy, $(C_1-C_6)$alkyl, $(C_3-C_6)$cycloalkyl, halo$(C_1-C_6)$ alkyl, $(C_3-C_6)$halocycloalkyl, $(C_2-C_6)$alkenyl, $(C_3-C_6)$cycloalkenyl, $(C_2-C_6)$ haloalkenyl, $(C_2-C_6)$alkynyl, $(C_1-C_6)$alkylsulfonyl, $(C_1-C_6)$ alkoxy$(C_1-C_6)$alkyl, $(C_1-C_6)$ alkylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl, $(C_1-C_6)$alkylcarbonyl$(C_1-C_6)$alkyl, $(C_1-C_6)$alkylaminocarbonyl, di$(C_1-C_6)$ alkylaminocarbonyl, $(C_1-C_6)$alkylaminocarbonyl$(C_1-C_6)$alkyl, di$(C_1-C_6)$alkylaminocarbonyl$(C_1-C_6)$alkyl, $(C_1-C_6)$alkylcarbonylamino$(C_1-C_6)$alkyl, $(C_1-C_6)$ alkoxycarbonyl, $(C_1-C_6)$alkoxycarbonyl$(C_1-C_6)$alkyl, cyano$(C_1-C_6)$alkyl, hydroxy$(C_1-C_6)$ alkyl, or carboxy$(C_1-C_6)$alkyl; or (b) unsubstituted or substituted phenyl, phenyl$(C_1-C_6)$ alkyl, benzoyl, naphthyl, pyridyl, pyrazinyl, pyridazinyl, pyrimidinyl, furanyl, thiophenyl, benzothiophenyl, benzofuranyl, isoxazolyl, imidazolyl or other heterocyclyl, heterocyclylcarbonyl, wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$ alkoxy, $(C_1-C_3)$ haloalkoxy, $(C_1-C_3)$alkythio, $(C_1-C_3)$haloalkylthio, $(C_1-C_3)$alkylsulfonyl, $(C_1-C_3)$ alkylamino, di$(C_1-C_3)$alkylamino, $(C_1-C_2)$alkoxy$(C_1-C_2)$alkyl, $(C_1-C_2)$alkylthio$(C_1-C_2)$ alkyl, $(C_1-C_2)$alkylsulfonyl$(C_1-C_2)$alkyl, $(C_1-C_2)$alkylamino$(C_1-C_2)$alkyl, di$(C_1-C_2)$ alkylamino$(C_1-C_2)$alkyl, $(C_1-C_3)$alkylcarbonyl, $(C_1-C_3)$alkoxycarbonyl, $(C_1-C_3)$ alkylaminocarbonyl, di$(C_1-C_3)$alkylaminocarbonyl, and cyano$(C_1-C_3)$ alkyl;

wherein $R^2$ and $R^3$ may be joined together with the carbon to which they are attached to form an unsubstituted or substituted, partially unsaturated or saturated 3-, 4-, 5-, 6-, 7- or 8-membered carbocyclic or heterocyclic ring wherein the heterocyclic ring contains from one to three heteroatoms selected from O, N, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$ haloalkyl, $(C_1-C_3)$alkoxy, $(C_1-C_3)$haloalkoxy, $(C_1-C_3)$ alkythio, $(C_1-C_3)$haloalkylthio, $(C_1-C_3)$alkylsulfonyl, 1-$C_3$) alkylamino, di$(C_1-C_3)$alkylamino, $(C_1-C_2)$alkoxy$(C_1-C_2)$ alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$ alkyl, di$(C_1-C_2)$ alkylamino$(C_1-C_2)$alkyl, $(C_1-C_3)$alkylcarbonyl, $(C_1-C_4)$ alkoxycarbonyl, $(C_1-C_4)$alkoxycarbonyl$(C_1-C_4)$alkyl, $(C_1-C_4)$alkoxycarbonylcarbonyl, $(C_1-C_3)$alkylaminocarbonyl, di$(C_1-C_3)$alkylaminocarbonyl, cyano$(C_1-C_3)$alkyl, oxo, methoxyimino, and spiro-$(C_1-C_4)$alkadioxy; and $R^4$ is selected from:

(a) $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_3-C_6)$cycloalkoxy, $(C_1-C_6)$haloalkoxy, $(C_3-C_6)$halocycloalkoxy, $(C_2-C_6)$alkenyloxy, $(C_2-C_6)$alkynyloxy, $(C_1-C_6)$alkylthio, $(C_3-C_6)$cycloalkylthio, $(C_1-C_6)$haloalkylthio, $(C_3-C_6)$halocycloalkylthio, $(C_1-C_6)$alkylamino, $(C_3-C_6)$cycloalkylamino, $(C_1-C_6)$ haloalkylamino, $(C_3-C_6)$halocycloalkylamino, di$(C_1-C_6)$alkylamino, di$(C_3-C_6)$ cycloalkylamino, di$(C_1-C_6)$haloalkylamino, di$(C_3-C_6)$halocycloalkylamino, $(C_1-C_6)$ alkoxy$(C_1-C_6)$alkyl, $(C_1-C_6)$alkylthio$(C_1-C_6)$alkyl, $(C_1-C_6)$alkylsulfinyl $(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$ alkylamino$(C_1-C_6)$alkyl, $(C_1-C_6)$alkylcarbonyl$(C_1-C_6)$alkyl, or cyano $(C_1-C_6)$alkyl; or (b) unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein one to four substituents are independently selected from:

i cyano, nitro, halo, aminocarbonyl, aminothiocarbonyl, carboxy, formyl, hydroxy, amino, carbamoyl, $(C_1-C_6)$alkyl, $(C_3-C_6)$cycloalkyl, $(C_1-C_6)$ haloalkyl, $(C_3-C_6)$halocycloalkyl, $(C_2-C_6)$alkenyl, $(C_3-C_6)$cycloalkenyl, $(C_3-C_6)$alkadienyl, $(C_2-C_6)$alkynyl, $(C_1-C_6)$alkoxy, $(C_3-C_6)$cycloalkoxy, $(C_1-C_6)$haloalkoxy, $(C_3-C_6)$cyclohaloalkoxy, $(C_2-C_6)$alkenyloxy, $(C_2-C_6)$ alkynyloxy, $(C_1-C_6)$alkylthio, $(C_3-C_6)$cycloalkylthio, $(C_1-C_6)$ haloalkylthio, $(C_3-C_6)$halocycloalkythio, $(C_2-C_6)$alkenylthio, $(C_2-C_6)$ alkynylthio, $(C_1-C_6)$alkylsulfinyl, $(C_3-C_6)$cycloalkysulfinyl, $(C_1-C_6)$ haloalkylsulfinyl, $(C_3-C_6)$ halocycloalkylsulfinyl, $(C_2-C_6)$ alkenylsulfinyl, $(C_3-C_6)$cycloalkenylsulfinyl, $(C_2-C_6)$alkynylsulfinyl, $(C_1-C_6)$alkylsulfonyl, $(C_3-C_6)$cycloalkysulfonyl, $(C_1-C_6)$haloalkylsulfonyl, $(C_3-C_6)$halocycloalkylsulfonyl, $(C_1-C_6)$alkylsulfinyl, $(C_3-C_6)$ cycloalkysulfinyl, 1-$C_6$)haloalkylsulfinyl, $(C_3-C_6)$ halocycloalkylsulfinyl, $(C_1-C_6)$alkylamino, $(C_3-C_6)$ cycloalkylamino, di$(C_1-C_6)$alkylamino, di$(C_3-C_6)$ (cycloalkyl)amino, $(C_1-C_6)$alkoxy$(C_1-C_6)$ alkyl, $(C_3-C_6)$cycloalkoxyalkyl, $(C_1-C_6)$alkoxy$(C_3-C_6)$cycloalkyl, $(C_1-C_6)$ alkylthio$(C_1-C_6)$alkyl, $(C_1-C_6)$ alkylsulfinyl$(C_1-C_6)$alkyl, $(C_1-C_6)$ alkylsulfonyl$(C_1-C_6)$alkyl, $(C_1-C_6)$alkylamino$(C_1-C_6)$alkyl, di$(C_1-C_6)$ alkylamino$(C_1-C_6)$alkyl, $(C_1-C_6)$alkylcarbonyl, $(C_3-C_6)$ cycloalkylcarbonyl, $(C_1-C_6)$alkoxycarbonyl, $(C_1-C_6)$ alkylaminocarbonyl, $(C_3-C_6)$cycloalkylaminocarbonyl, di$(C_1-C_6)$ alkylaminocarbonyl, di$(C_3-C_6)$(cycloalkyl)aminocarbonyl, cyano$(C_1-C_6)$ alkyl, or tri$(C_1-C_6)$alkylsilyl; or ii unsubstituted or substituted phenyl, phenyl$(C_1-C_6)$ alkyl, heterocyclyl, phenoxy, heterocyclyloxy, benzoyl, heterocyclylcarbonyl, phenylthio, heterocyclylthio, phenylsulfonyl, or heterocyclylsulfonyl, wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$ haloalkyl, $(C_1-C_3)$alkoxy, $(C_1-C_3)$haloalkoxy, $(C_1-C_3)$alkythio, $(C_1-C_3)$ haloalkylthio, $(C_1-C_3)$alkylsulfonyl, 1-$C_3)$alkylamino, di$(C_1-C_3)$ alkylamino, $(C_1-C_2)$alkoxy$(C_1-C_2)$alkyl, $(C_1-C_2)$ alkylthio$(C_1-C_2)$alkyl, $(C_1-C_2)$alkylsulfonyl$(C_1-C_2)$ alkyl, $(C_1-C_2)$alkylamino$(C_1-C_2)$ alkyl, di$(C_1-C_2)$ alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl and cyano$(C_1-C_3)$ alkyl;

wherein in said substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions on $R^4$ may be joined together with the atoms to which they are attached to form an unsubstituted or substituted, unsaturated, partially unsaturated, or saturated 4-, 5-, 6- or 7-membered carbocyclic or heterocyclic ring wherein the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$ alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano $(C_1-C_3)$alkyl, oxo, and methoxyimino.

2. The method of claim 1 wherein the compound is of the specified formula and:

$Q^1$ is O, $R^1$ is unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, where the substituents are independently selected from the group consisting of one to four of the following groups: cyano, nitro, halo, amino, $(C_1-C_3)$alkyl, $(C_1-C_3)$haloalkyl, $(C_1-C_3)$alkoxy, $(C_1-C_3)$haloalkoxy, $(C_3)$alkenyloxy, $(C_3)$alkynyloxy, $(C_1-C_3)$alkythio, $(C_1-C_3)$haloalkylthio, $(C_3)$alkenylthio, $(C_3)$alkynylthio, $(C_1-C_3)$alkylsulfonyl, $(C_1-C_3)$haloalkylsulfonyl, $(C_1-C_3)$alkylsulfinyl, $(C_1-C_3)$haloalkylsulfinyl $(C_1-C_3)$alkylamino, di$(C_1-C_3)$alkylamino, $(C_1-C_2)$alkoxy$(C_1-C_2)$alkyl, $(C_1-C_2)$ alkylthio$(C_1-C_2)$alkyl, $(C_1-C_2)$alkylsulfinyl$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino $(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, and cyano$(C_1-C_3)$alkyl; and wherein in said substituted phenyl, 1-naphthyl, 2-naphthyl, phenyl$(C_1-C_3)$alkyl, phenyl$(C_2-C_3)$alkenyl, naphthyl $(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein:

the heterocyclic ring contains from one to three heteroatoms selected from N, 0, or and one to four substituents are independently selected from the group consisting of: cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino and $R^4$ is selected from unsubstituted or substituted phenyl, 1-naphthyl, 2-naphthyl, phenyl$(C_1-C_3)$alkyl, phenyl$(C_2-C_3)$ alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein one to four substituents are independently selected from:

(a) cyano, nitro, halo, carboxy, formyl, hydroxy, amino, $(C_1-C_3)$alkyl, $(C_1-C_3)$haloalkyl, $(C_1-C_3)$alkoxy, $(C_1-C_3)$haloalkoxy, $(C_3)$alkenyloxy, $(C_3)$alkynyloxy, $(C_1-C_3)$alkythio, $(C_1-C_3)$haloalkylthio, $(C_1-C_3)$alkylsulfinyl, $(C_1-C_3)$haloalkylsulfinyl, $(C_1-C_3)$alkylsulfonyl, 1-$C_3)$haloalkylsulfonyl, 1-$C_3)$alkylamino, di$(C_1-C_3)$ alkylamino, $(C_1-C_2)$alkoxy$(C_1-C_2)$alkyl, $(C_1-C_2)$alkylthio$(C_1-C_2)$alkyl, $(C_1-C_2)$alkylsulfinyl$(C_1-C_2)$alkyl, $(C_1-C_2)$alkylsulfonyl$(C_1-C_2)$alkyl, $(C_1-C_2)$alkylamino $(C_1-C_2)$alkyl, di$(C_1-C_2)$alkylamino$(C_1-C_2)$ alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, or cyano$(C_1-C_3)$alkyl; or (b) unsubstituted or substituted phenyl, phenyl$(C_1-C_2)$ alkyl, heterocyclyl, phenoxy, heterocyclyloxy, benzoyl, heterocyclylcarbonyl, phenylthio, heterocyclylthio, phenylsulfonyl, or heterocyclylsulfonyl, wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$ alkoxy, $(C_1-C_3)$haloalkoxy, $(C_1-C_3)$alkythio, $(C_1-C_3)$ haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$ alkyl, $(C_1-C_2)$alkylthio$(C_1-C_2)$alkyl, $(C_1-C_2)$ alkylsulfonyl$(C_1-C_2)$alkyl, $(C_1-C_2)$alkylamino$(C_1-C_2)$ alkyl, di$(C_1-C_2)$alkylamino$(C_1-C_2)$alkyl, $(C_1-C_3)$ alkylcarbonyl, $C_3)$alkoxycarbonyl, $(C_1-C_3)$ alkylaminocarbonyl, di$(C_1-C_3)$alkylaminocarbonyl, and cyano$(C_1-C_3)$alkyl; and wherein two adjacent positions on may be joined together with the atoms to which they are attached to form an unsubstituted or substituted, unsaturated, partially unsaturated, or saturated 4-, 5-, 6- or 7-membered carbocyclic or heterocyclic ring wherein:

the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$ haloalkoxy, $(C_1-C_3)$alkythio, $(C_1-C_3)$haloalkylthio, $C_1-C_3)$ alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_9$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino 3. The method of claim 2 wherein the compound is of the specified formula and $R^1$ is unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein the substituents are independently selected from the group consisting of one to four of the following groups: halo, $(C_1-C_3)$alkyl, $(C_1-C_3)$alkoxy, $(C_1-C_3)$alkythio, $(C_1-C_3)$alkylsulfonyl, $(C_1-C_3)$alkylsulfinyl, $(C_1-C_3)$alkylamino, and di$(C_1-C_3)$alkylamino;

wherein in said substituted phenyl, naphthyl or heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein:

the heterocyclic ring contains from one to three heteroatoms selected from N, O, or S; and one to four substituents are independently selected from the group consisting of: cyano, $(C_1-C_3)$alkyl, $(C_1-C_3)$alkoxy, $(C_1-C_3)$alkythio, $(C_1-C_3)$alkylsulfonyl, $(C_1-C_3)$alkylamino, di$(C_1-C_3)$alkylamino, $(C_1-C_3)$alkoxycarbonyl, $(C_1-C_3)$alkylaminocarbonyl, di$(C_1-C_3)$alkylaminocarbonyl, oxo, and methoxyimino;

$R^2$ and $R^3$ are independently selected from the group consisting of: $(C_1-C_6)$alkyl, $(C_3-C_6)$cycloalkyl, halo$(C_1-C_6)$alkyl, $(C_3-C_6)$halocycloalkyl, $(C_2-C_6)$alkenyl, $(C_3-C_6)$cycloalkenyl, $(C_2-C_6)$haloalkenyl, $(C_2-C_6)$alkynyl, $(C_1-C_3)$alkoxy$(C_1-C_3)$alkyl, $(C_1-C_3)$alkylthio$(C_1-C_3)$alkyl, $(C_1-C_3)$alkylsulfinyl$(C_1-C_3)$alkyl, $(C_1-C_3)$alkylsulfonyl$(C_1-C_3)$alkyl, $(C_1-C_3)$alkylamino$(C_1-C_3)$alkyl, di$(C_1-C_3)$alkylamino$(C_1-C_3)$alkyl, $(C_1-C_6)$alkylcarbonyl, $(C_1-C_3)$alkylcarbonyl$(C_1-C_3)$alkyl, $(C_1-C_6)$alkylaminocarbonyl, di$(C_1-C_6)$alkylaminocarbonyl, $(C_1-C_3)$alkylaminocarbonyl$(C_1-C_3)$alkyl, di$(C_1-C_3)$alkylaminocarbonyl$(C_1-C_3)$alkyl, $(C_1-C_3)$alkylcarbonylamino$(C_1-C_3)$alkyl, $(C_1-C_6)$alkoxycarbonyl, $(C_1-C_3)$alkoxycarbonyl$(C_1-C_3)$alkyl, cyano$(C_1-C_6)$alkyl, hydroxy$(C_1-C_6)$alkyl, and carboxy$(C_1-C_6)$alkyl;

wherein $R^2$ and $R^3$ may be joined together with the carbon to which they are attached to form an unsubstituted or substituted, partially unsaturated or saturated 3-, 4-, 5-, 6- or 7- membered carbocyclic or heterocyclic ring, wherein the heterocyclic ring contains from one to three heteroatoms selected from O or S; and one to four substituents are independently selected from the group consisting of cyano, $(C_1-C_3)$alkyl, $(C_1-C_3)$alkoxy, $(C_1-C_3)$alkythio, $(C_1-C_3)$alkylsulfonyl, 1-$(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_4)$alkoxycarbonyl, $(C_1-C_3)$alkylaminocarbonyl, and di$(C_1-C_3)$alkylaminocarbonyl; and $R^4$ is selected from unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein one to four substituents are independently selected from the group consisting of cyano, nitro, halo, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfinyl, $(C_1-C_3)$haloalkylsulfinyl, $(C_1-C_3)$alkylsulfonyl, $(C_1-C_3)$haloalkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfinyl$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, 1-$C_3$)alkoxycarbonyl, $(C_1-C_3)$alkylaminocarbonyl, and di$(C_1-C_3)$alkylaminocarbonyl;

wherein two adjacent positions on may be joined together with the atoms to which they are attached to form an unsubstituted or substituted, unsaturated, partially unsaturated, or saturated 5-, 6- or 7-membered carbocyclic or heterocyclic ring wherein the heterocyclic ring contains from one to three heteroatoms selected from N, O, or S; and one to four substituents are independently selected from the group consisting of cyano, 1-$C_3$)alkyl, $(C_1-C_3)$alkoxy, $(C_1-C_3)$alkythio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, 1-$(C_4)$alkoxycarbonyl, $(C_1-C_3)$alkylaminocarbonyl, di$(C_1-C_3)$alkylaminocarbonyl, oxo, and methoxyimino.

4. The method of claim 3 wherein the compound is of the specified formula and:

$R^1$ is substituted phenyl wherein one to two substituents are independently selected from the group consisting of $(C_1-C_2)$alkyl and $(C_1-C_2)$alkoxy;

wherein in said substituted phenyl, two adjacent positions are joined together with the atoms to which they are attached to form an unsubstituted or substituted, unsaturated, partially unsaturated, or saturated 5-, 6- or 7-membered carbocyclic or heterocyclic ring wherein:

the heterocyclic ring contains from one to two oxygen atoms; and one to four substituents are independently selected from the group consisting of: cyano, $(C_1-C_2)$alkyl, $(C_1-C_2)$alkylamino, di$(C_1-C_2)$alkylamino, $(C_1-C_2)$alkoxycarbonyl, $(C_1-C_2)$alkylaminocarbonyl, di$(C_1-C_2)$alkylaminocarbonyl, oxo, and methoxyimino;

$R^2$ and $R^3$ are independently selected from the group consisting of: $(C_1-C_6)$alkyl, $(C_3-C_6)$cycloalkyl, halo$(C_1-C_6)$alkyl, $(C_1-C_3)$alkoxy$(C_1-C_3)$alkyl, $(C_1-C_3)$alkylthio$(C_1-C_3)$alkyl, $(C_1-C_3)$alkylsulfinyl$(C_1-C_3)$alkyl, $(C_1-C_3)$alkylsulfonyl$(C_1-C_3)$alkyl, $(C_1-C_3)$alkylamino$(C_1-C_3)$alkyl, di$(C_1-C_3)$alkylamino$(C_1-C_3)$alkyl, $(C_1-C_6)$alkylcarbonyl, $(C_1-C_3)$alkylcarbonyl$(C_1-C_3)$alkyl, $(C_1-C_6)$alkylaminocarbonyl, di$(C_1-C_6)$alkylaminocarbonyl, $(C_1-C_3)$alkylaminocarbonyl$(C_1-C_3)$alkyl, di$(C_1-C_3)$alkylaminocarbonyl$(C_1-C_3)$alkyl, $(C_1-C_3)$alkylcarbonylamino$(C_1-C_3)$alkyl, $(C_1-C_6)$alkoxycarbonyl, and $(C_1-C_3)$alkoxycarbonyl$(C_1-C_3)$alkyl;

wherein $R^2$ and $R^3$ may be joined together with the carbon to which they are attached to form an unsubstituted or substituted, partially unsaturated or saturated 5-, 6- or 7-membered carbocyclic or heterocyclic ring wherein:

the heterocyclic ring contains one heteroatom selected from O or S; and one to four substituents are independently selected from the group consisting of$(C_1-C_3)$alkyl, $(C_1-C_3)$alkylamino, di$(C_1-C_3)$alkylamino, $(C_1-C_4$alkoxycarbonyl, $(C_1-C_3)$alkylaminocarbonyl, and di$(C_1-C_3)$alkylaminocarbonyl; and $R^4$ is selected from unsubstituted or substituted phenyl or pyridyl wherein one to four substituents are independently selected from the group consisting of $(C_1-C_3)$alkyl and $(C_1-C_3)$alkoxy;

5. The method of claim 4 wherein the compound is of the specified formula and $R^1$ is selected from the group consisting of 2-methyl-3,4-methylenedioxyphenyl, 2-ethyl-3,4-methylenedioxyphenyl, 2-methyl-3,4-ethylenedioxyphenyl, 2-ethyl-3,4-ethylenedioxyphenyl, 2-methyl-3,4-oxydimethylenephenyl, 2-ethyl-3,4-oxydimethylenephenyl, 2-methyl-3,4-oxytrimethylenephenyl, and 2-ethyl-3,4-oxytrimethylenephenyl;

6. The method of claim 5 wherein the compound is of the specified formula and $R^1$ is 2-methyl-3-methoxyphenyl, $R^2$ and $R^3$ taken together with the carbon to which they are attached form a cyclohexane ring and $R^4$ is 3,5-dimethylphenyl or 2-methoxyphenyl.

7. A method to modulate the expression of one or more exogenous genes in a subject, comprising administering to the subject an effective amount of a ligand of the formula:

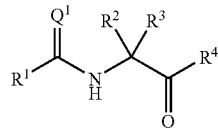

I wherein $Q^1$ is selected from the group consisting of O and S;

$R^1$ is (a) $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_2-C_6)$haloalkenyl, $(C_2-C_6)$alkynyl, $(C_2-C_6)$haloalkynyl, $(C_1-C_6)$alkoxy, $(C_3-C_6)$cycloalkoxy, $(C_1-C_6)$haloalkoxy, $(C_3-C_6)$halocycloalkoxy, $(C_2-C_6)$alkenyloxy, $(C_2-C_6)$alkynyloxy, $(C_1-C_6)$alkylthio, $(C_3-C_6)$cycloalkylthio, $(C_1-C_6)$haloalkylthio, $(C_3-C_6)$halocycloalkylthio, $(C_1-C_6)$alkylamino, $(C_3-C_6)$cycloalkylamino, $(C_1-C_6)$haloalkylamino, $(C_3-C_6)$halocycloalkylamino, di$(C_1-C_6)$alkylamino, di$(C_3-C_6)$cycloalkylamino, di$(C_1-C_6)$haloalkylamino, di$(C_3-C_6)$halocycloalkylamino, $(C_1-C_6)$alkoxy$(C_1-C_6)$alkyl, $(C_1-C_6)$alkylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl$(C_1-C_6)$alkyl, or cyano$(C_1-C_6)$alkyl; or (b) unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, where the substituents are independently selected from one to four of the following:

i cyano, nitro, halo, aminocarbonyl, aminothiocarbonyl, carboxy, formyl, hydroxy, amino, carbamoyl, $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_3-C_6)$cycloalkenyl, $(C_3-C_6)$alkadienyl, $(C_2-C_6)$alkynyl, $(C_1-C_6)$alkoxy, $(C_3-C_6)$cycloalkoxy, $(C_1-C_6)$haloalkoxy, $(C_3-C_6)$cyclohaloalkoxy, $(C_2-C_6)$alkenyloxy, $(C_2-C_6)$alkynyloxy, $(C_1-C_6)$alkythio, $(C_3-C_6)$cycloalkylthio, $(C_1-C_6)$haloalkylthio, $(C_3-C_6)$halocycloalkythio, $(C_2-C_6)$alkenylthio, $(C_2-C_6)$alkynylthio, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_2-C_6)$alkenylsulfinyl, $(C_3-C_6)$cycloalkenylsulfinyl, $(C_2-C_6)$alkynylsulfinyl, $(C_1-C_6)$alkylsulfonyl, $(C_3-C_6)$cycloalkysulfonyl, 1-$C_6$)haloalkylsulfonyl, $(C_3-C_6)$halocycloalkylsulfonyl, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_1-C_6)$alkylamino, $(C_3-C_6)$cycloalkylamino, di$(C_1-C_6)$alkylamino, di$(C_3-C_6)$(cycloalkyl)amino, $(C_1-C_6)$alkoxy$(C_1-C_6)$alkyl, $(C_3-C_6)$cycloalkoxyalkyl, $(C_1-C_6)$alkoxy$(C_3-C_6)$cycloalkyl, $(C_1-C_6)$alkylthio$(C_1-C_6)$alkyl, $(C_1-C_6)$alkylsulfinyl$(C_1-C_6)$alkyl, $(C_1-C_6)$alkylsulfonyl $(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl, $(C_3-C_6)$cycloalkylcarbonyl, $(C_1-C_6)$alkoxycarbonyl, $(C_1-C_6)$alkylaminocarbonyl, $(C_3-C_6)$cycloalkylaminocarbonyl, di$(C_1-C_6)$alkylaminocarbonyl, di$(C_3-C_6)$(cycloalkyl) aminocarbonyl, cyano$(C_1-C_6)$alkyl, or tri$(C_1-C_6)$alkylsilyl; or ii unsubstituted or substituted phenyl, phenyl$(C_1-C_6)$alkyl, heterocyclyl, phenoxy, heterocyclyloxy, benzoyl, heterocyclylcarbonyl, phenylthio, heterocyclylthio, phenylsulfonyl, or heterocyclylsulfonyl wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, 1-$C_3$)alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$ alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl or cyano$(C_1-C_3)$alkyl;

wherein in said substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein:

the heterocyclic ring contains from one to three heteroatoms selected from N, O, or and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(Ct -C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino;

$R^2$ and $R^3$ are independently selected from:

(a) cyano, aminocarbonyl, carboxy, $(C_1-C_6)$alkyl, $(C_3-C_6)$cycloalkyl, halo$(C_1-C_6)$alkyl, $(C_3-C_6)$halocycloalkyl, $(C_2-C_6)$alkenyl, $(C_3-C_6)$cycloalkenyl, $(C_2-C_6)$haloalkenyl, $(C_2-C_6)$alkynyl, $(C_1-C_6)$alkylsulfonyl, $(C_1-C_6)$alkoxy$(C_1-C_6)$alkyl, $(C_1-C_6)$alkylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl, $(C_1-C_6)$alkylcarbonyl$(C_1-C_6)$alkyl, $(C_1-C_6)$alkylaminocarbonyl, di$(C_1-C_6)$alkylaminocarbonyl, $(C_1-C_6)$alkylaminocarbonyl $(C_1-C_6)$alkyl, di$(C_1-C_6)$alkylaminocarbonyl$(C_1-C_6)$alkyl, $(C_1-C_6)$ alkylcarbonylamino($C_1$-$C_6$)alkyl, ($C_1$-$C_6$) alkoxycarbonyl, ($C_1$-$C_6$)alkoxycarbonyl($C_1$-$C_6$)alkyl, cyano($C_1$-$C_6$)alkyl, hydroxy($C_1$-$C_6$)alkyl, or carboxy ($C_1$-$C_6$)alkyl; or (b) unsubstituted or substituted phenyl, phenyl($C_1$-$C_6$) alkyl, benzoyl, naphthyl, pyridyl, pyrazinyl, pyridazinyl, pyrimidinyl, furanyl, thiophenyl, benzothiophenyl, benzofuranyl, isoxazolyl, imidazolyl or other heterocyclyl, heterocyclylcarbonyl, wherein one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$) alkoxy, ($C_1$-$C_3$)haloalkoxy, ($C_1$-$C_3$)alkythio, ($C_1$-$C_3$) haloalkylthio, ($C_1$-$C_3$)alkylsulfonyl, ($C_1$-$C_3$) alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$) alkylsulfonyl($C_1$-$C_2$)alkyl, ($C_1$-$C_2$)alkylamino($C_1$-$C_2$) alkyl, di($C_1$-$C_2$)alkylamino($C_1$-$C_2$)alkyl, ($C_1$-$C_3$) alkylcarbonyl, 1-$C_3$)alkoxycarbonyl, ($C_1$-$C_3$) alkylaminocarbonyl, di($C_1$-$C_3$)alkylaminocarbonyl, and cyano($C_1$-$C_3$)alkyl;

wherein $R^2$ and $R^3$ may be joined together with the carbon to which they are attached to form an unsubstituted or substituted, partially unsaturated or saturated 3-, 4-, 5-, 6-, 7- or 8-membered carbocyclic or heterocyclic ring wherein the heterocyclic ring contains from one to three heteroatoms selected from O, N, or S; and one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$) haloalkyl, ($C_1$-$C_3$)alkoxy, ($C_1$-$C_3$)haloalkoxy, ($C_1$-$C_3$) alkythio, ($C_1$-$C_3$)haloalkylthio, ($C_1$-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$) alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_4$)alkoxycarbonyl, ($C_1$-$C_4$)alkoxycarbonyl($C_1$-$C_4$) alkyl, ($C_1$-$C_4$)alkoxycarbonylcarbonyl, ($C_1$-$C_3$)alkylaminocarbonyl, di($C_1$-$C_3$)alkylaminocarbonyl, cyano($C_1$-$C_3$) alkyl, oxo, methoxyimino, and spiro-($C_1$-$C_4$)alkadioxy; and $R^4$ selected from:

(a) ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_3$-$C_6$)cycloalkoxy, ($C_1$-$C_6$)haloalkoxy, ($C_3$-$C_6$)halocycloalkoxy, ($C_2$-$C_6$)alkenyloxy, ($C_2$-$C_6$)alkynyloxy, ($C_1$-$C_6$)alkylthio, ($C_3$-$C_6$) cycloalkylthio, ($C_1$-$C_6$)haloalkylthio, ($C_3$-$C_6$) halocycloalkylthio, ($C_1$-$C_6$)alkylamino, ($C_3$-$C_6$) cycloalkylamino, ($C_1$-$C_6$)haloalkylamino, ($C_3$-$C_6$) halocycloalkylamino, di($C_1$-$C_6$)alkylamino, di($C_3$-$C_6$) cycloalkylamino, di($C_1$-$C_6$)haloalkylamino, di($C_3$-$C_6$) halocycloalkylamino, ($C_1$-$C_6$)alkoxy($C_1$-$C_6$)alkyl, ($C_1$-$C_6$)alkylthio($C_1$-$C_6$)alkyl, ($C_1$-$C_6$)alkylsulfinyl($C_1$-$C_6$) alkyl, ($C_1$-$C_6$)alkylsulfonyl($C_1$-$C_6$)alkyl, ($C_1$-$C_6$) alkylamino($C_1$-$C_6$)alkyl, di($C_1$-$C_6$)alkylamino($C_1$-$C_6$) alkyl, ($C_1$-$C_6$)alkylcarbonyl($C_1$-$C_6$)alkyl, or cyano($C_1$-$C_6$)alkyl; or (b) unsubstituted or substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein one to four substituents are independently selected from:

i cyano, nitro, halo, aminocarbonyl, aminothiocarbonyl, carboxy, formyl, hydroxy, amino, carbamoyl, ($C_1$-$C_6$)alkyl, ($C_3$-$C_6$)cycloalkyl, ($C_1$-$C_6$)haloalkyl, ($C_3$-$C_6$)halocycloalkyl, ($C_2$-$C_6$)alkenyl, ($C_3$-$C_6$)cycloalkenyl, ($C_3$-$C_6$)alkadienyl, ($C_2$-$C_6$)alkynyl, ($C_1$-$C_6$)alkoxy, ($C_3$-$C_6$)cycloalkoxy, ($C_1$-$C_6$)haloalkoxy, ($C_3$-$C_6$)cyclohaloalkoxy, ($C_2$-$C_6$)alkenyloxy, ($C_2$-$C_6$)alkynyloxy, ($C_1$-$C_6$)alkylthio, ($C_3$-$C_6$)cycloalkylthio, ($C_1$-$C_6$)haloalkylthio, ($C_3$-$C_6$)halocycloalkythio, ($C_2$-$C_6$)alkenylthio, ($C_2$-$C_6$)alkynylthio, ($C_1$-$C_6$)alkylsulfinyl, ($C_3$-$C_6$)cycloalkysulfinyl, ($C_1$-$C_6$)haloalkylsulfinyl, ($C_3$-$C_6$)halocycloalkylsulfinyl, ($C_2$-$C_6$)alkenylsulfinyl, ($C_3$-$C_6$)cycloalkenylsulfinyl, ($C_2$-$C_6$)alkynylsulfinyl, ($C_1$-$C_6$)alkylsulfonyl, ($C_3$-$C_6$)cycloalkysulfonyl, ($C_1$-$C_6$)haloalkylsulfonyl, ($C_3$-$C_6$)halocycloalkylsulfonyl, ($C_1$-$C_6$)alkylsulfinyl, ($C_3$-$C_6$)cycloalkysulfinyl, ($C_1$-$C_6$)haloalkylsulfinyl, ($C_3$-$C_6$)halocycloalkylsulfinyl, ($C_1$-$C_6$) alkylamino, ($C_3$-$C_6$)cycloalkylamino, di($C_1$-$C_6$) alkylamino, di($C_3$-$C_6$)(cycloalkyl)amino, ($C_1$-$C_6$) alkoxy($C_1$-$C_6$)alkyl, ($C_3$-$C_6$)cycloalkoxyalkyl, ($C_1$-$C_6$)alkoxy($C_3$-$C_6$)cycloalkyl, ($C_1$-$C_6$)alkylthio($C_1$-$C_6$)alkyl, ($C_1$-$C_6$)alkylsulfinyl($C_1$-$C_6$)alkyl, ($C_1$-$C_6$) alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$) alkylcarbonyl, ($C_3$-$C_6$)cycloalkylcarbonyl, ($C_1$-$C_6$) alkoxycarbonyl, ($C_1$-$C_6$)alkylaminocarbonyl, ($C_3$-$C_6$)cycloalkylaminocarbonyl, di($C_1$-$C_6$) alkylaminocarbonyl, di($C_3$-$C_6$)(cycloalkyl) aminocarbonyl, cyano($C_1$-$C_6$)alkyl, or tri($C_1$-$C_6$) alkylsilyl; or ii unsubstituted or substituted phenyl, phenyl($C_1$-$C_6$) alkyl, heterocyclyl, phenoxy, heterocyclyloxy, benzoyl, heterocyclylcarbonyl, phenylthio, heterocyclylthio, phenylsulfonyl, or heterocyclylsulfonyl, wherein one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, ($C_1$-$C_3$)alkylsulfonyl, ($C_1$-$C_3$)alkylamino, di($C_1$-$C_3$) alkylamino, ($C_1$-$C_2$)alkoxy($C_1$-$C_2$)alkyl, ($C_1$-$C_2$) alkylthio($C_1$-$C_2$)alkyl, ($C_1$-$C_2$)alkylsulfonyl($C_1$-$C_2$) alkyl, ($C_1$-$C_2$)alkylamino($C_1$-$C_2$)alkyl, di($C_1$-$C_2$) alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, di($C_1$-$C_3$)alkylaminocarbonyl and cyano($C_1$-$C_3$) alkyl;

wherein in said substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, ($C_1$-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$)alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, di($C_1$-$C_3$)alkylaminocarbonyl, cyano($C_1$-$C_3$)alkyl, oxo, and methoxyimino;
wherein the cells of the subject contain:
 a) an ecdysone receptor complex comprising:
  1) a DNA binding domain;
  2) a binding domain for the ligand; and
  3) a transactivation domain; and
 b) a DNA construct comprising:
  1) the exogenous gene; and
  2) a response element; and
wherein the exogenous gene is under the control of the response element, and binding of the DNA binding domain to the response element in the presence of the ligand results in activation or suppression of the gene.

8. A method for producing a polypeptide comprising the steps of:
 a) selecting a cell which is substantially insensitive to exposure to a ligand of the formula:

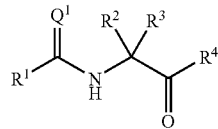

I wherein $Q^1$ is selected from the group consisting of O and S;
$R^1$ is:
 (a) ($C_1$-$C_6$)alkyl, ($C_3$-$C_6$)cycloalkyl, ($C_1$-$C_6$)haloalkyl, ($C_3$-$C_6$)halocycloalkyl, ($C_2$-$C_6$)alkenyl, ($C_2$-$C_6$)haloalkenyl, ($C_2$-$C_6$)alkynyl, ($C_2$-$C_6$)haloalkynyl, ($C_1$-$C_6$)alkoxy, ($C_3$-$C_6$)cycloalkoxy, ($C_1$-$C_6$)haloalkoxy, ($C_3$-$C_6$)halocycloalkoxy, ($C_2$-$C_6$)alkenyloxy, ($C_2$-$C_6$)alkynyloxy, ($C_1$-$C_6$)alkylthio, ($C_3$-$C_6$)cycloalkylthio, ($C_1$-$C_6$)haloalkylthio, ($C_3$-$C_6$)halocycloalkylthio, ($C_1$-$C_6$)alkylamino, ($C_3$-$C_6$)cycloalkylamino, ($C_1$-$C_6$)haloalkylamino, ($C_3$-$C_6$)halocycloalkylamino, di($C_1$-$C_6$)alkylamino, di($C_3$-$C_6$)cycloalkylamino, di($C_1$-$C_6$)haloalkylamino, di($C_3$-$C_6$)halocycloalkylamino, ($C_1$-$C_6$)alkoxy($C_1$-$C_6$)alkyl, ($C_1$-$C_6$)alkylthio($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl($C_1$-$C_6$)alkyl, or cyano($C_1$-$C_6$)alkyl; or
 (b) unsubstituted or substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, where the substituents are independently selected from one to four of the following:
  i cyano, nitro, halo, aminocarbonyl, aminothiocarbonyl, carboxy, formyl, hydroxy, amino, carbamoyl, ($C_1$-$C_6$)alkyl, ($C_3$-$C_6$)cycloalkyl, ($C_1$-$C_6$)haloalkyl, ($C_3$-$C_6$)halocycloalkyl, ($C_2$-$C_6$)alkenyl, ($C_3$-$C_6$)cycloalkenyl, ($C_3$-$C_6$)alkadienyl, ($C_2$-$C_6$)alkynyl, ($C_1$-$C_6$)alkoxy, ($C_3$-$C_6$)cycloalkoxy, ($C_1$-$C_6$)haloalkoxy, ($C_3$-$C_6$)cyclohaloalkoxy, ($C_2$-$C_6$)alkenyloxy, ($C_2$-$C_6$)alkynyloxy, ($C_1$-$C_6$)alkylthio, ($C_3$-$C_6$)cycloalkylthio, ($C_1$-$C_6$)haloalkylthio, ($C_3$-$C_6$)halocycloalkythio, ($C_2$-$C_6$)alkenylthio, ($C_2$-$C_6$)alkynylthio, ($C_1$-$C_6$)alkylsulfinyl, ($C_3$-$C_6$)cycloalkysulfinyl, ($C_1$-$C_6$)haloalkylsulfinyl, ($C_3$-$C_6$)halocycloalkylsulfinyl, ($C_2$-$C_6$)alkenylsulfinyl, ($C_3$-$C_6$)cycloalkenylsulfinyl, ($C_2$-$C_6$)alkynylsulfinyl, ($C_1$-$C_6$)alkylsulfonyl, ($C_3$-$C_6$)cycloalkysulfonyl, ($C_1$-$C_6$)haloalkylsulfonyl, ($C_3$-$C_6$)halocycloalkylsulfonyl, ($C_1$-$C_6$)alkylsulfinyl, ($C_3$-$C_6$)cycloalkysulfinyl, ($C_1$-$C_6$)haloalkylsulfinyl, ($C_3$-$C_6$)halocycloalkylsulfinyl, ($C_1$-$C_6$)alkylamino, ($C_3$-$C_6$)cycloalkylamino, di($C_1$-$C_6$)alkylamino, di($C_3$-$C_6$)(cycloalkyl)amino, ($C_1$-$C_6$)alkoxy($C_1$-$C_6$)alkyl, ($C_3$-$C_6$)cycloalkoxyalkyl, 1-$C_6$)alkoxy($C_3$-$C_6$)cycloalkyl, ($C_1$-$C_6$)alkylthio($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl, ($C_3$-$C_6$)cycloalkylcarbonyl, ($C_1$-$C_6$)alkoxycarbonyl, ($C_1$-$C_6$)alkylaminocarbonyl, ($C_3$-$C_6$)cycloalkylaminocarbonyl, di($C_1$-$C_6$)alkylaminocarbonyl, di($C_3$-$C_6$)(cycloalkyl)aminocarbonyl, cyano($C_1$-$C_6$)alkyl, or tri($C_1$-$C_6$)alkylsilyl; or
  ii unsubstituted or substituted phenyl, phenyl($C_1$-$C_6$)alkyl, heterocyclyl, phenoxy, heterocyclyloxy, benzoyl, heterocyclylcarbonyl, phenylthio, heterocyclylthio, phenylsulfonyl, or heterocyclylsulfonyl wherein one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, ($C_1$-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$)alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, di($C_1$-$C_3$)alkylaminocarbonyl or cyano($C_1$-$C_3$)alkyl wherein in said substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein:
the heterocyclic ring contains from one to three heteroatoms selected from N, 0, or and one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, 1-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$)alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, di($C_1$-$C_3$)alkylaminocarbonyl, cyano($C_1$-$C_3$)alkyl, oxo, and methoxyimino;
$R^2$ and $R^3$ are independently selected from:
 1. cyano, aminocarbonyl, carboxy, ($C_1$-$C_6$)alkyl, ($C_3$-$C_6$)cycloalkyl, halo($C_1$-$C_6$)alkyl, ($C_3$-$C_6$)halocycloalkyl, ($C_2$-$C_6$)alkenyl, ($C_3$-$C_6$)cycloalkenyl, ($C_2$-$C_6$)haloalkenyl, ($C_2$-$C_6$)alkynyl, ($C_1$-$C_6$)alkylsulfonyl, ($C_1$-$C_6$)alkoxy($C_1$-$C_6$)alkyl, ($C_1$-$C_6$)alkylthio($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl, ($C_1$-$C_6$)alkylcarbonyl($C_1$-$C_6$)alkyl, ($C_1$-$C_6$)alkylaminocarbonyl, di($C_1$-$C_6$)alkylaminocarbonyl, ($C_1$-$C_6$)alkylaminocarbonyl($C_1$-$C_6$)alkyl, di($C_1$-$C_6$)alkylaminocarbonyl($C_1$-$C_6$)alkyl, ($C_1$-$C_6$)alkylcarbonylamino($C_1$-$C_6$)alkyl, ($C_1$-$C_6$)alkoxycarbonyl, ($C_1$-$C_6$)alkoxycarbonyl($C_1$-$C_6$)alkyl, cyano($C_1$-$C_6$)alkyl, hydroxy($C_1$-$C_6$)alkyl, or carboxy($C_1$-$C_6$)alkyl; or 2. unsubstituted or substituted phenyl, phenyl($C_1$-$C_6$)alkyl, benzoyl, naphthyl, pyridyl, pyrazinyl, pyridazinyl, pyrimidinyl, furanyl, thiophenyl, benzothiophenyl, benzofuranyl, isoxazolyl, imidazolyl or other heterocyclyl, heterocyclylcarbonyl, wherein one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, ($C_1$-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$)alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, di($C_1$-$C_3$)alkylaminocarbonyl, and cyano($C_1$-$C_3$)alkyl;

wherein $R^2$ and $R^3$ may be joined together with the carbon to which they are attached to form an unsubstituted or substituted, partially unsaturated or saturated 3-, 4-, 5-, 6-, 7- or 8-membered carbocyclic or heterocyclic ring wherein the heterocyclic ring contains from one to three heteroatoms selected from O, N, or S; and one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, ($C_1$-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$)alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_4$)alkoxycarbonyl($C_1$-$C_4$)alkyl, ($C_1$-$C_4$)alkoxycarbonyl, ($C_1$-$C_4$)alkoxycarbonylcarbonyl, ($C_1$-$C_3$)alkylaminocarbonyl, di($C_1$-$C_3$)alkylaminocarbonyl, cyano($C_1$-$C_3$)alkyl, oxo, methoxyimino, and spiro-($C_1$-$C_4$)alkadioxy; and $R^4$ is selected from:

(a) ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_3$-$C_6$)cycloalkoxy, 1-$C_6$)haloalkoxy, ($C_3$-$C_6$)halocycloalkoxy, ($C_2$-$C_6$)alkenyloxy, ($C_2$-$C_6$)alkynyloxy, ($C_1$-$C_6$)alkylthio, ($C_3$-$C_6$)cycloalkylthio, ($C_1$-$C_6$)haloalkylthio, ($C_3$-$C_6$)halocycloalkylthio, ($C_1$-$C_6$)alkylamino, ($C_3$-$C_6$)cycloalkylamino, ($C_1$-$C_6$)haloalkylamino, ($C_3$-$C_6$)halocycloalkylamino, di($C_1$-$C_6$)alkylamino, di($C_3$-$C_6$)cycloalkylamino, di($C_1$-$C_6$)haloalkylamino, di($C_3$-$C_6$)halocycloalkylamino, ($C_1$-$C_6$)alkoxy($C_1$-$C_6$)alkyl, ($C_1$-$C_6$)alkylthio($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl($C_1$-$C_6$)alkyl, or cyano($C_1$-$C_6$)alkyl; or (b) unsubstituted or substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein one to four substituents are independently selected from:

i cyano, nitro, halo, aminocarbonyl, aminothiocarbonyl, carboxy, formyl, hydroxy, amino, carbamoyl, ($C_1$-$C_6$)alkyl, ($C_3$-$C_6$)cycloalkyl, ($C_1$-$C_6$)haloalkyl, ($C_3$-$C_6$)halocycloalkyl, ($C_2$-$C_6$)alkenyl, ($C_3$-$C_6$)cycloalkenyl, ($C_3$-$C_6$)alkadienyl, ($C_2$-$C_6$)alkynyl, ($C_1$-$C_6$)alkoxy, ($C_3$-$C_6$)cycloalkoxy, ($C_1$-$C_6$)haloalkoxy, ($C_3$-$C_6$)cyclohaloalkoxy, ($C_2$-$C_6$)alkenyloxy, ($C_2$-$C_6$)alkynyloxy, ($C_1$-$C_6$)alkylthio, ($C_3$-$C_6$)cycloalkylthio, ($C_1$-$C_6$)haloalkylthio, ($C_3$-$C_6$)halocycloalkythio, ($C_2$-$C_6$)alkenylthio, ($C_2$-$C_6$)alkynylthio, ($C_1$-$C_6$)alkylsulfinyl, ($C_3$-$C_6$)cycloalkysulfinyl, ($C_1$-$C_6$)haloalkylsulfinyl, ($C_3$-$C_6$)halocycloalkylsulfinyl, ($C_2$-$C_6$)alkenylsulfinyl, ($C_3$-$C_6$)cycloalkenylsulfinyl, ($C_2$-$C_6$)alkynylsulfinyl, ($C_1$-$C_6$)alkylsulfonyl, ($C_3$-$C_6$)cycloalkysulfonyl, $C_1$-$C_6$)haloalkylsulfonyl, ($C_3$-$C_6$)halocycloalkylsulfonyl, ($C_1$-$C_6$)alkylsulfinyl, ($C_3$-$C_6$)cycloalkysulfinyl, ($C_1$-$C_6$)haloalkylsulfinyl, ($C_3$-$C_6$)halocycloalkylsulfinyl, ($C_1$-$C_6$)alkylamino, ($C_3$-$C_6$)cycloalkylamino, di($C_1$-$C_6$)alkylamino, di($C_3$-$C_6$)(cycloalkyl)amino, ($C_1$-$C_6$)alkoxy($C_1$-$C_6$)alkyl, ($C_3$-$C_6$)cycloalkoxyalkyl, ($C_1$-$C_6$)alkoxy($C_3$-$C_6$)cycloalkyl, ($C_1$-$C_6$)alkylthio($C_1$-$C_6$)alkyl, ($C_2$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl, ($C_3$-$C_6$)cycloalkylcarbonyl, ($C_1$-$C_6$)alkoxycarbonyl, ($C_1$-$C_6$)alkylaminocarbonyl, ($C_3$-$C_6$)cycloalkylaminocarbonyl, di($C_1$-$C_6$)alkylaminocarbonyl, di($C_3$-$C_6$)(cycloalkyl)aminocarbonyl, cyano($C_1$-$C_6$)alkyl, or tri($C_1$-$C_6$)alkylsilyl; or ii unsubstituted or substituted phenyl, phenyl($C_1$-$C_6$)alkyl, heterocyclyl, phenoxy, heterocyclyloxy, benzoyl, heterocyclylcarbonyl, phenylthio, heterocyclylthio, phenylsulfonyl, or heterocyclylsulfonyl, wherein one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, 1-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$)alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, di($C_1$-$C_3$)alkylaminocarbonyl and cyano($C_1$-$C_3$)alkyl;

wherein in said substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $1-C_3)$alkylaminocarbonyl, di$(C_1-C_3)$alkylaminocarbonyl, cyano$(C_1-C_3)$alkyl, oxo, and methoxyimino;
b) introducing into the cell:
 1) a DNA construct comprising:
  a) an exogenous gene encoding the polypeptide; and
  b) a response element;
  wherein the gene is under the control of the response element; and
 2) an ecdysone receptor complex comprising:
  a) a DNA binding domain;
  b) a binding domain for the ligand; and
  c) a transactivation domain; and
c) exposing the cell to the ligand.

9. A method for regulating endogenous or heterologous gene expression in a transgenic subject comprising contacting a ligand with an ecdysone receptor complex within the cells of the subject wherein the cells further contain a DNA binding sequence for the ecdysone receptor complex when in combination with the ligand and wherein formation of an ecdysone receptor complex-ligand-DNA binding sequence complex induces expression of the gene, and where the ligand has the following formula:

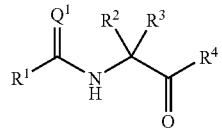

I wherein $Q^1$ is selected from the group consisting of O and S;
$R^1$ is:
 a) $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_2-C_6)$haloalkenyl, $(C_2-C_6)$alkynyl, $(C_2-C_6)$haloalkynyl, $(C_1-C_6)$alkoxy, $(C_3-C_6)$cycloalkoxy, $(C_1-C_6)$haloalkoxy, $(C_3-C_6)$halocycloalkoxy, $(C_2-C_6)$alkenyloxy, $(C_2-C_6)$alkynyloxy, $(C_1-C_6)$alkylthio, $(C_3-C_6)$cycloalkylthio, $1-C_6)$haloalkylthio, $(C_3-C_6)$halocycloalkylthio, $(C_1-C_6)$alkylamino, $(C_3-C_6)$cycloalkylamino, $(C_1-C_6)$haloalkylamino, $(C_1-C_6)$halocycloalkylamino, di$(C_1-C_6)$alkylamino, di$(C_3-C_6)$cycloalkylamino, di$(C_1-C_6)$haloalkylamino, di$(C_3-C_6)$halocycloalkylamino, $(C_1-C_6)$alkoxy$(C_1-C_6)$alkyl, $(C_1-C_6)$alkylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl$(C_1-C_6)$alkyl, or cyano$(C_1-C_6)$alkyl; or
 (b) unsubstituted or substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, where the substituents are independently selected from one to four of the following:
  i cyano, nitro, halo, aminocarbonyl, aminothiocarbonyl, carboxy, formyl, hydroxy, amino, carbamoyl, $(C_1-C_6)$alkyl, $(C_3-C_6)$cycloalkyl, $(C_1-C_6)$haloalkyl, $(C_3-C_6)$halocycloalkyl, $(C_2-C_6)$alkenyl, $(C_3-C_6)$cycloalkenyl, $(C_3-C_6)$alkadienyl, $(C_2-C_6)$alkynyl, $(C_1-C_6)$alkoxy, $(C_3-C_6)$cycloalkoxy, $(C_1-C_6)$haloalkoxy, $(C_3-C_6)$cyclohaloalkoxy, $(C_2-C_6)$alkenyloxy, $(C_2-C_6)$alkynyloxy, $(C_1-C_6)$alkythio, $(C_3-C_6)$cycloalkylthio, $(C_1-C_6)$haloalkylthio, $(C_3-C_6)$halocycloalkythio, $(C_2-C_6)$alkenylthio, $(C_2-C_6)$alkynylthio, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_2-C_6)$alkenylsulfinyl, $(C_3-C_6)$cycloalkenylsulfinyl, $(C_2-C_6)$alkynylsulfinyl, $(C_1-C_6)$alkylsulfonyl, $(C_3-C_6)$cycloalkysulfonyl, $(C_1-C_6)$haloalkylsulfonyl, $(C_3-C_6)$halocycloalkylsulfonyl, $(C_1-C_6)$alkylsulfinyl, $(C_3-C_6)$cycloalkysulfinyl, $(C_1-C_6)$haloalkylsulfinyl, $(C_3-C_6)$halocycloalkylsulfinyl, $(C_1-C_6)$alkylamino, $(C_3-C_6)$cycloalkylamino, di$(C_1-C_6)$alkylamino, di$(C_3-C_6)$(cycloalkyl)amino, $(C_1-C_6)$alkoxy$(C_1-C_6)$alkyl, $(C_3-C_6)$cycloalkoxyalkyl, $(C_1-C_6)$alkoxy$(C_3-C_6)$cycloalkyl, $(C_1-C_6)$alkylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylcarbonyl, $(C_3-C_6)$cycloalkylcarbonyl, $(C_1-C_6)$alkoxycarbonyl, $(C_1-C_6)$alkylaminocarbonyl, $(C_3-C_6)$cycloalkylaminocarbonyl, di$(C_1-C_6)$alkylaminocarbonyl, di$(C_3-C_6)$(cycloalkyl)aminocarbonyl, cyano$(C_1-C_6)$alkyl, or tri$(C_1-C_6)$alkylsilyl; or
  ii unsubstituted or substituted phenyl, phenyl$(C_1-C_6)$alkyl, heterocyclyl, phenoxy, heterocyclyloxy, benzoyl, heterocyclylcarbonyl, phenylthio, heterocyclylthio, phenylsulfonyl, or heterocyclylsulfonyl wherein one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_2)$alkylcarbonyl, $(C_1-C_3)$alkoxycarbonyl, $(C_1-C_3)$alkylaminocarbonyl, di$(C_1-C_3)$alkylaminocarbonyl or cyano$(C_1-C_3)$alkyl;
 wherein in said substituted phenyl, 1-naphthyl, 2-naphthyl, phenyl$(C_1-C_3)$alkyl, phenyl$(C_2-C_3)$alkenyl, naphthyl$(C_1-C_3)$alkyl, phenoxy$(C_1-C_3)$alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein:
  the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $(C_1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$ alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, 1-$C_3$)alkylaminocarbonyl, di($C_1$-$C_3$)alkylaminocarbonyl, cyano($C_1$-$C_3$)alkyl, oxo, and methoxyimino;

$R^2$ and $R^3$ are independently selected from:

(a) cyano, aminocarbonyl, carboxy, ($C_1$-$C_6$)alkyl, ($C_3$-$C_6$)cycloalkyl, halo($C_1$-$C_6$)alkyl, ($C_3$-$C_6$)halocycloalkyl, ($C_2$-$C_6$)alkenyl, ($C_3$-$C_6$)cycloalkenyl, ($C_2$-$C_6$)haloalkenyl, ($C_2$-$C_6$)alkynyl, ($C_1$-$C_6$)alkylsulfonyl, ($C_1$-$C_6$)alkoxy($C_1$-$C_6$)alkyl, ($C_1$-$C_6$)alkylthio($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl, ($C_1$-$C_6$)alkylcarbonyl($C_1$-$C_6$)alkyl, ($C_1$-$C_6$)alkylaminocarbonyl, di($C_1$-$C_6$)alkylaminocarbonyl, ($C_1$-$C_6$)alkylaminocarbonyl($C_1$-$C_6$)alkyl, di($C_1$-$C_6$)alkylaminocarbonyl($C_1$-$C_6$)alkyl, ($C_1$-$C_6$)alkylcarbonylamino($C_1$-$C_6$)alkyl, ($C_1$-$C_6$)alkoxycarbonyl, ($C_1$-$C_6$)alkoxycarbonyl($C_1$-$C_6$)alkyl, cyano($C_1$-$C_6$)alkyl, hydroxy($C_1$-$C_6$)alkyl, or carboxy($C_1$-$C_6$)alkyl; or (b) unsubstituted or substituted phenyl, phenyl($C_1$-$C_6$)alkyl, benzoyl, naphthyl, pyridyl, pyrazinyl, pyridazinyl, pyrimidinyl, furanyl, thiophenyl, benzothiophenyl, benzofuranyl, isoxazolyl, imidazolyl or other heterocyclyl, heterocyclylcarbonyl, wherein one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, ($C_1$-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$)alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, di($C_1$-$C_3$)alkylaminocarbonyl, and cyano($C_1$-$C_3$)alkyl;

wherein $R^2$ and $R^3$ may be joined together with the carbon to which they are attached to form an unsubstituted or substituted, partially unsaturated or saturated 3-, 4-, 5-, 6-, 7- or 8-membered carbocyclic or heterocyclic ring wherein the heterocyclic ring contains from one to three heteroatoms selected from O, N, or S; and one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, ($C_1$-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$)alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_4$)alkoxycarbonyl, ($C_1$-$C_4$)alkoxycarbonyl($C_1$-$C_4$)alkyl, ($C_1$-$C_4$)alkoxycarbonylcarbonyl, ($C_1$-$C_3$)alkylaminocarbonyl, di($C_1$-$C_3$)alkylaminocarbonyl, cyano($C_1$-$C_3$)alkyl, oxo, methoxyimino, and spiro-($C_1$-$C_4$)alkadioxy; and $R^4$ is selected from:

(a) ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_3$-$C_6$)cycloalkoxy, ($C_1$-$C_6$)haloalkoxy, ($C_3$-$C_6$)halocycloalkoxy, ($C_2$-$C_6$)alkenyloxy, ($C_2$-$C_6$)alkynyloxy, ($C_1$-$C_6$)alkylthio, ($C_3$-$C_6$)cycloalkylthio, ($C_1$-$C_6$)haloalkylthio, ($C_3$-$C_6$)halocycloalkylthio, ($C_1$-$C_6$)alkylamino, ($C_3$-$C_6$)cycloalkylamino, ($C_1$-$C_6$)haloalkylamino, ($C_3$-$C_6$)halocycloalkylamino, di($C_1$-$C_6$)alkylamino, di($C_3$-$C_6$)cycloalkylamino, di($C_1$-$C_6$)haloalkylamino, di($C_3$-$C_6$)halocycloalkylamino, ($C_1$-$C_6$)alkoxy($C_1$-$C_6$)alkyl, ($C_1$-$C_6$)alkylthio($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl($C_1$-$C_6$)alkyl, or cyano($C_1$-$C_6$)alkyl; or (b) unsubstituted or substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, wherein one to four substituents are independently selected from:

i cyano, nitro, halo, aminocarbonyl, aminothiocarbonyl, carboxy, formyl, hydroxy, amino, carbamoyl, ($C_1$-$C_6$)alkyl, ($C_3$-$C_6$)cycloalkyl, ($C_1$-$C_6$)haloalkyl, ($C_3$-$C_6$)halocycloalkyl, ($C_2$-$C_6$)alkenyl, ($C_3$-$C_6$)cycloalkenyl, ($C_3$-$C_6$)alkadienyl, ($C_2$-$C_6$)alkynyl, ($C_1$-$C_6$)alkoxy, ($C_3$-$C_6$)cycloalkoxy, ($C_1$-$C_6$)haloalkoxy, ($C_3$-$C_6$)cyclohaloalkoxy, ($C_2$-$C_6$)alkenyloxy, ($C_2$-$C_6$)alkynyloxy, ($C_1$-$C_6$)alkythio, ($C_3$-$C_6$)cycloalkylthio, ($C_1$-$C_6$)haloalkylthio, ($C_3$-$C_6$)halocycloalkythio, ($C_2$-$C_6$)alkenylthio, ($C_2$-$C_6$)alkynylthio, ($C_1$-$C_6$)alkylsulfinyl, ($C_3$-$C_6$)cycloalkysulfinyl, ($C_1$-$C_6$)haloalkylsulfinyl, ($C_3$-$C_6$)halocycloalkylsulfinyl, ($C_2$-$C_6$)alkenylsulfinyl, ($C_3$-$C_6$)cycloalkenylsulfinyl, ($C_2$-$C_6$)alkynylsulfinyl, ($C_1$-$C_6$)alkylsulfonyl, ($C_3$-$C_6$)cycloalkysulfonyl, ($C_1$-$C_6$)haloalkylsulfonyl, ($C_3$-$C_6$)halocycloalkylsulfonyl, ($C_1$-$C_6$)alkylsulfinyl, ($C_3$-$C_6$)cycloalkysulfinyl, ($C_1$-$C_6$)haloalkylsulfinyl, ($C_3$-$C_6$)halocycloalkylsulfinyl, ($C_1$-$C_6$)alkylamino, ($C_3$-$C_6$)cycloalkylamino, di($C_1$-$C_6$)alkylamino, di($C_3$-$C_6$)(cycloalkyl)amino, ($C_1$-$C_6$)alkoxy($C_1$-$C_6$)alkyl, ($C_3$-$C_6$)cycloalkoxyalkyl, ($C_1$-$C_6$)alkoxy($C_3$-$C_6$)cycloalkyl, ($C_1$-$C_6$) alkylthio($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, ($C_1$-$C_6$)alkylamino($C_1$-$C_6$)alkyl, di($C_1$-$C_6$)alkylamino($C_1$-$C_6$)alkyl, ($C_1$-$C_6$)alkylcarbonyl, ($C_3$-$C_6$)cycloalkylcarbonyl, ($C_1$-$C_6$)alkoxycarbonyl, ($C_1$-$C_6$)alkylaminocarbonyl, ($C_3$-$C_6$)cycloalkylaminocarbonyl, di($C_1$-$C_6$)alkylaminocarbonyl, di($C_3$-$C_6$)(cycloalkyl)aminocarbonyl, cyano($C_1$-$C_6$)alkyl, or tri($C_1$-$C_6$)alkylsilyl; or ii unsubstituted or substituted phenyl, phenyl($C_1$-$C_6$)alkyl, heterocyclyl, phenoxy, heterocyclyloxy, benzoyl, heterocyclylcarbonyl, phenylthio, heterocyclylthio, phenylsulfonyl, or heterocyclylsulfonyl, wherein one to four substituents are independently selected from the group consisting of cyano, nitro, halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkythio, ($C_1$-$C_3$)haloalkylthio, ($C_1$-$C_3$)alkylsulfonyl, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylthio($C_1$-$C_2$)alkyl, ($C_1$-$C_2$)alkylsulfonyl($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, di($C_1$-$C_3$)alkylaminocarbonyl and cyano($C_1$-$C_3$)alkyl;

wherein in said substituted phenyl, 1-naphthyl, 2-naphthyl, phenyl($C_1$-$C_3$)alkyl, phenyl($C_2$-$C_3$)alkenyl, naphthyl($C_1$-$C_3$)alkyl, phenoxy($C_1$-$C_3$)alkyl, phenylamino, pyridyl, pyrazinyl, pyridazinyl, pyrimidinyl, furanyl, thiophenyl, benzothiophenyl, benzofuranyl, isoxazolyl, imidazolyl or other heterocyclyl, two adjacent substituted positions may be joined together with the atoms to which they are attached to form an unsubstituted or substituted, unsaturated, partially unsaturated, or saturated 4-, 5-, 6- or 7-membered carbocyclic or heterocyclic ring wherein the heterocyclic ring contains from one to three heteroatoms selected from N, O, or S; and one to four substituents are independently selected from the group consisting of cyano, nitro, halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $(C_1-C_3)$alkylsulfonyl, $1-C_3)$alkylamino, di$(C_1-C_3)$alkylamino, $(C_1-C_2)$alkoxy$(C_1-C_2)$alkyl, $(C_1-C_2)$alkylthio$(C_1-C_2)$alkyl, $(C_1-C_2)$alkylsulfonyl$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$alkoxycarbonyl, $(C_1-C_3)$alkylaminocarbonyl, di$(C_1-C_3)$alkylaminocarbonyl, cyano$(C_1-C_3)$alkyl, oxo, and methoxyimino.

10. The method of claim 9, wherein the ecdysone receptor complex is a chimeric ecdysone receptor complex and the DNA construct further comprises a promoter.

11. The method of claim 9, wherein the subject is a plant.

12. The method of claim 9, wherein the subject is a mammal.

* * * * *

UNITED STATES PATENT AND TRADEMARK OFFICE
CERTIFICATE OF CORRECTION

PATENT NO. : 7,375,093 B2
APPLICATION NO. : 10/614116
DATED : May 20, 2008
INVENTOR(S) : Tice et al.

It is certified that error appears in the above-identified patent and that said Letters Patent is hereby corrected as shown below:

In claim 1, column 101, line 50, please delete "1-$C_6$)haloalkylthio" and insert therefor -- ($C_1$-$C_6$)haloalkylthio --;

column 102, line 37, please delete "($C_1$-$C_6$)alkylsulfinyl(Ct-$C_6$)alkyl" and insert therefor -- ($C_1$-$C_6$)alkylsulfinyl($C_1$-$C_6$)alkyl --;

column 102, lines 38-39, please delete "$C_1$-$C_6$)alkylamino($C_1$-$C_6$)alkyl" and insert therefor -- ($C_1$-$C_6$)alkylamino($C_1$-$C_6$)alkyl --;

column 102, line 56, please delete "i-$C_2$)alkylthio($C_1$-$C_2$)alkyl" and insert therefor -- ($C_1$-$C_2$)alkylthio($C_1$-$C_2$)alkyl --;

column 103, line 15, please delete "1-$C_3$)alkoxycarbonyl" and insert therefor -- ($C_1$-$C_3$)alkoxycarbonyl --;

column 103, line 57, please delete "0" and insert therefor -- O --;

column 103, lines 62-63, please delete "1-$C_3$)alkylamino" and insert therefor -- ($C_1$-$C_3$)alkylamino --;

column 104, line 45, please delete "1-$C_6$)haloalkylsulfinyl" and insert therefor -- ($C_1$-$C_6$)haloalkylsulfinyl --; and column 105, line 2, please delete "1-$C_3$)alkylamino" and insert therefor -- ($C_1$-$C_3$)alkylamino --.

In claim 2, column 105, line 67, please delete "0, or" and insert therefor -- O, or S; --;

column 106, line 13, after "methoxyimino" please insert -- ; --;

column 106, line 26, please delete "1-$C_3$)haloalkylsulfonyl, 1-$C_3$)alkylamino" and insert therefor -- ($C_1$-$C_3$)haloalkylsulfonyl, ($C_1$-$C_3$)alkylamino --;

column 106, line 49, please delete "$C_3$)alkoxycarbonyl" and insert therefor -- ($C_1$-$C_3$)alkoxycarbonyl --;

column 106, line 51, after "positions on" please insert -- $R^4$ --;

column 106, lines 63-64, please delete "$C_1$-$C_3$)alkylsulfonyl" and insert therefor -- ($C_1$-$C_3$)alkylsulfonyl --; and column 106, line 67, please delete "di($C_1$-$C_2$)alkylamino($C_1$-$C_9$alkyl" and insert therefor -- di($C_1$-$C_2$)alkylamino($C_1$-$C_2$)alkyl --;

column 107, line 3, after "methoxyimino" please insert -- . --.

In claim 3, column 107, line 52, please delete "1-$C_3$)alkylamino" and insert therefor -- ($C_1$-$C_3$)alkylamino --;

column 108, line 6, please delete "1-$C_3$)alkoxycarbonyl" and insert therefor -- ($C_1$-$C_3$)alkoxycarbonyl --;

column 108, line 8, after "positions on" please insert -- $R^4$ --;

column 108, line 15, please delete "1-$C_3$)alkyl" and insert therefor -- ($C_1$-$C_3$)alkyl --; and column 108, line 20, please delete "1-$C_4$)alkoxycarbonyl" and insert therefor -- ($C_1$-$C_4$)alkoxycarbonyl --.

UNITED STATES PATENT AND TRADEMARK OFFICE
CERTIFICATE OF CORRECTION

PATENT NO. : 7,375,093 B2
APPLICATION NO. : 10/614116
DATED : May 20, 2008
INVENTOR(S) : Tice et al.

It is certified that error appears in the above-identified patent and that said Letters Patent is hereby corrected as shown below:

In claim 4, column 108, line 57, please delete "of($C_1$-$C_3$)alkyl" and insert therefor -- of ($C_1$-$C_3$)alkyl --;
    column 108, line 58, please delete "($C_1$-$C_4$alkoxycarbonyl" and insert therefor -- ($C_1$-$C_4$)alkoxycarbonyl --; and
    column 108, line 64, please delete ";" and insert therefor -- . --.

In claim 5, column 109, line 5, please delete ";" and insert therefor -- . --.

In claim 7, column 109, line 65, please delete "1-$C_6$)haloalkylsulfonyl" and insert therefor -- ($C_1$-$C_6$)haloalkylsulfonyl --;
    column 110, lines 3-4, please delete "($C_1$-.$C_6$)alkoxy($C_1$-$C_6$)alkyl" and insert therefor -- ($C_1$-$C_6$)alkoxy($C_1$-$C_6$)alkyl --;
    column 110, line 24, please delete "1-$C_3$)alkylamino" and insert therefor -- ($C_1$-$C_3$)alkylamino --;
    column 110, line 42, after "N, O, or", please insert -- S; --;
    column 110, line 50, please delete "($C_1$-$C_2$)alkylamino(Ct-$C_2$)alkyl" and insert therefor -- ($C_1$-$C_2$)alkylamino($C_1$-$C_2$)alkyl --; and
    column 111, line 20, please delete "1-$C_3$)alkoxycarbonyl" and insert therefor -- ($C_1$-$C_3$)alkoxycarbonyl --.

In claim 8, column 114, lines 10-11, please delete "1-$C_6$)alkoxy($C_3$-$C_6$)cycloalkyl" and insert therefor -- ($C_1$-$C_6$)alkoxy($C_3$-$C_6$)cycloalkyl --;
    column 114, line 37, after "cyano($C_1$-$C_3$)alkyl" please insert -- ; --;
    column 114, line 49, please delete "0, or" and insert therefor -- O, or S; --;
    column 114, line 54, please delete "1-$C_3$)alkylsulfonyl" and insert therefor -- ($C_1$-$C_3$)alkylsulfonyl --; and
    column 115, line 10, please delete "cyano($C_1$-.$C_6$)alkyl" and insert therefor -- cyano($C_1$-$C_6$)alkyl --;
    column 115, line 22, please delete "(C 1-$C_3$)alkylsulfonyl" and insert therefor -- ($C_1$-$C_3$)alkylsulfonyl --;
    column 115, lines 51-52, please delete "1-$C_6$)haloalkoxy" and insert therefor -- ($C_1$-$C_6$)haloalkoxy --;
    column 116, line 20, please delete "$C_1$-$C_6$)haloalkylsulfonyl" and insert therefor -- ($C_1$-$C_6$)haloalkylsulfonyl --;
    column 116, line 47, please delete "1-$C_3$)alkylsulfonyl" and insert therefor -- ($C_1$-$C_3$)alkylsulfonyl --; and
    column 117, lines 8-9, please delete "1-$C_3$)alkylaminocarbonyl" and insert therefor -- ($C_1$-$C_3$)alkylaminocarbonyl --.

UNITED STATES PATENT AND TRADEMARK OFFICE
CERTIFICATE OF CORRECTION

PATENT NO.        : 7,375,093 B2
APPLICATION NO.   : 10/614116
DATED             : May 20, 2008
INVENTOR(S)       : Tice et al.

It is certified that error appears in the above-identified patent and that said Letters Patent is hereby corrected as shown below:

In claim 9, column 117, line 50, please delete "1-$C_6$)haloalkylthio" and insert therefor -- ($C_1$-$C_6$)haloalkylthio --;
    column 117, line 52, please delete "($C_1$-$C_6$)halocycloalkylamino" and insert therefor -- ($C_3$-$C_6$)halocycloalkylamino --;
    column 118, line 42, please delete "1-$C_3$)alkylamino" and insert therefor -- ($C_1$-$C_3$)alkylamino --;
    column 119, line 3, please delete "1-$C_3$)alkylaminocarbonyl" and insert therefor -- ($C_1$-$C_3$)alkylaminocarbonyl --; and
    column 121, line 14, please delete "1-$C_3$)alkylamino" and insert therefor -- ($C_1$-$C_3$)alkylamino --.

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO.       : 7,375,093 B2                                Page 1 of 1
APPLICATION NO.  : 10/614116
DATED            : May 20, 2008
INVENTOR(S)      : Tice et al.

It is certified that error appears in the above-identified patent and that said Letters Patent is hereby corrected as shown below:

Column 109, line 6, the claim reference numeral "5" should read -- 3 --.

Signed and Sealed this
Twenty-seventh Day of September, 2011

David J. Kappos
*Director of the United States Patent and Trademark Office*